United States Patent
Wang et al.

(10) Patent No.: US 11,161,891 B2
(45) Date of Patent: Nov. 2, 2021

(54) RELAXIN IMMUNOGLOBULIN FUSION PROTEINS AND METHODS OF USE

(71) Applicant: The Scripps Research Institute, La Jolla, CA (US)

(72) Inventors: Feng Wang, Beijing (CN); Yan Liu, San Diego, CA (US); Ying Wang, San Diego, CA (US); Guangsen Fu, San Diego, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 21 days.

(21) Appl. No.: 16/060,384

(22) PCT Filed: Dec. 9, 2016

(86) PCT No.: PCT/US2016/065779
§ 371 (c)(1),
(2) Date: Jun. 7, 2018

(87) PCT Pub. No.: WO2017/100540
PCT Pub. Date: Jun. 15, 2017

(65) Prior Publication Data
US 2019/0263882 A1    Aug. 29, 2019

Related U.S. Application Data

(60) Provisional application No. 62/265,344, filed on Dec. 9, 2015.

(51) Int. Cl.
| | | |
|---|---|---|
| *A61K 9/00* | (2006.01) | |
| *C07K 14/64* | (2006.01) | |
| *A61P 13/12* | (2006.01) | |
| *A61P 11/00* | (2006.01) | |
| *A61K 9/02* | (2006.01) | |
| *A61K 9/10* | (2006.01) | |
| *C07K 16/10* | (2006.01) | |
| *A61K 38/00* | (2006.01) | |
| *A61K 39/00* | (2006.01) | |

(52) U.S. Cl.
CPC ............ *C07K 14/64* (2013.01); *A61K 9/0019* (2013.01); *A61K 9/0048* (2013.01); *A61K 9/02* (2013.01); *A61K 9/10* (2013.01); *A61P 11/00* (2018.01); *A61P 13/12* (2018.01); *C07K 16/1027* (2013.01); *A61K 38/00* (2013.01); *A61K 2039/505* (2013.01); *A61K 2039/54* (2013.01); *A61K 2039/545* (2013.01); *C07K 2317/24* (2013.01); *C07K 2317/52* (2013.01); *C07K 2317/565* (2013.01); *C07K 2317/732* (2013.01); *C07K 2317/76* (2013.01); *C07K 2317/92* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 5,911,997 A | 6/1999 | Schwabe et al. |
| 6,211,147 B1 | 4/2001 | Unemori |
| 6,372,716 B1 | 4/2002 | Bush et al. |
| 6,566,329 B1 | 5/2003 | Meyn et al. |
| 6,685,940 B2 | 2/2004 | Andya et al. |
| 6,723,702 B2 | 4/2004 | Conrad et al. |
| 6,740,747 B2 | 5/2004 | Kaushik et al. |
| 6,780,836 B2 | 8/2004 | Unemori |
| 6,984,128 B2 | 1/2006 | Breining et al. |
| 7,553,813 B2 | 6/2009 | Unemori |
| 7,878,978 B2 | 2/2011 | Conrad et al. |
| 8,026,215 B2 | 9/2011 | Unemori |
| 8,053,411 B2 | 11/2011 | Unemori et al. |
| 8,372,809 B2 | 2/2013 | Unemori et al. |
| 8,415,301 B2 | 4/2013 | Unemori et al. |
| 8,602,998 B2 | 12/2013 | Conrad et al. |
| 9,644,021 B2 | 5/2017 | Wang et al. |
| 2002/0164326 A1 | 11/2002 | Young et al. |
| 2004/0192606 A1 | 9/2004 | Unemori |
| 2004/0266685 A1 | 12/2004 | Conrad et al. |
| 2005/0186526 A1 | 8/2005 | Stewart et al. |
| 2006/0159695 A1 | 7/2006 | Delvecchio et al. |
| 2006/0247172 A1 | 11/2006 | Unemori |
| 2006/0257918 A1 | 11/2006 | Ramanathan et al. |
| 2006/0269892 A1 | 11/2006 | Breining et al. |
| 2007/0293485 A1 | 12/2007 | Lim et al. |

(Continued)

FOREIGN PATENT DOCUMENTS

| | | |
|---|---|---|
| AU | 2012211451 A1 | 8/2012 |
| EP | 0133988 A2 | 3/1985 |

(Continued)

OTHER PUBLICATIONS

Rudikoff et al, Proc. Natl. Acad. Sci. USA, 79:1979-1983 (Year: 1982).*
Casset et al., Biochemical and Biophysical Research Communications, 307:198-205 (Year: 2003).*
Paul, Fundamental Immunology, 3rd Edition, pp. 292-295 (Year: 1993).*

(Continued)

*Primary Examiner* — Shanon A. Foley
*Assistant Examiner* — Myron G Hill
(74) *Attorney, Agent, or Firm* — Wilson Sonsini Goodrich & Rosati

(57) ABSTRACT

Disclosed herein are relaxin immunoglobulin fusion proteins useful for the treatment or prevention of a disease or condition in a subject.

13 Claims, 15 Drawing Sheets
Specification includes a Sequence Listing.

(56) References Cited

U.S. PATENT DOCUMENTS

| | | |
|---|---|---|
| 2008/0108572 A1 | 5/2008 | Unemori |
| 2008/0260731 A1 | 10/2008 | Bernett et al. |
| 2010/0041603 A1 | 2/2010 | Stewart |
| 2011/0144019 A1 | 6/2011 | Unemori et al. |
| 2011/0166070 A1 | 7/2011 | Stewart et al. |
| 2011/0245469 A1 | 10/2011 | Wang |
| 2011/0293513 A1 | 12/2011 | Govindan et al. |
| 2013/0053318 A1 | 2/2013 | Laura et al. |
| 2013/0116181 A1 | 5/2013 | Unemori et al. |
| 2013/0210730 A1 | 8/2013 | Unemori et al. |
| 2014/0005112 A1 | 1/2014 | Unemori et al. |
| 2014/0057832 A1 | 2/2014 | Conrad et al. |
| 2014/0066377 A1 | 3/2014 | Parry et al. |
| 2014/0086871 A1 | 3/2014 | Smider et al. |
| 2014/0148390 A1 | 5/2014 | Haupts et al. |
| 2014/0187491 A1 | 7/2014 | Wilmen et al. |
| 2014/0227267 A1 | 8/2014 | Wang et al. |
| 2015/0011431 A1 | 1/2015 | Smider et al. |
| 2016/0159920 A1 | 6/2016 | Wang et al. |
| 2016/0237156 A1 | 8/2016 | Wang et al. |
| 2017/0327577 A1 | 11/2017 | Wang et al. |

FOREIGN PATENT DOCUMENTS

| | | |
|---|---|---|
| EP | 2311882 A1 | 4/2011 |
| WO | WO-9315722 A1 | 8/1993 |
| WO | WO-9420069 A1 | 9/1994 |
| WO | WO-0103737 A1 | 1/2001 |
| WO | WO-0164751 A3 | 12/2001 |
| WO | WO-0243660 A3 | 6/2003 |
| WO | WO-2009140659 A2 | 11/2009 |
| WO | WO-2009140661 A1 | 11/2009 |
| WO | WO-2010108153 A2 | 9/2010 |
| WO | WO-2012169822 A2 | 12/2012 |
| WO | WO-2012170977 A1 | 12/2012 |
| WO | WO-2014059213 A1 | 4/2014 |
| WO | WO2015/006744 * | 1/2015 |
| WO | WO-2015006744 A1 | 1/2015 |
| WO | WO-2018013483 A1 | 1/2018 |

OTHER PUBLICATIONS

Coleman P. M. (Research in Immunology, 145:33-36 (Year: 1994).*
Wu et al., J Mol Bio vol. 368, pp. 652-665 (Year: 2007).*
Zang et al., J. Am. Chem. Soc. 2015, 137, 1,38-41, pub Dec. 10, 2014 (Year: 2015).*
Wu et al. JMB 2005, vol. 350, pp. 126-144). (Year: 2005).*
Becker, J.C. et al. An antibody-interleukin 2 fusion protein overcomes tumor heterogeneity by induction of a cellular immune response. Proc. Natl. Acad. Sci. UA 93:7826-7831 (Jul. 1996).
Eppstein et al. Biological activity of liposome-encapsulated murine interferon gamma is mediated by a cell membrane receptor. Proc. Natl. Acad. Sci. USA, 82: 3688-3692 (1985).
Gillies, Stephen D. A new platform for constructing antibody-cytokine fusion proteins (immunocytokines) with improved biological properties and adaptable cytokine activity. Protein Engineering, Design & Selection 26(10):561-569 (2013); Epub Sep. 10, 2013.
Holzer, W. et al. A Fusion Protein of IL-8 and a FAB Antibody Fragment Binds to IL-8 Receptors and Induces Neutrophil Activation. CYTOKINE, 8(3):214-221 (Mar. 1996).
International Application No. PCT/US16/65779 International Search Report and Written Opinion dated May 31, 2017.
International Application No. PCT/US2015/034533 International Preliminary Report on Patentability dated Dec. 15, 2016.
International Application No. PCT/US2016/065779 International Preliminary Report on Patentability dated Jun. 21, 2018.
Langer et al. Biocompatibility of polymeric delivery systems for macromolecules. J Biomed Mater Res 15(2):267-277 (Mar. 1981).
LeFleur, D.W. et al. Monoclonal antibody therapeutics with up to five specificities Funtional enhancement through fusion of target-specific peptides. mAbs 5(2):208-218 (Mar./Apr. 2013).
Lu, D. et al. Construction and Production of an IgG-Like Tetravalent Bispecific Antibody, IgG-Single-Chain Fv Fusion. Human Monoclonal Antibodies: Methods and Protocols, Methods in Molecular Biology, vol. 1060, Chapter 11, pp. 185-213 (2014).
Pardridge, W.M. and Boado, R. Pharmacokinetics and Safety in Rhesus Monkeys of a Monoclonal Antibody-GDNF Fusion Protein for Targeted Blood-Brain Barrier Delivery. Pharmaceutical Research, 26(10):2227-2236 (Oct. 2009).
Reusch et al. Effect of tetravalent bispecific CD19xCD3 recombinant antibody construct and CD28 costimulation on lysis of malignant B cells from patients with chronic lymphocytic leukemia by autologous T cells. Int J Cancer 112(3):509-518 (2004).
Saini, et al. Exceptionally long CDR3H region with multiple cysteine residues in functional bovine IgM antibodies. Eur J Immunol. Aug. 1999;29(8):2420-2426.
Schlapschy, et al. Fusion of a recombinant antibody fragment with a homo-amino-acid polymer: effects on biophysical properties and prolonged plasma half-life. Protein Eng Des Sel. Jun. 2007;20(6):273-84. Epub Jun. 26, 2007.
Sidman et al. Controlled release of macromolecules and pharmaceuticals from synthetic polypeptides based on glutamic acid. Biopolymers, 22(1):547-556 (Jan. 1983).
Vugmeyster, Y. et al. Pharmacokinetics of anti-IL17A and anti-IL22 peptide-antibody bispecific genetic fusions in mice. International Immunopharmacology 18:225-227 (2014).
Wang, et al., Reshaping Antibody Diversity. Cell 153: 1379-1393 (2013).
Weidle, U.H. et al. Genetically Engineered Fusion Proteins for Treatment of Cancer. Cancer Genomics & Proteomics 9:357-372 (2012).
Wu; et al., "Development of Motavizumab, an Ultra-potent Antibody for the Prevention of Respiratory Syncytial Virus Infection in the Upper and Lower Respiratory Track", JMP Science Direct, Feb. 24, 2007, 368, 652-665.
Wu, et al. Simultaneous targeting of multiple disease mediators by a dual-variable-domain immunoglobulin. Nat Biotechnol. Nov. 2007;25(11):1290-7. Epub Oct. 14, 2007.
Wu; et al., "Ultra-potent Antibodies Against Respiratory Syncytial Virus: Effects of Binding Kinetics and Binding Valence on Viral Neutralization", JMB Science Direct, Apr. 2005, 350, 126-144.
Yang et al. Engineering a long-acting, potent GLP-1 analog for microstructure-based transdermal delivery. PNAS 113(15):4140-4145 (2016).
"Ye, T. et al. High-Level expression and characterization of an anti-VEGF165 single-chain variable fragment (scFv) by small ubiquitin-related modifier fusion in *Escherichia coli*. Appl. Microbiol. Biotechnol. 81:311-317 (2008)".
Yi, K.S. et al. Expression System for Enhanced Green Flourescence Protein Conjugated Recombinant Antibody Fragment. Hybridoma and Hybridomics, 23(5):279-286 (2004).
Zhang, et al. An Antibody with a Variable-Region Coiled-Coil Knob: Domain. Angew. Chem. Int. Ed. 53: 132-135 (2014).
Zhang, et al., Functional Antibody CDR3 fusion proteins with enhanced pharmacological properties. Angew. Chem. Int. Ed. 52: 8295-8298 (2013).

* cited by examiner

RELAXIN IMMUNOGLOBULIN FUSION PROTEINS AND METHODS OF USE

CROSS-REFERENCE

This application is a U.S. National Stage entry of International Application No. PCT/US2016/065779, filed Jul. 23, 2013; which claims the benefit of U.S. Provisional Application No. 62/265,344, filed Dec. 9, 2015, which is incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Nov. 8, 2018, is named 41135-756-831-SEQ.txt and is 92.4 KB in size.

BACKGROUND OF THE INVENTION

Relaxin is expressed mainly in the corpus luteum, in both pregnant and non-pregnant females, rising to a peak within approximately 14 days of ovulation, and then declining in the absence of pregnancy, resulting in menstruation. During the first trimester of pregnancy, levels rise and additional relaxin is produced by the decidua. Relaxin expression peaks during the 14 weeks of the first trimester and at delivery. It is known to mediate the hemodynamic changes that occur during pregnancy, such as increased cardiac output, increased renal blood flow, and increased arterial compliance. It also relaxes other pelvic ligaments and softens the pubic symphysis. In males, relaxin enhances motility of sperm in semen.

Outside the reproductive system, relaxin affects collagen metabolism, inhibiting collagen synthesis and enhancing its breakdown by increasing matrix metalloproteinases. Relaxin also enhances angiogenesis and is a potent renal vasodilator.

Relaxin interacts with the relaxin receptor LGR7 (RXFP1) and LGR8 (RXFP2), which belong to the G protein-coupled receptor superfamily. Relaxin receptors have been found in the heart, smooth muscle, the connective tissue, and central and autonomous nervous system.

SUMMARY OF THE INVENTION

Disclosed herein are relaxin immunoglobulin fusion proteins and methods of using the same for the treatment of various diseases and conditions. The disease or condition may be acute, for example, acute heart failure, acute coronary syndrome with cardiac dysfunction, ischemia reperfusion associated with solid organ transplantation, cardiopulmonary bypass, ischemic stroke, or preeclampsia. The disease or condition may be chronic, for example, diffuse scleroderma, chronic heart failure, diabetic nephropathy, cirrhosis, portal hypertension, atrial fibrillation, cardiac fibrosis, and diabetic wound healing. The methods and compositions may also be used to improve the delivery of a relaxin peptide to target cells, tissues, or tumors.

In one aspect, provided herein are compositions comprising: (a) relaxin therapeutic peptide comprising a relaxin B chain connected via a peptide linker to a relaxin A chain; and (b) an antibody variable domain comprising SEQ ID NO: 75: SMITX(1)X(2)X(3)FDV, wherein X(1) is selected from F, A, G, and P; X(2) is selected from G, A, S, T, and P; and X(3) is selected from G, A, V, L, and P; and wherein the relaxin therapeutic peptide is connected to the amino-terminus of the antibody variable domain with a connecting peptide. In some embodiments, the antibody variable domain is modified from a heavy chain variable domain of a palivizumab antibody comprising SEQ ID NO: 74, and the composition exhibits reduced binding to RSV-F as compared to the palivizumab antibody. In some embodiments, X(1) is F. In some embodiments, X(1) is A. In some embodiments, X(1) is G. In some embodiments, X(1) is P. In some embodiments, X(2) is G. In some embodiments, X(2) is A. In some embodiments, X(2) is S. In some embodiments, X(2) is T. In some embodiments, X(2) is P. In some embodiments, X(3) is G. In some embodiments, X(3) is A. In some embodiments, X(3) is V. In some embodiments, X(3) is L. In some embodiments, X(3) is P. In some embodiments, the antibody variable domain further comprises one or more of SEQ ID NOS: 72 and 73. In some embodiments, the composition further comprises an antibody sequence comprising one or more of SEQ ID NOS: 89 or 90. In some embodiments, the composition further comprises an antibody sequence comprising SEQ ID NO: 92 (FQX(4)X(5)GYPFT), wherein X(4) is selected from G, Y, F, W, P, L, V, and A; and X(5) is selected from S, N, G, A, V, L, and P. In some embodiments X(4) is G. In some embodiments X(4) is Y. In some embodiments X(4) is F. In some embodiments X(4) is W. In some embodiments X(4) is P. In some embodiments X(4) is L. In some embodiments X(4) is V. In some embodiments X(4) is A. In some embodiments, X(5) is S. In some embodiments, X(5) is N. In some embodiments, X(5) is G. In some embodiments, X(5) is A. In some embodiments, X(5) is V. In some embodiments, X(5) is L. In some embodiments, X(5) is P. In some embodiments, X(4) is Y and X(5) is S. In some embodiments, X(4) is G and X(5) is N. In some embodiments, the relaxin B chain comprises an amino acid sequence of SEQ ID NO: 46. In some embodiments, the relaxin A chain comprises an amino acid sequence of SEQ ID NO: 47. In some embodiments, the peptide linker comprises at least about 4 consecutive amino acids comprising any combination of G and S amino acids. In some embodiments, the connecting peptide comprises at least about 4 consecutive amino acids comprising any combination of G and S amino acids. In some embodiments, the composition further comprises an Fc region of an antibody and the Fc region comprises one or more mutations to reduce antibody-dependent cellular cytotoxicity. In some embodiments, the Fc region comprises an amino acid sequence at least about 90% identical to SEQ ID NO: 98.

In one aspect, provided herein are compositions comprising: (a) relaxin therapeutic peptide comprising a relaxin B chain connected via a peptide linker to a relaxin A chain; and (b) an antibody variable domain comprising a modified heavy chain variable domain of a palivizumab antibody comprising SEQ ID NO: 74 having reduced binding to RSV-F as compared to the palivizumab antibody; wherein the relaxin therapeutic peptide is connected to the amino-terminus of the antibody variable domain with a connecting peptide. In some embodiments, the antibody variable domain comprises SEQ ID NO: 75: SMITX(1)X(2)X(3) FDV, wherein X(1) is selected from F, A, G, and P; X(2) is selected from G, A, S, T, and P; and X(3) is selected from G, A, V, L, and P. In some embodiments, X(1) is F. In some embodiments, X(1) is A. In some embodiments, X(1) is G. In some embodiments, X(1) is P. In some embodiments, X(2) is G. In some embodiments, X(2) is A. In some embodiments, X(2) is S. In some embodiments, X(2) is T. In some embodiments, X(2) is P. In some embodiments, X(3)

is G. In some embodiments, X(3) is A. In some embodiments, X(3) is V. In some embodiments, X(3) is L. In some embodiments, X(3) is P. In some embodiments, the antibody variable domain further comprises one or more of SEQ ID NOS: 72 and 73. In some embodiments, the composition further comprises an antibody sequence comprising one or more of SEQ ID NOS: 89 or 90. In some embodiments, the composition further comprises an antibody sequence comprising SEQ ID NO: 92 (FQX(4)X(5)GYPFT), wherein X(4) is selected from G, Y, F, W, P, L, V, and A; and X(5) is selected from S, N, G, A, V, L, and P. In some embodiments, X(4) is Y and X(5) is S. In some embodiments X(4) is Y. In some embodiments X(4) is F. In some embodiments X(4) is W. In some embodiments X(4) is P. In some embodiments X(4) is L. In some embodiments X(4) is V. In some embodiments X(4) is A. In some embodiments, X(5) is S. In some embodiments, X(5) is N. In some embodiments, X(5) is G. In some embodiments, X(5) is A. In some embodiments, X(5) is V. In some embodiments, X(5) is L. In some embodiments, X(5) is P. In some embodiments, X(4) is G and X(5) is N. In some embodiments, the relaxin B chain comprises an amino acid sequence of SEQ ID NO: 46. In some embodiments, the relaxin A chain comprises an amino acid sequence of SEQ ID NO: 47. In some embodiments, the peptide linker comprises at least about 4 consecutive amino acids comprising any combination of G and S amino acids. In some embodiments, the connecting peptide comprises at least about 4 consecutive amino acids comprising any combination of G and S amino acids. In some embodiments, the composition further comprises an Fc region of an antibody and the Fc region comprises one or more mutations to reduce antibody-dependent cellular cytotoxicity. In some embodiments, the Fc region comprises an amino acid sequence at least about 90% identical to SEQ ID NO: 98.

In another aspect, provided herein are methods of treating a disease or condition in an individual in need thereof. In some embodiments, the method comprises administering to the individual a composition comprising a relaxin therapeutic peptide; wherein the composition is intravenously or subcutaneously administered in less than or equal to 6 hours. In some embodiments, the composition is administered in less than or equal to 4, 3, 2 or 1 hours. In some embodiments, the composition is administered during a treatment period of about one day to about 1 week. In some embodiments, the composition is administered about 1, 2, 3, 4, 5, 6 or 7 times. In some embodiments, the disease or condition is selected from acute heart failure, acute coronary syndrome with cardiac dysfunction, ischemia reperfusion associated with solid organ transplantation, cardiopulmonary bypass, ischemic stroke, or preeclampsia. In some embodiments, the disease or condition is solid organ transplantation and the organ is selected from the lung, kidney, liver and heart. In some embodiments, the composition is administered during a treatment period lasting at least about one week. In some embodiments, the composition is administered twice per week, once per week, four times per month, three times per month, twice per month, once per month, or once per every two months. In some embodiments, the disease or condition is selected from diffuse scleroderma, chronic heart failure, diabetic nephropathy, cirrhosis, portal hypertension, atrial fibrillation, cardiac fibrosis, and diabetic wound healing.

In another aspect, provided herein are methods of treating a disease or condition in an individual in need thereof. In some embodiments, the method comprises administering to the individual a composition comprising a relaxin therapeutic peptide; wherein the composition is administered to the eye. In some embodiments, the composition is administered in a liquid solution or suspension. In some embodiments, the composition comprises a relaxin therapeutic peptide connected to an amino-terminus of an antibody variable domain via a connecting peptide. In some embodiments, the relaxin polypeptide comprises a relaxin B chain and a relaxin A chain connected by a peptide linker. In some embodiments, the relaxin polypeptide comprises (a) relaxin therapeutic peptide comprising a relaxin B chain connected via a peptide linker to a relaxin A chain; and (b) an antibody variable domain comprising SEQ ID NO: 75: SMITX(1)X(2)X(3)FDV, wherein X(1) is selected from F, A, G, and P; X(2) is selected from G, A, S, T, and P; and X(3) is selected from G, A, V, L, and P; and wherein the relaxin therapeutic peptide is connected to the amino-terminus of the antibody variable domain with a connecting peptide. In some embodiments, the antibody variable domain is modified from a heavy chain variable domain of a palivizumab antibody comprising SEQ ID NO: 74, and the composition exhibits reduced binding to RSV-F as compared to the palivizumab antibody. In some embodiments, X(1) is F. In some embodiments, X(1) is A. In some embodiments, X(1) is G. In some embodiments, X(1) is P. In some embodiments, X(2) is G. In some embodiments, X(2) is A. In some embodiments, X(2) is S. In some embodiments, X(2) is T. In some embodiments, X(2) is P. In some embodiments, X(3) is G. In some embodiments, X(3) is A. In some embodiments, X(3) is V. In some embodiments, X(3) is L. In some embodiments, X(3) is P. In some embodiments, X(2) is G. In some embodiments, X(2) is A. In some embodiments, X(2) is G. In some embodiments, the antibody variable domain further comprises one or more of SEQ ID NOS: 72 and 73. In some embodiments, the relaxin polypeptide further comprises an antibody sequence comprising one or more of SEQ ID NOS: 89 or 90. In some embodiments, the relaxin polypeptide further comprises an antibody sequence comprising SEQ ID NO: 92 (FQX(4)X(5)GYPFT), wherein X(4) is selected from G, Y, F, W, P, L, V, and A; and X(5) is selected from S, N, G, A, V, L, and P. In some embodiments X(4) is Y. In some embodiments X(4) is F. In some embodiments X(4) is W. In some embodiments X(4) is P. In some embodiments X(4) is L. In some embodiments X(4) is V. In some embodiments X(4) is A. In some embodiments, X(5) is S. In some embodiments, X(5) is N. In some embodiments, X(5) is G. In some embodiments, X(5) is A. In some embodiments, X(5) is V. In some embodiments, X(5) is L. In some embodiments, X(5) is P. In some embodiments, X(4) is Y and X(5) is S. In some embodiments, X(4) is G and X(5) is N. In some embodiments, the relaxin B chain comprises an amino acid sequence of SEQ ID NO: 46. In some embodiments, the relaxin A chain comprises an amino acid sequence of SEQ ID NO: 47. In some embodiments, the peptide linker comprises at least about 4 consecutive amino acids comprising any combination of G and S amino acids. In some embodiments, the connecting peptide comprises at least about 4 consecutive amino acids comprising any combination of G and S amino acids. In some embodiments, the relaxin polypeptide further comprises an Fc region of an antibody and the Fc region comprises one or more mutations to reduce antibody-dependent cellular cytotoxicity. In some embodiments, the Fc region comprises an amino acid sequence at least about 90% identical to SEQ ID NO: 98.

Further provided herein are methods of treating cardiovascular disease in an individual in need thereof, comprising administering an effective amount of a relaxin immunoglobulin fusion protein described herein to reduce at least one symptom of the cardiovascular disease. In some embodiments, the cardiovascular disease is selected from one or more of the group consisting of acute heart failure, congestive heart failure, compensated heart failure, decompensated heart failure, acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure, fibrosis of the heart, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, metabolic syndrome, dyslipemia, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, and hypercholesterolemia. In some embodiments, cardiovascular disease is heart failure. In some embodiments, the symptom is selected from one or more of the group consisting of chest pain, shortness of breath, pain, numbness, weakness, rapid pulse, slow pulse, lightheadedness, dizziness, swelling of the limbs, and fainting.

Also provided herein are methods of treating fibrosis in an individual in need thereof, comprising administering an effective amount of a relaxin immunoglobulin fusion protein provided herein sufficient to reduce at least one symptom of the fibrosis. In some embodiments, the fibrosis is selected from one or more of the group consisting of pulmonary fibrosis, idiopathic pulmonary fibrosis, cystic fibrosis, cirrhosis, endomyocardial fibrosis, myocardial infarction, atrial fibrosis, mediastinal fibrosis, myelofibrosis, retroperitoneal fibrosis, progressive massive fibrosis, nephrogenic systemic fibrosis, Crohn's disease, keloid, scleroderma/systemic sclerosis, arthrofibrosis, Peyronie's disease, Dupuytren's contracture, and adhesive capsulitis. Also provided herein are methods of treating acute heart failure, acute coronary syndrome with cardiac dysfunction, ischemia reperfusion associated with solid organ transplantation, cardiopulmonary bypass, ischemic stroke, preeclampsia, diffuse scleroderma, chronic heart failure, diabetic nephropathy, cirrhosis, portal hypertension, atrial fibrillation, cardiac fibrosis, diabetic wound healing, or a combination thereof, comprising administering an effective amount of a relaxin immunoglobulin fusion protein provided herein.

Also provided herein, are genetic constructs comprising a polynucleotide encoding a relaxin immunoglobulin fusion protein provided herein. Further provided herein are expression vector comprising the genetic constructs disclosed herein. Further provided herein are mammalian expression hosts comprising the expression vectors disclosed herein. Further provided herein are methods of producing a relaxin immunoglobulin fusion protein comprising: transfecting the expression vector into a mammalian cell culture; growing the cell culture in an expression medium at a controlled temperature and percentage CO2; and harvesting the secreted immunoglobulin fusion protein.

BRIEF DESCRIPTION OF THE DRAWINGS

The foregoing summary, as well as the following detailed description of the disclosure, will be better understood when read in conjunction with the appended figures. It should be understood, however, that the disclosure is not limited to the precise examples shown. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1A:
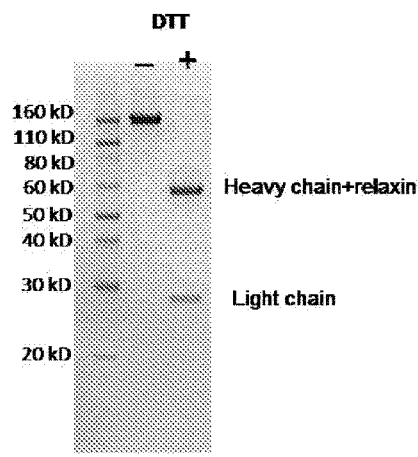
FIG. 1A, FIG. 1B, and FIG. 1C show SDS-PAGE gels of purified palivizumab-relaxin fusion proteins.

Relaxin amino-terminal palivizumab fusions with reduced binding to respiratory syncytial virus (RSV) proteins which have a relaxin peptide fused to the amino-terminus of a palivizumab heavy chain polypeptide are useful in treating diseases responsive to relaxin peptide. Reducing binding to RSV proteins is achieved by mutating amino acid residues in the CDR portions of the palivizumab amino acid sequence. Further therapeutic value is obtained by reducing ADCC elicited by the palivizumab by mutating amino acid residues in the Fc portion of the palivizumab amino acid sequence.

Disclosed herein are amino-terminal immunoglobulin fusion proteins comprising a relaxin peptide, and methods of use for the treatment of a disease or condition responsive to a relaxin peptide. According to one feature of the subject matter described herein, an amino-terminal immunoglobulin fusion protein comprises (a) a first immunoglobulin region;

and (b) a relaxin peptide connected to the amino terminus of the first immunoglobulin region with a connecting peptide. The first immunoglobulin region may be part of an immunoglobulin heavy chain, and the immunoglobulin fusion protein further comprises a second immunoglobulin region of an immunoglobulin light chain. As used herein, an immunoglobulin region may include a variable domain such that the relaxin peptide is connected to the amino-terminus of a variable domain of the immunoglobulin region. The first and/or second immunoglobulin region may comprise part of an antibody variable domain that does not form a binding site specific for a human antigen. In some cases, the antibody variable domain is a palivizumab variable domain, or a variable domain modified from a palivizumab variable domain. The variable domain may be modified from palivizumab to attenuate or eliminate RSV binding.

Exemplary amino-terminal immunoglobulin fusion proteins are depicted in Formulas I-XXXII, wherein T is a therapeutic peptide or a portion of a therapeutic peptide, C is a connecting peptide, A is an immunoglobulin region, P is a protease site, L is a linker, and I is an internal linker. The therapeutic peptide may be a relaxin peptide comprising one or a combination of relaxin B chain, relaxin A chain, and C-peptide or linker peptide.

| Formula | Immunoglobulin fusion protein |
|---|---|
| I | $T^1$-$A^1$ |
| II | $T^1$-C-$A^1$ |
| III | $T^1$-C-$P^1$-$A^1$ |
| IV | $T^1$-$P^1$-C-$A^1$ |
| V | $T^1$-$L^1$-I-$L^2$-$T^2$-$A^1$ |
| VI | $T^1$-$L^1$-I-$L^2$-$T^2$-C-$A^1$ |
| VII | $T^1$-$L^1$-$T^2$-$L^2$-$T^3$-$A^1$ |
| VIII | $T^1$-$L^1$-$T^2$-$L^2$-$T^3$-C-$A^1$ |
| IX | $T^1$-$P^1$-I-$P^2$-$T^2$-$A^1$ |
| X | $T^1$-$P^1$-I-$P^2$-$T^2$-C-$A^1$ |
| XI | $T^1$-$P^1$-$T^2$-$P^2$-$T^3$-$A^1$ |
| XII | $T^1$-$P^1$-$T^2$-$P^2$-$T^3$-C-$A^1$ |
| XIII | $T^1$-$P^1$-$L^1$-I-$L^2$-$P^2$-$T^2$-$A^1$ |
| XIV | $T^1$-$P^1$-$L^1$-I-$L^2$-$P^2$-$T^2$-C-$A^1$ |
| XV | $T^1$-$P^1$-$L^1$-$T^2$-$L^2$-$P^2$-$T^3$-$A^1$ |
| XVI | $T^1$-$P^1$-$L^1$-$T^2$-$L^2$-$P^2$-$T^3$-C-$A^1$ |
| XVII | $T^1$-$L^1$-$P^1$-$T^2$-$A^1$ |
| XVIII | $T^1$-$P^1$-$L^1$-$T^2$-$A^1$ |
| XIX | $T^1$-$P^1$-$L^1$-$T^2$-C-$A^1$ |
| XX | $T^1$-$P^1$-$P^2$-$P^3$-$T^2$-$A^1$ |
| XXI | $T^1$-$P^1$-I-$P^2$-$P^3$-$T^2$-$A^1$ |
| XXII | $T^1$-$P^1$-I-$T^2$-$A^1$ |
| XXIII | $T^1$-$P^1$-I-$T^2$-C-$A^1$ |
| XXIV | $T^1$-$P^1$-L-$P^2$-$P^3$-$T^2$-$A^1$ |
| XXV | $T^1$-$P^1$-L-$P^2$-$P^3$-$T^2$-C-$A^1$ |
| XXVI | $T^1$-$P^1$-$T^2$-$P^2$-$P^3$-$T^3$-$A^1$ |
| XXVII | $T^1$-$P^1$-$T^2$-$P^2$-$P^3$-$T^3$-C-$A^1$ |
| XXVIII | $T^1$-L-$T^2$-$A^1$ |
| XXIX | $T^1$-L-$T^2$-C-$A^1$ |
| XXX | $T^1$-I-$T^2$-$A^1$ |
| XXXI | $T^1$-I-$T^2$-C-$A^1$ |
| XXXII | $T^1$-P-$T^2$-C-$A^1$ |

Further disclosed herein are methods of treating a disease or condition in a subject in need thereof. Generally, the method comprises administering to the subject an amino-terminal immunoglobulin fusion protein comprising a therapeutic peptide such as a relaxin peptide attached to the amino terminus of an immunoglobulin region. In some embodiments, an immunoglobulin fusion protein having the formula of I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, or any modification, portions, or additions thereof is administered to a patient. In some embodiments, one or more of the immunoglobulin fusion proteins I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, or XXXII, further comprising a second immunoglobulin region, is administered to a patient.

Further disclosed herein are methods of improving the delivery of a therapeutic peptide. The methods may involve generation of an amino-terminal immunoglobulin fusion protein from a genetic construct. In some embodiments, the immunoglobulin fusion protein is recombinantly produced from a genetic construct encoding the immunoglobulin fusion protein. In some embodiments, the construct is expressed in vitro using standard mammalian cell culture techniques. In some embodiments, one construct encoding a therapeutic peptide connected to the amino-terminus of a first immunoglobulin region is co-expressed with a second construct comprising a second immunoglobulin region, to produce a recombinant immunoglobulin fusion protein. In some embodiments, a construct encoding a protease is co-expressed with an immunoglobulin fusion protein. The method may further comprise generating immunoglobulin genetic fusion constructs comprising one or more connecting peptides, internal linkers, linkers, and/or proteolytic cleavage sites.

Before the present methods and compositions are described, it is to be understood that this disclosure is not limited to a particular method or composition described, and as such may vary. It is also to be understood that the terminology used herein is for the purpose of describing particular embodiments only, and is not intended to be limiting. Examples are put forth so as to provide those of ordinary skill in the art with a disclosure and description of how to make and use the immunoglobulin fusion proteins provided herein, and are not intended to limit the scope of what the inventors regard as their invention nor are they intended to represent that the provided experiments encompass all of the experiments performed. Efforts have been made to ensure accuracy with respect to numbers used but some experimental errors and deviations should be accounted for.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Any recited combination of amino acid sequences can have the order recited, or any other order which is logically possible. As a non-limiting example, an immunoglobulin fusion protein comprising an insulin therapeutic peptide, T, and an immunoglobulin region, A, includes, for example and without limitation: T-A, A-T, T-A-T, and A-T-A.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

Relaxin Immunoglobulin Fusion Proteins

Various insulin immunoglobulin fusion proteins disclosed herein comprise a first immunoglobulin region and a relaxin therapeutic peptide, wherein the relaxin therapeutic peptide, or an amino acid sequence thereof, is connected to an amino terminus of the first immunoglobulin region. In various instances, the insulin immunoglobulin fusion proteins further comprise a second immunoglobulin region. The immunoglobulin region (first and/or second) may be any portion, in part or whole, of an immunoglobulin.

The immunoglobulin region may comprise an entire immunoglobulin molecule or any polypeptide comprising a fragment of an immunoglobulin including, but not limited to, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any portion or combination thereof. In some embodiments, an immunoglobulin heavy chain may comprise an entire heavy chain or a portion of a heavy chain. For example, a variable domain or region thereof derived from a heavy chain may be referred to as a heavy chain or a region of a heavy chain. In some embodiments, an immunoglobulin light chain may comprise an entire light chain or a portion of a light chain. For example, a variable domain or region thereof derived from a light chain may be referred to as a light chain or a region of a light chain. The immunoglobulin region may be bispecific or trispecific. A single domain immunoglobulin includes, but is not limited to, a single monomeric variable immunoglobulin domain. The single domain immunoglobulin may be a shark variable new antigen receptor immunoglobulin fragment (VNAR). The immunoglobulin may be derived from any type known to one of skill in the art including, but not limited to, IgA, IgD, IgE, IgG, IgM, IgY, IgW. The immunoglobulin region may be a glycoprotein. The immunoglobulin region may comprise one or more functional units, including but not limited to, 1, 2, 3, 4, and 5 units. The immunoglobulin region may comprise one or more units connected by one or more disulfide bonds. The immunoglobulin region may comprise one or more units connected by a peptide linker, for example, a scFv immunoglobulin. The immunoglobulin may be a recombinant immunoglobulin including immunoglobulins with amino acid mutations, substitutions, and/or deletions. The immunoglobulin may be a recombinant immunoglobulin comprising chemical modifications. The immunoglobulin may comprise a whole or part of an immunoglobulin-drug conjugate. The immunoglobulin may comprise a small molecule. The immunoglobulin may comprise a whole or part of an immunoglobulin-drug conjugate comprising a small molecule. The immunoglobulin may be from a mammalian source. The immunoglobulin may be a chimeric immunoglobulin. The immunoglobulin region may be derived in whole or in part from an engineered immunoglobulin or recombinant immunoglobulin. The immunoglobulin may be from a humanized, human engineered or fully human immunoglobulin. The mammalian immunoglobulin may be a bovine immunoglobulin. The mammalian immunoglobulin may be a human immunoglobulin. The mammalian immunoglobulin may be a murine immunoglobulin. The mammalian immunoglobulin may be a non-human primate immunoglobulin. The immunoglobulin may be an avian immunoglobulin. The immunoglobulin may be a shark immunoglobulin.

The immunoglobulin heavy chain fusion may comprise an amino acid sequence that is based on or derived from any one of SEQ ID NOs: 13-16, 20-22. The immunoglobulin heavy chain fusion may comprise an amino acid sequence that is at least about 50% homologous to any one of SEQ ID NOs: 13-16, 20-22. The immunoglobulin heavy chain fusion may comprise an amino acid sequence that is at least about 60%, 65%, 70%, 75%, 80%, 85%, 90%, 95%, or 97% homologous to any one of SEQ ID NOs: 13-16, 20-22. The immunoglobulin heavy chain fusion may comprise an amino acid sequence that is at least about 70% homologous to any one of SEQ ID NOs: 13-16, 20-22. The immunoglobulin heavy chain fusion may comprise an amino acid sequence that is at least about 80% homologous to any one of SEQ ID NOs: 13-16, 20-22. The immunoglobulin heavy chain fusion may comprise an amino acid sequence that is at least about 50% identical to any one of SEQ ID NOs: 13-16, 20-22. The immunoglobulin heavy chain fusion may comprise an amino acid sequence that is at least about 60%, 65%, 70%, 75%, 80%, 85%, 90%, 95%, or 97% identical to any one of SEQ ID NOs: 13-16, 20-22. The immunoglobulin heavy chain fusion may comprise an amino acid sequence that is at least about 70% identical to any one of SEQ ID NOs: 13-16, 20-22. The immunoglobulin heavy chain fusion may comprise an amino acid sequence that is at least about 80% identical to any one of SEQ ID NOs: 13-16, 20-22. The immunoglobulin heavy chain fusion may comprise an amino acid sequence that is 100% identical to any one of SEQ ID NOs: 13-16, 20-22. The immunoglobulin light chain may comprise an amino acid sequence that is based on or derived from any one of SEQ ID NOs: 9-12. The immunoglobulin light chain may comprise an amino acid sequence that is at least about 50% homologous to any one of SEQ ID NOs: 9-12. The immunoglobulin light chain may comprise an amino acid sequence that is at least about 60%, 65%, 70%, 75%, 80%, 85%, 90%, 95%, or 97% homologous to any one of SEQ ID NOs: 9-12. The immunoglobulin light chain may comprise an amino acid sequence that is at least about 70% homologous to any one of SEQ ID NOs: 9-12. The immunoglobulin light chain may comprise an amino acid sequence that is at least about 80% homologous to any one of SEQ ID NOs: 9-12. The immunoglobulin light chain may comprise an amino acid sequence that is at least about 50% identical to any one of SEQ ID NOs: 9-12. The immunoglobulin light chain may comprise an amino acid sequence that is at least about 60%, 65%, 70%, 75%, 80%, 85%, 90%, 95%, or 97% identical to any one of SEQ ID NOs: 9-12. The immunoglobulin light chain may comprise an amino acid sequence that is at least about 70% identical to any one of SEQ ID NOs: 9-12. The immunoglobulin light chain may comprise an amino acid sequence that is at least about 80% identical to any one of SEQ ID NOs: 9-12. The immunoglobulin light chain may comprise an amino acid sequence that is 100% identical to any one of SEQ ID NOs: 9-12.

The immunoglobulin heavy chain fusion may comprise an amino acid sequence that is based on or derived from SEQ ID NO: 22. The immunoglobulin heavy chain fusion may comprise an amino acid sequence that is at least about 50% homologous to SEQ ID NO: 22. The immunoglobulin heavy chain fusion may comprise an amino acid sequence that is at least about 60%, 65%, 70%, 75%, 80%, 85%, 90%, 95%, or 97% homologous to SEQ ID NO: 22. The immunoglobulin heavy chain fusion may comprise an amino acid sequence that is at least about 70% homologous to SEQ ID NO: 22. The immunoglobulin heavy chain fusion may comprise an amino acid sequence that is at least about 80% homologous to SEQ ID NO: 22. The immunoglobulin heavy chain fusion may comprise an amino acid sequence that is at least about 50% identical to SEQ ID NO: 22. The immunoglobulin heavy chain fusion may comprise an amino acid sequence that is at least about 60%, 65%, 70%, 75%, 80%, 85%, 90%, 95%, or 97% identical to SEQ ID NO: 22. The immunoglobulin heavy chain fusion may comprise an amino acid sequence that is at least about 70% identical to SEQ ID NO: 22. The immunoglobulin heavy chain fusion may comprise an amino acid sequence that is at least about 80% identical to SEQ ID NO: 22. The immunoglobulin heavy chain fusion may comprise an amino acid sequence that is 100% identical to SEQ ID NO: 22. The immunoglobulin light chain may comprise an amino acid sequence that is based on or derived from SEQ ID NO: 12. The immunoglobulin light chain may comprise an amino acid sequence that is at least about 50% homologous to SEQ ID NO: 12. The immunoglobulin light chain may comprise an amino acid sequence that is at least about 60%, 65%, 70%, 75%, 80%, 85%, 90%, 95%, or 97% homologous to SEQ ID NO: 12. The immunoglobulin light chain may comprise an amino acid sequence that is at least about 70% homologous to SEQ ID NO: 12. The immunoglobulin light chain may comprise an amino acid sequence that is at least about 80% homologous to SEQ ID NO: 12. The immunoglobulin light chain may comprise an amino acid sequence that is at least about 50% identical to SEQ ID NO: 12. The immunoglobulin light chain may comprise an amino acid sequence that is at least about 60%, 65%, 70%, 75%, 80%, 85%, 90%, 95%, or 97% identical to SEQ ID NO: 12. The immunoglobulin light chain may comprise an amino acid sequence that is at least about 70% identical to SEQ ID NO: 12. The immunoglobulin light chain may comprise an amino acid sequence that is at least about 80% identical to SEQ ID NO: 12. The immunoglobulin light chain may comprise an amino acid sequence that is 100% identical to SEQ ID NO: 12.

The immunoglobulin heavy chain fusion may comprise an amino acid sequence comprising 10, 20, 30, 40, 50, 60, 70, 80, 90, 100 or more amino acids based on or derived from any one of SEQ ID NOs: 13-16, 20-22. The immunoglobulin heavy chain fusion may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 13-16, 20-22. The immunoglobulin heavy chain fusion may comprise an amino acid sequence comprising 10 or more amino acids based on or derived from any one of SEQ ID NOs: 13-16, 20-22. The immunoglobulin heavy chain fusion may comprise an amino acid sequence comprising 50 or more amino acids based on or derived from any one of SEQ ID NOs: 13-16, 20-22. The immunoglobulin heavy chain fusion may comprise an amino acid sequence comprising 100 or more amino acids based on or derived from any one of SEQ ID NOs: 13-16, 20-22. The immunoglobulin heavy chain fusion may comprise an amino acid sequence comprising 200 or more amino acids based on or derived from any one of SEQ ID NOs: 13-16, 20-22. The amino acids may be consecutive. Alternatively, or additionally, the amino acids are nonconsecutive. In some embodiments, the immunoglobulin heavy chain fusion may comprise amino acids derived from any one of SEQ ID NOs: 13-16, 20-22 and amino acids not derived from any one of SEQ ID NOs: 13-16, 20-22. In some embodiments, the immunoglobulin heavy chain fusion may comprise amino acids derived from one or more of SEQ ID NOs: 13-16, 20-22 and amino acids not derived from any one of SEQ ID NOs: 13-16, 20-22. In some embodiments, the immunoglobulin heavy chain fusion comprises amino acids derived from 1, 2, 3, 4, or 5 of SEQ ID NOs: 13-16, 20-22.

The immunoglobulin heavy chain fusion may be encoded by a nucleotide sequence that is based on or derived from any one of SEQ ID NOs: 5-8, 17-19. The immunoglobulin heavy chain fusion may be encoded by a nucleotide sequence that is at least about 50% homologous to any one of SEQ ID NOs: 5-8, 17-19. The immunoglobulin heavy chain fusion may be encoded by a nucleotide sequence that is at least about 60%, 65%, 70%, 75%, 80%, 85%, 90%, 95%, or 97% homologous to any one of SEQ ID NOs: 5-8, 17-19. The immunoglobulin heavy chain fusion may be encoded by a nucleotide sequence that is at least about 70% homologous to any one of SEQ ID NOs: 5-8, 17-19. The immunoglobulin heavy chain fusion may be encoded by a nucleotide sequence that is at least about 80% homologous to any one of SEQ ID NOs: 5-8, 17-19. The immunoglobulin heavy chain fusion may be encoded by a nucleotide sequence that is at least about 50% identical to any one of SEQ ID NOs: 5-8, 17-19. The immunoglobulin heavy chain fusion may be encoded by a nucleotide sequence that is at least about 60%, 65%, 70%, 75%, 80%, 85%, 90%, 95%, or 97% identical to any one of SEQ ID NOs: 5-8, 17-19. The immunoglobulin heavy chain fusion may be encoded by a nucleotide sequence that is at least about 70% identical to any one of SEQ ID NOs: 5-8, 17-19. The immunoglobulin heavy chain fusion may be encoded by a nucleotide sequence that is at least about 80% identical to any one of SEQ ID NOs: 5-8, 17-19. The immunoglobulin heavy chain fusion may be encoded by a nucleotide sequence that is 100% identical to any one of SEQ ID NOs: 5-8, 17-19.

The immunoglobulin heavy chain fusion may be encoded by a nucleotide sequence comprising 10, 20, 30, 40, 50, 60, 70, 80, 90, 100 or more nucleotides based on or derived from any one of SEQ ID NOs: 5-8, 17-19. The immunoglobulin heavy chain fusion may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 5-8, 17-19. The immunoglobulin heavy chain fusion may be encoded by a nucleotide sequence comprising 600, 650, 700, 750, 800, 850, 900, 950, 1000 or more nucleotides based on or derived from any one of SEQ ID NOs: 5-8, 17-19. The immunoglobulin heavy chain fusion may be encoded by a nucleotide sequence comprising 1100, 1200, 1300, 1400, 1500 or more nucleotides based on or derived from any one of SEQ ID NOs: 5-8, 17-19. The immunoglobulin heavy chain fusion may be encoded by a nucleotide sequence comprising 100 or more nucleotides based on or derived from any one of SEQ ID NOs: 5-8, 17-19. The immunoglobulin heavy chain fusion may be encoded by a nucleotide sequence comprising 500 or more nucleotides based on or derived from any one of SEQ ID NOs: 5-8, 17-19. The immunoglobulin heavy chain fusion may be encoded by a nucleotide sequence comprising 1000 or more nucleotides based on or derived from any one of SEQ ID NOs: 5-8, 17-19. The immunoglobulin heavy chain fusion may be encoded by a nucleotide sequence comprising 1300 or more nucleotides based on or derived from any one of SEQ ID NOs: 5-8, 17-19. The nucleotides may be consecutive. Alternatively, or additionally, the nucleotides are non-consecutive. In some embodiments, the immunoglobulin heavy chain fusion is encoded by a nucleotide sequence comprising nucleotides derived from any one of SEQ ID NOs: 5-8, 17-19 and nucleotides not derived from any one of SEQ ID NOs: 5-8, 17-19. In some embodiments, the immunoglobulin heavy chain fusion is encoded by a nucleotide sequence comprising nucleotides derived from one or more of SEQ ID NOs: 5-8, 17-19 and nucleotides not derived from any one of SEQ ID NOs: 5-8, 17-19. In some embodiments, the immunoglobulin heavy chain fusion is encoded by a nucleotide sequence derived from 1, 2, 3, 4, or 5 of SEQ ID NOs: 5-8, 17-19.

Immunoglobulin Fusion Proteins

In one feature of the invention, provided herein are immunoglobulin fusion proteins comprising (a) an immunoglobulin light chain fusion, and (b) a second immunoglobulin region derived from an immunoglobulin heavy chain, wherein the immunoglobulin light chain fusion is connected to the second immunoglobulin region by one or more disulfide bonds or a connecting peptide. The immunoglobulin light chain fusion comprises a first therapeutic peptide connected to the amino-terminus of a first immunoglobulin region derived from an immunoglobulin light chain. In some embodiments, the second immunoglobulin region is attached to a non-immunoglobulin region, creating a second immunoglobulin fusion. The non-immunoglobulin region may comprise a second therapeutic peptide. The non-immunoglobulin region may comprise a linker peptide. The non-immunoglobulin region may comprise a proteolytic cleavage site. The second therapeutic peptide may comprise an internal linker. In some embodiments, the second therapeutic peptide is attached to the amino- or carboxyl-terminus of the second immunoglobulin region. In some embodiments, the second therapeutic peptide is attached to one or more internal amino acids of the second immunoglobulin region. In some embodiments, the second therapeutic peptide is attached to amino acids of a loop portion within the second immunoglobulin region. In some embodiments, the therapeutic peptide is attached to the second immunoglobulin region using one or more linker peptides. The immunoglobulin light chain fusion may further comprise one or more additional therapeutic peptides.

In one feature of the invention, provided herein are immunoglobulin fusion proteins comprising (a) an immunoglobulin heavy chain fusion, and (b) a second immunoglobulin region derived from an immunoglobulin light chain, wherein the immunoglobulin heavy chain fusion is connected to the second immunoglobulin region by one or more disulfide bonds or a connecting peptide. The immunoglobulin heavy chain fusion comprises a first therapeutic peptide connected to the amino-terminus of a first immunoglobulin region derived from an immunoglobulin heavy chain. In some embodiments, the second immunoglobulin region is attached to a non-immunoglobulin region, creating a second immunoglobulin fusion. The non-immunoglobulin region may comprise a second therapeutic peptide. The non-immunoglobulin region may comprise a linker peptide. The non-immunoglobulin region may comprise a proteolytic cleavage site. The second therapeutic peptide may comprise an internal linker. In some embodiments, the second therapeutic peptide is attached to the amino- or carboxyl-terminus of the second immunoglobulin region. In some embodiments, the second therapeutic peptide is attached to one or more internal amino acids of the second immunoglobulin region. In some embodiments, the second therapeutic peptide is attached to amino acids of a loop portion within the second immunoglobulin region. In some embodiments, the therapeutic peptide is attached to the second immunoglobulin region using one or more linker peptides. The immunoglobulin heavy chain fusion may further comprise one or more additional therapeutic peptides.

In one feature of the invention, provided herein are immunoglobulin fusion proteins comprising (a) an immunoglobulin light chain fusion, and (b) an immunoglobulin heavy chain fusion. The immunoglobulin light chain fusion comprises a first therapeutic peptide connected to the amino-terminus of a first immunoglobulin region derived from an immunoglobulin light chain. The immunoglobulin heavy chain fusion comprises a first therapeutic peptide connected to the amino-terminus of a first immunoglobulin region derived from an immunoglobulin heavy chain. In some embodiments, the immunoglobulin light chain fusion further comprises one or more additional therapeutic peptides. In some embodiments, the immunoglobulin heavy chain fusion comprises one or more additional therapeutic peptides.

In one feature of the invention, provided herein are immunoglobulin fusion proteins comprising (a) an immunoglobulin light chain fusion, and (b) a second immunoglobulin region, wherein the immunoglobulin light chain fusion comprises a first therapeutic peptide connected to the amino-terminus of a first immunoglobulin region derived from an immunoglobulin light chain. The second immunoglobulin region may be derived from an immunoglobulin heavy chain. The second immunoglobulin region may be derived from an immunoglobulin light chain. The second immunoglobulin region may be connected to one or more non-immunoglobulin regions, creating a second immunoglobulin fusion. The non-immunoglobulin region may comprise a second therapeutic peptide. The non-immunoglobulin region may comprise a linker peptide. The non-immunoglobulin region may comprise a proteolytic cleavage site. The second therapeutic peptide may comprise an internal linker. In some embodiments, the second therapeutic peptide is attached to the amino- or carboxyl-terminus of the second immunoglobulin region. In some embodiments, the second therapeutic peptide is attached to one or more internal amino acids of the second immunoglobulin region. In some embodiments, the second therapeutic peptide is attached to amino acids of a loop portion within the second immunoglobulin region. In some embodiments, the therapeutic peptide is attached to the second immunoglobulin region using one or more linker peptides. The immunoglobulin light chain fusion may further comprise one or more additional therapeutic peptides.

In one feature of the invention, provided herein are immunoglobulin fusion proteins comprising (a) an immunoglobulin heavy chain fusion, and (b) a second immunoglobulin region, wherein the immunoglobulin heavy chain fusion comprises a first therapeutic peptide connected to the amino-terminus of a first immunoglobulin region derived from an immunoglobulin heavy chain. The second immunoglobulin region may be derived from an immunoglobulin heavy chain. The second immunoglobulin region may be derived from an immunoglobulin light chain. The second immunoglobulin region may be connected to one or more non-immunoglobulin regions, creating a second immunoglobulin fusion. The non-immunoglobulin region may comprise a second therapeutic peptide. The non-immunoglobulin region may comprise a linker peptide. The non-immunoglobulin region may comprise a proteolytic cleavage site. The second therapeutic peptide may comprise an internal linker. In some embodiments, the second therapeutic peptide is attached to the amino- or carboxyl-terminus of the second immunoglobulin region. In some embodiments, the second therapeutic peptide is attached to one or more internal amino acids of the second immunoglobulin region. In some embodiments, the second therapeutic peptide is attached to amino acids of a loop portion within the second immunoglobulin region. In some embodiments, the therapeutic peptide is attached to the second immunoglobulin region using one or more linker peptides. The immunoglobulin heavy chain fusion may further comprise one or more additional therapeutic peptides.

In one feature of the invention, provided herein is an immunoglobulin fusion protein comprising a relaxin therapeutic peptide connected to the amino-terminus of a region of an immunoglobulin heavy chain, wherein the immunoglobulin fusion is referred to herein as an immunoglobulin heavy chain fusion. In some embodiments, the immunoglobulin fusion protein further comprises one or more regions of an immunoglobulin light chain, wherein the immunoglobulin heavy chain fusion is connected to the one or more regions of an immunoglobulin light chain by disulfide bonds or a connecting peptide. In some embodiments, the therapeutic peptide comprises a relaxin B chain and a relaxin A chain. The relaxin B and relaxin A chains may be connected by a peptide linker. The peptide linker may comprise a protease cleavage site.

The immunoglobulin fusion protein may comprise an amino acid sequence that is based on or derived from any one of SEQ ID NOs: 20-22. The immunoglobulin fusion protein may comprise an amino acid sequence that is at least about 50% homologous to any one of SEQ ID NOs: 20-22. The immunoglobulin fusion protein may comprise an amino acid sequence that is at least about 60%, 65%, 70%, 75%, 80%, 85%, 90%, 95%, or 97% homologous to any one of SEQ ID NOs 20-22. The immunoglobulin fusion protein may comprise an amino acid sequence that is at least about 70% homologous to any one of SEQ ID NOs: 20-22. The immunoglobulin fusion protein may comprise an amino acid sequence that is at least about 80% homologous to any one of SEQ ID NOs: 20-22. The immunoglobulin fusion protein may comprise an amino acid sequence that is at least about 50% identical to any one of SEQ ID NOs: 20-22. The immunoglobulin fusion protein may comprise an amino acid sequence that is at least about 60%, 65%, 70%, 75%, 80%, 85%, 90%, 95%, or 97% identical to any one of SEQ ID NOs 20-22. The immunoglobulin fusion protein may comprise an amino acid sequence that is at least about 70% identical to any one of SEQ ID NOs: 20-22. The immunoglobulin fusion protein may comprise an amino acid sequence that is at least about 80% identical to any one of SEQ ID NOs: 20-22. The immunoglobulin fusion protein may comprise an amino acid sequence that is 100% identical to any one of SEQ ID NOs: 20-22. In some embodiments, the immunoglobulin fusion protein comprises an amino acid sequence that is at least about 50%, 55%, 60%, 65%, 70%, 75%, 80%, 85%, 90%, 95%, or 97% homologous to an amino acid sequence of any one of SEQ ID NOs: 20-22. In some embodiments, the immunoglobulin fusion protein comprises an amino acid sequence that is at least about 50%, 55%, 60%, 65%, 70%, 75%, 80%, 85%, 90%, 95%, or 97% identical to an amino acid sequence of any one of SEQ ID NOs: 20-22.

The immunoglobulin fusion protein may comprise an amino acid sequence that is based on or derived from SEQ ID NO: 22. The immunoglobulin fusion protein may comprise an amino acid sequence that is at least about 50% homologous to SEQ ID NO: 22. The immunoglobulin fusion protein may comprise an amino acid sequence that is at least about 60%, 65%, 70%, 75%, 80%, 85%, 90%, 95%, or 97% homologous to SEQ ID NO: 22. The immunoglobulin fusion protein may comprise an amino acid sequence that is at least about 70% homologous to SEQ ID NO: 22. The immunoglobulin fusion protein may comprise an amino acid sequence that is at least about 80% homologous to SEQ ID NO: 22. The immunoglobulin fusion protein may comprise an amino acid sequence that is at least about 50% identical to SEQ ID NO: 22. The immunoglobulin fusion protein may comprise an amino acid sequence that is at least about 60%, 65%, 70%, 75%, 80%, 85%, 90%, 95%, or 97% identical to SEQ ID NO: 22. The immunoglobulin fusion protein may comprise an amino acid sequence that is at least about 70% identical to SEQ ID NO: 22. The immunoglobulin fusion protein may comprise an amino acid sequence that is at least about 80% identical to SEQ ID NO: 22. The immunoglobulin fusion protein may comprise an amino acid sequence that is 100% identical to SEQ ID NO: 22. In some embodiments, the immunoglobulin fusion protein comprises an amino acid sequence that is at least about 50%, 55%, 60%, 65%, 70%, 75%, 80%, 85%, 90%, 95%, or 97% homologous to an amino acid sequence of SEQ ID NO: 22. In some embodiments, the immunoglobulin fusion protein comprises an amino acid sequence that is at least about 50%, 55%, 60%, 65%, 70%, 75%, 80%, 85%, 90%, 95%, or 97% identical to an amino acid sequence of SEQ ID NO: 22.

The immunoglobulin fusion protein may comprise an amino acid sequence comprising 10, 20, 30, 40, 50, 60, 70, 80, 90, 100 or more amino acids based on or derived from any one of SEQ ID NOs: 20-22. The immunoglobulin fusion protein may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 20-22. The immunoglobulin fusion protein may comprise an amino acid sequence comprising 10 or more amino acids based on or derived from any one of SEQ ID NOs: 20-22. The immunoglobulin fusion protein may comprise an amino acid sequence comprising 50 or more amino acids based on or derived from any one of SEQ ID NOs: 20-22. The immunoglobulin fusion protein may comprise an amino acid sequence comprising 100 or more amino acids based on or derived from any one of SEQ ID NOs: 20-22. The immunoglobulin fusion protein may comprise an amino acid sequence comprising 200 or more amino acids based on or derived from any one of SEQ ID NOs: 20-22. The amino acids may be consecutive. Alternatively, or additionally, the amino acids are nonconsecutive. In some embodiments, the immunoglobulin fusion protein may comprise amino acids derived from any one of SEQ ID NOs: 20-22 and amino acids not derived from any one of SEQ ID NOs: 20-22. In some embodiments, the immunoglobulin fusion protein may comprise amino acids derived from one or more of SEQ ID NOs: 20-22 and amino acids not derived from any one of SEQ ID NOs: 20-22. In some embodiments, the immunoglobulin fusion protein comprises amino acids derived from 1, 2, 3, 4, 5, 6, 7, 8, 9, 10 or more of SEQ ID NOs: 20-22.

The immunoglobulin fusion protein may be encoded by a nucleotide sequence that is based on or derived from any one of SEQ ID NOs: 17-19. The immunoglobulin fusion protein may be encoded by a nucleotide sequence that is at least about 50% homologous to any one of SEQ ID NOs: 17-19. The immunoglobulin fusion protein may be encoded by a nucleotide sequence that is at least about 60%, 65%, 70%, 75%, 80%, 85%, 90%, 95%, or 97% homologous to any one of SEQ ID NOs: 17-19. The immunoglobulin fusion protein may be encoded by a nucleotide sequence that is at least about 70% homologous to any one of SEQ ID NOs: 17-19. The immunoglobulin fusion protein may be encoded by a nucleotide sequence that is at least about 80% homologous to any one of SEQ ID NOs: 17-19. The immunoglobulin fusion protein may be encoded by a nucleotide sequence that is at least about 50% identical to any one of SEQ ID NOs: 17-19. The immunoglobulin fusion protein may be encoded by a nucleotide sequence that is at least about 60%, 65%, 70%, 75%, 80%, 85%, 90%, 95%, or 97% identical to any one of SEQ ID NOs: 17-19. The immunoglobulin fusion protein may be encoded by a nucleotide sequence that is at least about 70% identical to any one of SEQ ID NOs: 17-19. The immunoglobulin fusion protein may be encoded by a nucleotide sequence that is at least about 80% identical to any one of SEQ ID NOs: 17-19. The immunoglobulin fusion protein may be encoded by a nucleotide sequence that is 100% identical to any one of SEQ ID NOs: 17-19. In some embodiments, the immunoglobulin fusion protein is encoded by a nucleotide sequence that is at least about 50%, 55%, 60%, 65%, 70%, 75%, 80%, 85%, 90%, 95%, or 97% homologous to an amino acid sequence of any one of SEQ ID NOs: 17-19. In some embodiments, the immunoglobulin fusion protein is encoded by a nucleotide sequence that is at least about 50%, 55%, 60%, 65%, 70%, 75%, 80%, 85%, 90%, 95%, or 97% identical to an amino acid sequence of any one of SEQ ID NOs: 17-19.

The immunoglobulin fusion protein may be encoded by a nucleotide sequence that is based on or derived from SEQ ID NO: 19. The immunoglobulin fusion protein may be encoded by a nucleotide sequence that is at least about 50% homologous to SEQ ID NO: 19. The immunoglobulin fusion protein may be encoded by a nucleotide sequence that is at least about 60%, 65%, 70%, 75%, 80%, 85%, 90%, 95%, or 97% homologous to SEQ ID NO: 19. The immunoglobulin fusion protein may be encoded by a nucleotide sequence that is at least about 70% homologous to SEQ ID NO: 19. The immunoglobulin fusion protein may be encoded by a nucleotide sequence that is at least about 80% homologous to SEQ ID NO: 19. The immunoglobulin fusion protein may be encoded by a nucleotide sequence that is at least about 50% identical to SEQ ID NO: 19. The immunoglobulin fusion protein may be encoded by a nucleotide sequence that is at least about 60%, 65%, 70%, 75%, 80%, 85%, 90%, 95%, or 97% identical to SEQ ID NO: 19. The immunoglobulin fusion protein may be encoded by a nucleotide sequence that is at least about 70% identical to SEQ ID NO: 19. The immunoglobulin fusion protein may be encoded by a nucleotide sequence that is at least about 80% identical to SEQ ID NO: 19. The immunoglobulin fusion protein may be encoded by a nucleotide sequence that is 100% identical to SEQ ID NO: 19. In some embodiments, the immunoglobulin fusion protein is encoded by a nucleotide sequence that is at least about 50%, 55%, 60%, 65%, 70%, 75%, 80%, 85%, 90%, 95%, or 97% homologous to SEQ ID NO: 19. In some embodiments, the immunoglobulin fusion protein is encoded by a nucleotide sequence that is at least about 50%, 55%, 60%, 65%, 70%, 75%, 80%, 85%, 90%, 95%, or 97% identical to SEQ ID NO: 19.

The immunoglobulin fusion protein may be encoded by a nucleotide sequence comprising 10, 20, 30, 40, 50, 60, 70, 80, 90, 100 or more nucleotides based on or derived from any one of SEQ ID NOs: 17-19. The immunoglobulin fusion protein may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 17-19. The immunoglobulin fusion protein may be encoded by a nucleotide sequence comprising 600, 650, 700, 750, 800, 850, 900, 950, 1000 or more nucleotides based on or derived from any one of SEQ ID NOs: 17-19. The immunoglobulin fusion protein may be encoded by a nucleotide sequence comprising 1100, 1200, 1300, 1400, 1500 or more nucleotides based on or derived from any one of SEQ ID NOs: 17-19. The immunoglobulin fusion protein may be encoded by a nucleotide sequence comprising 100 or more nucleotides based on or derived from any one of SEQ ID NOs: 17-19. The immunoglobulin fusion protein may be encoded by a nucleotide sequence comprising 500 or more nucleotides based on or derived from any one of SEQ ID NOs: 17-19. The immunoglobulin fusion protein may be encoded by a nucleotide sequence comprising 1,000 or more nucleotides based on or derived from any one of SEQ ID NOs: 17-19. The immunoglobulin fusion protein may be encoded by a nucleotide sequence comprising 1,300 or more nucleotides based on or derived from any one of SEQ ID NOs: 17-19. The nucleotides may be consecutive. Alternatively, or additionally, the nucleotides are nonconsecutive. In some embodiments, the immunoglobulin fusion protein is encoded by a nucleotide sequence comprising nucleotides derived from any one of SEQ ID NOs: 17-19 and nucleotides not derived from any one of SEQ ID NOs: 17-19. In some embodiments, the immunoglobulin fusion protein is encoded by a nucleotide sequence comprising nucleotides derived from one or more of SEQ ID NOs: 25-44 and nucleotides not derived from any one of SEQ ID NOs: 17-19. In some embodiments, the immunoglobulin fusion protein is encoded by a nucleotide sequence derived from 1, 2, 3, 4, 5, 6, 7, 8, 9, 10 or more of SEQ ID NOs: 17-19.

Further disclosed herein are nucleotide constructs comprising a nucleotide sequence that is based on or derived from any one of SEQ ID NOs: 17-19. The nucleotide construct may be a plasmid for expression in a host cell. For example, a mammalian or bacterial expression plasmid. In some embodiments, the construct comprises a nucleotide sequence that is at least about 50% homologous to any one of SEQ ID NOs: 17-19. In some embodiments, the construct comprises a nucleotide sequence that is at least about 60%, 65%, 70%, 75%, 80%, 85%, 90%, 95%, or 97% homologous to any one of SEQ ID NOs: 17-19. In some embodiments, the construct comprises a nucleotide sequence that is at least about 70% homologous to any one of SEQ ID NOs: 17-19. In some embodiments, the construct comprises a nucleotide sequence that is at least about 80% homologous to any one of SEQ ID NOs: 17-19. In some embodiments, the construct comprises a nucleotide sequence that is at least about 50% identical to any one of SEQ ID NOs: 17-19. In some embodiments, the construct comprises a nucleotide sequence that is at least about 60%, 65%, 70%, 75%, 80%, 85%, 90%, 95%, or 97% identical to any one of SEQ ID NOs: 17-19. In some embodiments, the construct comprises a nucleotide sequence that is at least about 70% identical to any one of SEQ ID NOs: 17-19. In some embodiments, the construct comprises a nucleotide sequence that is at least about 80% identical to any one of SEQ ID NOs: 17-19. In some embodiments, the construct comprises a nucleotide sequence that is 100% identical to any one of SEQ ID NOs: 17-19. In some embodiments, the construct comprises a nucleotide sequence that is at least about 50%, 55%, 60%, 65%, 70%, 75%, 80%, 85%, 90%, 95%, or 97% homologous to an amino acid sequence of any one of SEQ ID NOs: 17-19. In some embodiments, the construct comprises a nucleotide sequence that is at least about 50%, 55%, 60%, 65%, 70%, 75%, 80%, 85%, 90%, 95%, or 97% identical to an amino acid sequence of any one of SEQ ID NOs: 17-19.

Further disclosed herein are nucleotide constructs comprising a nucleotide sequence that is based on or derived from SEQ ID NO: 19. The nucleotide construct may be a plasmid for expression in a host cell. For example, a mammalian or bacterial expression plasmid. In some embodiments, the construct comprises a nucleotide sequence that is at least about 50% homologous to SEQ ID NO: 19. In some embodiments, the construct comprises a nucleotide sequence that is at least about 60%, 65%, 70%, 75%, 80%, 85%, 90%, 95%, or 97% homologous to SEQ ID NO: 19. In some embodiments, the construct comprises a nucleotide sequence that is at least about 70% homologous to SEQ ID NO: 19. In some embodiments, the construct comprises a nucleotide sequence that is at least about 80% homologous to SEQ ID NO: 19. In some embodiments, the construct comprises a nucleotide sequence that is at least about 50% identical to a SEQ ID NO: 19. In some embodiments, the construct comprises a nucleotide sequence that is at least about 60%, 65%, 70%, 75%, 80%, 85%, 90%, 95%, or 97% identical to SEQ ID NO: 19. In some embodiments, the construct comprises a nucleotide sequence that is at least about 70% identical to SEQ ID NO: 19. In some embodiments, the construct comprises a nucleotide sequence that is at least about 80% identical to SEQ ID NO: 19. In some embodiments, the construct comprises a nucleotide sequence that is 100% identical to SEQ ID NO: 19. In some embodiments, the construct comprises a nucleotide sequence that is at least about 50%, 55%, 60%, 65%, 70%, 75%, 80%, 85%, 90%, 95%, or 97% homologous to SEQ ID NO: 19. In some embodiments, the construct comprises a nucleotide sequence that is at least about 50%, 55%, 60%, 65%, 70%, 75%, 80%, 85%, 90%, 95%, or 97% identical to SEQ ID NO: 19.

The immunoglobulin fusion protein may comprise an immunoglobulin heavy chain fusion that is based on or derived from any one or more of SEQ ID NOs: 20-22.

The immunoglobulin fusion protein may comprise an immunoglobulin heavy chain fusion that is based on or derived from SEQ ID NO: 22.

The immunoglobulin fusion protein may comprise a second immunoglobulin region derived from an immunoglobulin heavy chain including any one or more of SEQ ID NOs: 20-22.

The immunoglobulin fusion protein may comprise an immunoglobulin light chain fusion that is based on or derived from any one or more of SEQ ID NOs: 9-12.

The immunoglobulin fusion protein may comprise an immunoglobulin light chain fusion that is based on or derived from SEQ ID NO: 12.

The immunoglobulin fusion protein may comprise a second immunoglobulin region derived from an immunoglobulin light chain including any one or more of SEQ ID NOs: 9-12.

The immunoglobulin fusion protein may comprise (a) a region of an immunoglobulin heavy chain that is based on or derived from any one or more of SEQ ID NOs: 20-22; and (b) a region of an immunoglobulin light chain that is based on or derived from any one or more of SEQ ID NOs: 9-12. The immunoglobulin fusion protein may comprise (a) a region of an immunoglobulin heavy chain comprising an amino acid sequence that is at least about 50% identical to SEQ ID NOs 20-22; and (b) a region of an immunoglobulin light chain comprising an amino acid sequence that is at least about 50% identical to SEQ ID NOs: 9-12. The region of an immunoglobulin heavy chain may comprise an amino acid sequence that is at least about 60%, 70%, 75%, 80%, 90%, 95%, or 97% identical to SEQ ID NOs: 20-22. The region of an immunoglobulin heavy chain may comprise an amino acid sequence that is 100% identical to SEQ ID NOs: 20-22. The region of an immunoglobulin light chain may comprise an amino acid sequence that is at least about 60%, 70%, 75%, 80%, 90%, 95%, or 97% identical to SEQ ID NOs: 9-12. The region of an immunoglobulin light chain may comprise an amino acid sequence that is 100% identical to SEQ ID NOs: 9-12.

The immunoglobulin fusion protein may comprise (a) a region of an immunoglobulin heavy chain that is based on or derived from SEQ ID NO: 22; and (b) a region of an immunoglobulin light chain that is based on or derived from SEQ ID NO: 12. The immunoglobulin fusion protein may comprise (a) a region of an immunoglobulin heavy chain comprising an amino acid sequence that is at least about 50% identical to SEQ ID NO: 22; and (b) a region of an immunoglobulin light chain comprising an amino acid sequence that is at least about 50% identical to SEQ ID NO: 12. The region of an immunoglobulin heavy chain may comprise an amino acid sequence that is at least about 60%, 70%, 75%, 80%, 90%, 95%, or 97% identical to SEQ ID NO: 22. The region of an immunoglobulin heavy chain may comprise an amino acid sequence that is 100% identical to SEQ ID NO: 22. The region of an immunoglobulin light chain may comprise an amino acid sequence that is at least about 60%, 70%, 75%, 80%, 90%, 95%, or 97% identical to SEQ ID NO: 12. The region of an immunoglobulin light chain may comprise an amino acid sequence that is 100% identical to SEQ ID NO: 12.

The immunoglobulin fusion protein may comprise (a) a region of an immunoglobulin heavy chain encoded by a nucleotide sequence of SEQ ID NOs: 5-8, 17-19; and (b) a region of an immunoglobulin light chain encoded by a nucleotide sequence of SEQ ID NOs: 1-4. The immunoglobulin protein may comprise (a) a region of an immunoglobulin heavy chain encoded by a nucleotide sequence that is at least 50% or more identical to a nucleotide sequence of SEQ ID NOs: 5-8, 17-19; and (b) a region of an immunoglobulin light chain encoded by a nucleotide sequence that is at least 50% or more identical to a nucleotide sequence of SEQ ID NOs: 1-4. The region of an immunoglobulin heavy chain may be encoded by a nucleotide sequence that is at least 60%, 70%, 75%, 80%, 90%, 95%, or 97% or more identical to a nucleotide sequence of SEQ ID NOs: 5-8, 17-19. The region of an immunoglobulin heavy chain may be encoded by a nucleotide sequence that is 100% identical to a nucleotide sequence of SEQ ID NOs: 5-8, 17-19. The region of an immunoglobulin light chain may be encoded by a nucleotide sequence that is at least 60%, 70%, 75%, 80%, 90%, 95%, or 97% or more identical to a nucleotide sequence of SEQ ID NOs: 1-4. The region of an immunoglobulin light chain may be encoded by a nucleotide sequence that is 100% identical to a nucleotide sequence of SEQ ID NOs: 1-4.

The immunoglobulin glucagon fusion protein may comprise (a) a first immunoglobulin fusion protein encoded by a nucleotide sequence of any one of SEQ ID NOs: 17-19; and (b) a second immunoglobulin protein encoded by a nucleotide sequence of SEQ ID NO: 1. The immunoglobulin glucagon fusion protein may comprise (a) a first immunoglobulin fusion protein encoded by a nucleotide sequence that is at least 50% or more homologous to a nucleotide sequence of any one of SEQ ID NOs: 17-19; and (b) a second immunoglobulin protein encoded by a nucleotide sequence that is at least 50% or more homologous to a nucleotide sequence of SEQ ID NO: 1. In some embodiments, the first immunoglobulin fusion protein is encoded by a nucleotide sequence that is at least 60%, 70%, 75%, 80%, 90%, 95%, or 97% or more homologous to a nucleotide sequence of any one of SEQ ID NOs: 17-19. In some embodiments, the second immunoglobulin protein is encoded by a nucleotide sequence that is at least 60%, 70%, 75%, 80%, 90%, 95%, or 97% or more homologous to a nucleotide sequence of SEQ ID NO: 1.

In some embodiments, provided herein are immunoglobulin relaxin fusion proteins. In some embodiments, the immunoglobulin relaxin fusion proteins comprise an immunoglobulin light chain and/or heavy chain region fused at the amino terminus with a relaxin or a peptide derived from relaxin, which includes relaxins having internal linkers. In some embodiments, the immunoglobulin relaxin fusion proteins further comprise a second immunoglobulin light chain and/or heavy chain. In some embodiments, an immunoglobulin relaxin fusion protein refers to a first immunoglobulin chain comprising an amino-terminal relaxin peptide or derivative thereof and a second immunoglobulin chain. In some embodiments, the first immunoglobulin relaxin fusion protein is co-expressed with the second immunoglobulin chain. In some embodiments, the immunoglobulin relaxin fusion protein comprises a heavy chain having an amino acid sequence based on or derived from any one or more of SEQ ID NO: 20-22 and a light chain having an amino acid sequence based on or derived from any one or more of SEQ ID NO: 9-12. In some embodiments, the immunoglobulin relaxin fusion protein comprises a heavy chain having an amino acid sequence based on or derived from SEQ ID NO: 22 and a light chain having an amino acid sequence based on or derived from SEQ ID NO: 12. In some embodiments, the immunoglobulin relaxin fusion proteins are configured to treat a disease or condition of the heart. In some embodiments, the immunoglobulin relaxin fusion proteins treat a disease or condition including heart failure, acute coronary syndrome, atrial fibrillation, cardiac fibrosis, coronary artery disease, ischemia reperfusion associated with solid organ transplant (e.g., lung, kidney, liver, heart), cardiopulmonary bypass for organ protection (e.g., renal), ischemic stroke, corneal healing (ocular administration), diabetic nephropathy, cirrhosis, portal hypertension, diabetic would healing, systemic sclerosis, cervical ripening at time of labor, preeclampsia, portal hypertension, fibrosis, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (coronary artery bypass graft, CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures. Further provided is the use of the compounds of the present disclosure for the prophylaxis and/or treatment of respiratory disorders, such as, for example, chronic obstructive pulmonary disease (chronic bronchitis, COPD), interstitial lung disease, asthma, pulmonary emphysema, bronchiectases, cystic fibrosis (mucoviscidosis) and pulmonary hypertension, in particular pulmonary arterial hypertension, and combinations thereof. In some embodiments, the immunoglobulin relaxin fusion proteins are configured to treat a disease or condition of the kidney. In some embodiments, the immunoglobulin relaxin fusion proteins treat a disease or condition including acute and chronic kidney diseases and acute and chronic renal insufficiencies, as well as acute and chronic renal failure, including acute and chronic stages of renal failure with and without the requirement of dialysis, as well as the underlying or related kidney diseases such as renal hypoperfusion, dialysis induced hypotension, glomerulopathies, glomerular and tubular proteinuria, renal edema, hematuria, primary, secondary, as well as acute and chronic glomerulonephritis, membranous and membranoproliferative glomerulonephritis, Alport-Syndrome, glomerulosclerosis, interstistial tubular diseases, nephropathic diseases, such as primary and inborn kidney diseases, renal inflammation, immunological renal diseases like renal transplant rejection, immune complex induced renal diseases, as well as intoxication induced nephropathic diseases, diabetic and non-diabetic renal diseases, pyelonephritis, cystic kidneys, nephrosclerosis, hypertensive nephrosclerosis, nephrotic syndrome, that are characterized and diagnostically associated with an abnormal reduction in creatinine clearance and/or water excretion, abnormal increased blood concentrations of urea, nitrogen, potassium and/or creatinine, alteration in the activity of renal enzymes, such as glutamylsynthetase, urine osmolarity and urine volume, increased microalbuminuria, macroalbuminuria, glomerular and arteriolar lesions, tubular dilation, hyperphosphatemia, the requirement of dialysis, renal carcinomas, after incomplete resection of the kidney, dehydration after overuse of diuretics, uncontrolled blood pressure increase with malignant hypertension, urinary tract obstruction and infection, amyloidosis, as well as systemic diseases associated with glomerular damage, such as Lupus erythematodes, and rheumatic immunological systemic diseases, as well as renal artery stenosis, renal artery thrombosis, renal vein thrombosis, analgetics induced nephropathy, renal tubular acidosis, and combinations thereof. In some embodiments, the immunoglobulin relaxin fusion proteins are configured to treat a disease or condition of the lung. In some embodiments the immunoglobulin relaxin fusion proteins treat a disease or condition including asthmatic disorders, pulmonary arterial hypertension (PAH) and other forms of pulmonary hypertension (PH) including left-heart disease, HIV, sickle cell anemia, thromboembolisms (CTEPH), sarcoidosis, COPD-associated pulmonary hypertension, pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke), cystic fibrosis (CF), and combinations thereof.

Immunoglobulin Region

The immunoglobulin fusion proteins disclosed herein comprise one or more immunoglobulin regions. The immunoglobulin regions may comprise one or more portions of an antigen binding domain, wherein the antigen binding domain is not specific for a human antigen. In some cases, the immunoglobulin region is modified from a palivizumab antibody. The modification may include one or more amino acid mutations, insertions or deletions in one or more CDRs of the palivizumab antibody. As a non-limiting example, 1, 2, 3, 4 or 5 amino acids of the CDR3 of a palivizumab heavy chain sequence is modified.

The immunoglobulin region may comprise an entire immunoglobulin molecule or any polypeptide comprising fragment of an immunoglobulin including, but not limited to, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any combination thereof. In some embodiments, an immunoglobulin heavy chain may comprise an entire heavy chain or a portion of a heavy chain. For example, a variable domain or region thereof derived from a heavy chain may be referred to as a heavy chain or a region of a heavy chain. In some embodiments, an immunoglobulin light chain may comprise an entire light chain or a portion of a light chain. For example, a variable domain or region thereof derived from a light chain may be referred to as a light chain or a region of a light chain. A single domain immunoglobulin includes, but is not limited to, a single monomeric variable immunoglobulin domain, for example, a shark variable new antigen receptor immunoglobulin fragment (VNAR).

The immunoglobulin may be derived from any type known to one of skill in the art including, but not limited to, IgA, IgD, IgE, IgG, IgM, IgY, IgW. The immunoglobulin region may comprise one or more units, including but not limited to, 1, 2, 3, 4, and 5 units. Functional units may include, but are not limited to, non-immunoglobulin regions, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any combination or fragments thereof. Non-immunoglobulin regions include, but are not limited to, carbohydrates, lipids, small molecules and therapeutic peptides. The immunoglobulin region may comprise one or more units connected by one or more disulfide bonds. The immunoglobulin region may comprise one or more units connected by a peptide linker, for example, a scFv immunoglobulin. The immunoglobulin may be a recombinant immunoglobulin including immunoglobulins with amino acid mutations, substitutions, and/or deletions. The immunoglobulin may be a recombinant immunoglobulin comprising chemical modifications. The immunoglobulin may comprise a whole or part of an immunoglobulin-drug conjugate.

The immunoglobulin region may comprise at least a portion of a human immunoglobulin. The immunoglobulin region may comprise at least a portion of a humanized immunoglobulin. The immunoglobulin region may comprise at least a portion of a chimeric immunoglobulin. The immunoglobulin region may be based on or derived from a human immunoglobulin. The immunoglobulin region may be based on or derived from a humanized immunoglobulin. The immunoglobulin region may be based on or derived from a chimeric immunoglobulin. The immunoglobulin region may be based on or derived from a monoclonal immunoglobulin. The immunoglobulin region may be based on or derived from a polyclonal immunoglobulin. The immunoglobulin region may comprise at least a portion of an immunoglobulin from a mammal, avian, reptile, amphibian, or a combination thereof. The mammal may be a human. The mammal may be a non-human primate. The mammal may be a dog, cat, sheep, goat, cow, rabbit, or mouse.

The immunoglobulin region may comprise at least a portion of an immunoglobulin heavy chain. The immunoglobulin region may comprise one or more immunoglobulin heavy chains or a portion thereof. The immunoglobulin region may comprise two or more immunoglobulin heavy chains or a portion thereof. The immunoglobulin region may comprise an amino acid sequence that is at least about 50% homologous to an immunoglobulin heavy chain. The immunoglobulin region may comprise an amino acid sequence that is at least about 60%, 65%, 70%, 75%, 80%, 85%, 90%, 92%, 95%, or 97% or more homologous to an immunoglobulin heavy chain. The immunoglobulin region may comprise an amino acid sequence that is at least about 70% homologous to an immunoglobulin heavy chain. The immunoglobulin region may comprise an amino acid sequence that is at least about 80% homologous to an immunoglobulin heavy chain. The immunoglobulin region may comprise an amino acid sequence that is at least about 90% homologous to an immunoglobulin heavy chain. The immunoglobulin heavy chain may comprise SEQ ID NOs: 13-16. In some embodiments, the immunoglobulin region comprises an amino acid sequence that is at least about 50%, 55%, 60%, 65%, 70%, 75%, 80%, 85%, 90%, 95%, or 97% homologous to an amino acid sequence of any one of SEQ ID NOs: 13-16. In some embodiments, the immunoglobulin region comprises an amino acid sequence that is at least about 50%, 55%, 60%, 65%, 70%, 75%, 80%, 85%, 90%, 95%, or 97% identical to an amino acid sequence of any one of SEQ ID NOs: 13-16.

The immunoglobulin region may comprise an amino acid sequence comprising 5, 10, 15, 20, 25, 30, 35, 40, 45, 50, 60, 70, 80, 90 or more amino acids of an immunoglobulin heavy chain. The immunoglobulin region may comprise an amino acid sequence comprising 100, 150, 200, 250, 300, 350, 400, 450, 500, 600, 700, 800, 900 or more amino acids of an immunoglobulin heavy chain. The amino acids may be consecutive. Alternatively, or additionally, the amino acids are non-consecutive.

The immunoglobulin heavy chain may be encoded by a nucleotide sequence based on or derived from SEQ ID NOs: 5-8. The immunoglobulin heavy chain may be encoded by a nucleotide sequence that is at least about 50% homologous to SEQ ID NOs: 5-8. The immunoglobulin heavy chain may be encoded by a nucleotide sequence that is at least about 60%, 65%, 70%, 75%, 80%, 85%, 90%, 92%, 95%, or 97% or more homologous to SEQ ID NOs: 5-8. The immunoglobulin heavy chain may be encoded by a nucleotide sequence that is at least about 75% homologous to SEQ ID NOs: 5-8. The immunoglobulin heavy chain may be encoded by a nucleotide sequence that is at least about 85% homologous to SEQ ID NOs: 5-8. In some embodiments, the immunoglobulin region is encoded by a nucleotide sequence that is at least about 50%, 55%, 60%, 65%, 70%, 75%, 80%, 85%, 90%, 95%, or 97% homologous to a nucleotide sequence of any one of SEQ ID NOs: 5-8. In some embodiments, the immunoglobulin region is encoded by a nucleotide sequence that is at least about 50%, 55%, 60%, 65%, 70%, 75%, 80%, 85%, 90%, 95%, or 97% identical to a nucleotide sequence of any one of SEQ ID NOs: 5-8.

The immunoglobulin region may comprise at least a portion of an immunoglobulin light chain. The immunoglobulin region may comprise one or more immunoglobulin light chains or a portion thereof. The immunoglobulin region may comprise two or more immunoglobulin light chains or a portion thereof. The immunoglobulin region may comprise an amino acid sequence that is at least about 50% homologous to an immunoglobulin light chain. The immunoglobulin region may comprise an amino acid sequence that is at least about 60%, 65%, 70%, 75%, 80%, 85%, 90%, 92%, 95%, or 97% or more homologous to an immunoglobulin light chain. The immunoglobulin region may comprise an amino acid sequence that is at least about 70% homologous to an immunoglobulin light chain. The immunoglobulin region may comprise an amino acid sequence that is at least about 80% homologous to an immunoglobulin light chain. The immunoglobulin region may comprise an amino acid sequence that is at least about 90% homologous to an immunoglobulin light chain. The immunoglobulin light chain may comprise SEQ ID NOs: 9-12. In some embodiments, the immunoglobulin region comprises an amino acid sequence that is at least about 50%, 55%, 60%, 65%, 70%, 75%, 80%, 85%, 90%, 95%, or 97% homologous to an amino acid sequence of any one of SEQ ID NOs: 9-12. In some embodiments, the immunoglobulin region comprises an amino acid sequence that is at least about 50%, 55%, 60%, 65%, 70%, 75%, 80%, 85%, 90%, 95%, or 97% identical to an amino acid sequence of any one of SEQ ID NOs: 9-12.

The immunoglobulin region may comprise an amino acid sequence comprising 5, 10, 15, 20, 25, 30, 35, 40, 45, 50, 60, 70, 80, 90 or more amino acids of an immunoglobulin light chain. The immunoglobulin region may comprise an amino acid sequence comprising 100, 150, 200, 250, 300, 350, 400, 450, 500, 600, 700, 800, 900 or more amino acids of an immunoglobulin light chain. The amino acids may be consecutive. Alternatively, or additionally, the amino acids are non-consecutive.

The immunoglobulin light chain may be encoded by a nucleotide sequence based on or derived from SEQ ID NOs: 1-4. The immunoglobulin light chain may be encoded by a nucleotide sequence that is at least about 50% homologous to SEQ ID NOs: 1-4. The immunoglobulin light chain may be encoded by a nucleotide sequence that is at least about 60%, 65%, 70%, 75%, 80%, 85%, 90%, 92%, 95%, or 97% or more homologous to SEQ ID NOs: 1-4. The immunoglobulin light chain may be encoded by a nucleotide sequence that is at least about 75% homologous to SEQ ID NOs: 1-4. The immunoglobulin light chain may be encoded by a nucleotide sequence that is at least about 85% homologous to SEQ ID NOs: 1-4. In some embodiments, the immunoglobulin region is encoded by a nucleotide sequence that is at least about 50%, 55%, 60%, 65%, 70%, 75%, 80%, 85%, 90%, 95%, or 97% homologous to a nucleotide sequence of any one of SEQ ID NOs: 1-4. In some embodiments, the immunoglobulin region is encoded by a nucleotide sequence that is at least about 50%, 55%, 60%, 65%, 70%, 75%, 80%, 85%, 90%, 95%, or 97% identical to a nucleotide sequence of any one of SEQ ID NOs: 1-4.

The immunoglobulin region may comprise at least a portion of a variable domain. The immunoglobulin region may comprise one or more variable domains or portions thereof. The immunoglobulin region may comprise 2, 3, 4, 5 or more variable domains or portions thereof. The immunoglobulin region may comprise an amino acid sequence comprising 10, 20, 30, 40, 50, 60, 70, 80, 90, 100, 120, 140, 160, 180, 200, 225, 250, 275, 300, 350, 400, 500 or more amino acids based on or derived from an amino acid sequence of one or more variable domains. The amino acids may be consecutive. The amino acids may be non-consecutive.

The immunoglobulin region may comprise at least a portion of a constant domain. The immunoglobulin region may comprise one or more constant domains or portions thereof. The immunoglobulin region may comprise 2, 3, 4, 5, 6, 7, 8, 9, 10 or more constant domains or portions thereof. The immunoglobulin region may comprise an amino acid sequence comprising 10, 20, 30, 40, 50, 60, 70, 80, 90, 100, 120, 140, 160, 180, 200, 225, 250, 275, 300, 350, 400, 500, 600, 700, 800, 900, 1000, 1200, 1400 or more amino acids based on or derived from an amino acid sequence of one or more constant domains. The amino acids may be consecutive. The amino acids may be non-consecutive.

The immunoglobulin region may comprise at least a portion of a complementarity-determining region (CDR). The immunoglobulin region may comprise one or more complementarity-determining regions (CDRs) or portions thereof. The immunoglobulin region may comprise 2, 3, 4, 5 or more complementarity-determining regions (CDRs) or portions thereof. The immunoglobulin region may comprise 6, 7, 8 or more complementarity-determining regions (CDRs) or portions thereof. The immunoglobulin region may comprise four or more complementarity-determining regions (CDRs) or portions thereof. The immunoglobulin region may comprise 9, 10, 11 or more complementarity-determining regions (CDRs) or portions thereof. The one or more CDRs may be CDR1, CDR2, CDR3 or a combination thereof. The one or more CDRs may be CDR1. The one or more CDRs may be CDR2. The one or more CDRs may be CDR3. The CDR may be a heavy chain CDR. The one or more CDRs may be a light chain CDR.

The immunoglobulin region may comprise a heavy chain CDR1 having an amino acid sequence based on or derived from SEQ ID NO: 72. The immunoglobulin region may comprise a heavy chain CDR2 having an amino acid sequence based on or derived from SEQ ID NO: 73. The immunoglobulin region may comprise a heavy chain CDR3 having an amino acid sequence based on or derived from any one of SEQ ID NOs: 74-88. The immunoglobulin region may comprise a light chain CDR1 having an amino acid sequence based on or derived from SEQ ID NO: 89. The immunoglobulin region may comprise a light chain CDR2 having an amino acid sequence based on or derived from SEQ ID NO: 90. The immunoglobulin region may comprise a light chain CDR3 having an amino acid sequence based on or derived from any one of SEQ ID NOs: 91-97.

The immunoglobulin region may comprise a heavy chain CDR1 having an amino acid sequence that is at least about 50% homologous to SEQ ID NO: 72. The immunoglobulin region may comprise a heavy chain CDR1 having an amino acid sequence that is at least about 60%, 65%, 70%, 75%, 80%, 85%, 90%, 95%, or 97% homologous to SEQ ID NO: 72. The immunoglobulin region may comprise a heavy chain CDR1 having an amino acid sequence that is at least about 70% homologous to SEQ ID NO: 72. The immunoglobulin region may comprise a heavy chain CDR1 having an amino acid sequence that is at least about 90% homologous to SEQ ID NO: 72. The immunoglobulin region may comprise a heavy chain CDR2 having an amino acid sequence that is at least about 50% homologous to SEQ ID NO: 73. The immunoglobulin region may comprise a heavy chain CDR2 having an amino acid sequence that is at least about 60%, 65%, 70%, 75%, 80%, 85%, 90%, 95%, or 97% homologous to SEQ ID NO: 73. The immunoglobulin region may comprise a heavy chain CDR2 having an amino acid sequence that is at least about 70% homologous to SEQ ID NO: 73. The immunoglobulin region may comprise a heavy chain CDR2 having an amino acid sequence that is at least about 90% homologous to SEQ ID NO: 73. The immunoglobulin region may comprise a heavy chain CDR3 having an amino acid sequence that is at least about 50% homologous to any one of SEQ ID NOs: 74-88. The immunoglobulin region may comprise a heavy chain CDR3 having an amino acid sequence that is at least about 60%, 65%, 70%, 75%, 80%, 85%, 90%, 95%, or 97% homologous to any one of SEQ ID NOs: 74-88. The immunoglobulin region may comprise a heavy chain CDR3 having an amino acid sequence that is at least about 70% homologous to any one of SEQ ID NOs: 74-88. The immunoglobulin region may comprise a heavy chain CDR3 having an amino acid sequence that is at least about 90% homologous to any one of SEQ ID NOs: 74-88. The immunoglobulin region may comprise a light chain CDR1 having an amino acid sequence that is at least about 50% homologous to SEQ ID NO: 89. The immunoglobulin region may comprise a light chain CDR1 having an amino acid sequence that is at least about 60%, 65%, 70%, 75%, 80%, 85%, 90%, 95%, or 97% homologous to SEQ ID NO: 89. The immunoglobulin region may comprise a light chain CDR1 having an amino acid sequence that is at least about 70% homologous to SEQ ID NO: 89. The immunoglobulin region may comprise a light chain CDR1 having an amino acid sequence that is at least about 90% homologous to SEQ ID NO: 89. The immunoglobulin region may comprise a light chain CDR2 having an amino acid sequence that is at least about 50% homologous to SEQ ID NO: 90. The immunoglobulin region may comprise a light chain CDR2 having an amino acid sequence that is at least about 60%, 65%, 70%, 75%, 80%, 85%, 90%, 95%, or 97% homologous to SEQ ID NO: 90. The immunoglobulin region may comprise a light chain CDR2 having an amino acid sequence that is at least about 70% homologous to SEQ ID NO: 90. The immunoglobulin region may comprise a light chain CDR2 having an amino acid sequence that is at least about 90% homologous to SEQ ID NO: 90. The immunoglobulin region may comprise a light chain CDR3 having an amino acid sequence that is at least about 50% homologous to any one of SEQ ID NOs: 91-97. The immunoglobulin region may comprise a light chain CDR3 having an amino acid sequence that is at least about 60%, 65%, 70%, 75%, 80%, 85%, 90%, 95%, or 97% homologous to any one of SEQ ID NOs: 91-97. The immunoglobulin region may comprise a light chain CDR3 having an amino acid sequence that is at least about 70% homologous to any one of SEQ ID NOs: 91-97. The immunoglobulin region may comprise a light chain CDR3 having an amino acid sequence that is at least about 90% homologous to any one of SEQ ID NOs: 91-97.

The immunoglobulin region may comprise an amino acid sequence comprising 1, 2, 3, 4, 5, 6, 7, 8, 9, 10 or more amino acids based on or derived from an amino acid sequence of a CDR. The immunoglobulin region may comprise an amino acid sequence comprising 3 or more amino acids based on or derived from an amino acid sequence of a CDR. The immunoglobulin region may comprise an amino acid sequence comprising 5 or more amino acids based on or derived from an amino acid sequence of a CDR. The immunoglobulin region may comprise an amino acid sequence comprising 10 or more amino acids based on or derived from an amino acid sequence of a CDR. The amino acids may be consecutive. The amino acids may be non-consecutive.

The immunoglobulin region may be based on or derived from a palivizumab immunoglobulin. The immunoglobulin region may comprise at least a portion of a palivizumab immunoglobulin. The immunoglobulin region may comprise an amino acid sequence that is at least about 50% homologous to at least a portion of a palivizumab immunoglobulin. The immunoglobulin region may comprise an amino acid sequence that is at least about 60%, 65%, 70%, 75%, 80%, 85%, 90%, 92%, 95%, or 97% or more homologous to at least a portion of a palivizumab immunoglobulin. The immunoglobulin region may comprise an amino acid sequence that is at least about 70% homologous to at least a portion of a palivizumab immunoglobulin. The immunoglobulin region may comprise an amino acid sequence that is at least about 80% homologous to at least a portion of a palivizumab immunoglobulin.

The immunoglobulin region may comprise an amino acid sequence that comprises 10, 20, 30, 40, 50, 60, 70, 80, 90 or more amino acids of a palivizumab immunoglobulin sequence. The immunoglobulin region may comprise an amino acid sequence that comprises 100, 200, 300, 400, 500, 600, 700, 800, 900 or more amino acids of a palivizumab immunoglobulin sequence. The immunoglobulin region may comprise an amino acid sequence that comprises 50 or more amino acids of a palivizumab immunoglobulin sequence. The immunoglobulin region may comprise an amino acid sequence that comprises 100 or more amino acids of a palivizumab immunoglobulin sequence. The immunoglobulin region may comprise an amino acid sequence that comprises 200 or more amino acids of a palivizumab immunoglobulin sequence.

The immunoglobulin region may comprise an amino acid sequence that comprises 10, 20, 30, 40, 50, 60, 70, 80, 90 or more consecutive amino acids of a palivizumab immunoglobulin sequence. The immunoglobulin region may comprise an amino acid sequence that comprises 100, 200, 300, 400, 500, 600, 700, 800, 900 or more consecutive amino acids of a palivizumab immunoglobulin sequence. The immunoglobulin region may comprise an amino acid sequence that comprises 50 or more consecutive amino acids of a palivizumab immunoglobulin sequence. The immunoglobulin region may comprise an amino acid sequence that comprises 100 or more consecutive amino acids of a palivizumab immunoglobulin sequence. The immunoglobulin region may comprise an amino acid sequence that comprises 200 or more consecutive amino acids of a palivizumab immunoglobulin sequence.

The immunoglobulin region may comprise a CDR sequence based on or derived from a palivizumab CDR sequence. The immunoglobulin region may comprise a palivizumab heavy chain CDR1 having an amino acid sequence based on or derived from SEQ ID NO: 72. The immunoglobulin region may comprise a palivizumab heavy chain CDR2 having an amino acid sequence based on or derived from SEQ ID NO: 73. The immunoglobulin region may comprise a palivizumab heavy chain CDR3 having an amino acid sequence based on or derived from SEQ ID NO: 74. The immunoglobulin region may comprise a mutant palivizumab heavy chain CDR3 having an amino acid sequence based on or derived from any one of SEQ ID NOs: 75-88. The immunoglobulin region having a mutant palivizumab heavy chain CDR3 may have reduced binding to RSV-F than wildtype palivizumab. The immunoglobulin region may comprise a palivizumab light chain CDR1 having an amino acid sequence based on or derived from SEQ ID NO: 89. The immunoglobulin region may comprise a palivizumab light chain CDR2 having an amino acid sequence based on or derived from SEQ ID NO: 90. The immunoglobulin region may comprise a palivizumab light chain CDR3 having an amino acid sequence based on or derived from SEQ ID NO: 91. The immunoglobulin region may comprise a mutant palivizumab light chain CDR3 having an amino acid sequence based on or derived from any one of SEQ ID NOs: 92-97. The immunoglobulin region having a mutant palivizumab light chain CDR3 may have reduced binding to RSV-F than wildtype palivizumab.

The immunoglobulin region may comprise an amino acid sequence that is based on or derived from any one of SEQ ID NOs: 10-14. The immunoglobulin region may comprise an amino acid sequence that is at least about 50% homologous to any one of SEQ ID NOs: 10-14. The immunoglobulin region may comprise an amino acid sequence that is at least about 60%, 65%, 70%, 75%, 80%, 85%, 90%, 95%, or 97% homologous to any one of SEQ ID NOs 10-14. The immunoglobulin region may comprise an amino acid sequence that is at least about 70% homologous to any one of SEQ ID NOs: 10-14. The immunoglobulin region may comprise an amino acid sequence that is at least about 80% homologous to any one of SEQ ID NOs: 10-14. The immunoglobulin region may comprise an amino acid sequence that is at least about 50% identical to any one of SEQ ID NOs: 10-14. The immunoglobulin region may comprise an amino acid sequence that is at least about 60%, 65%, 70%, 75%, 80%, 85%, 90%, 95%, or 97% identical to any one of SEQ ID NOs 10-14. The immunoglobulin region may comprise an amino acid sequence that is at least about 70% identical to any one of SEQ ID NOs: 10-14. The immunoglobulin region may comprise an amino acid sequence that is at least about 80% identical to any one of SEQ ID NOs: 10-14. The immunoglobulin region may comprise an amino acid sequence that is 100% identical to any one of SEQ ID NOs: 10-14. In some embodiments, the immunoglobulin region comprises an amino acid sequence that is at least about 50%, 55%, 60%, 65%, 70%, 75%, 80%, 85%, 90%, 95%, or 97% homologous to an amino acid sequence of any one of SEQ ID NOs: 10-14. In some embodiments, the immunoglobulin region comprises an amino acid sequence that is at least about 50%, 55%, 60%, 65%, 70%, 75%, 80%, 85%, 90%, 95%, or 97% identical to an amino acid sequence of any one of SEQ ID NOs: 10-14. The immunoglobulin region includes a Fab region that is based on or derived from a sequence from any one of SEQ ID NOs: 10-14. In some embodiments, the immunoglobulin region comprises an amino acid Fab sequence derived from a sequence that is at least about 70%, 80%, 80%, 90%, 95% or 100% to any one of SEQ ID NOs: 10-14.

The immunoglobulin region may comprise an amino acid sequence comprising 10, 20, 30, 40, 50, 60, 70, 80, 90, 100 or more amino acids based on or derived from any one of SEQ ID NOs: 10-14. The immunoglobulin region may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 10-14. The immunoglobulin region may comprise an amino acid sequence comprising 10 or more amino acids based on or derived from any one of SEQ ID NOs: 10-14. The immunoglobulin region may comprise an amino acid sequence comprising 50 or more amino acids based on or derived from any one of SEQ ID NOs: 10-14. The immunoglobulin region may comprise an amino acid sequence comprising 100 or more amino acids based on or derived from any one of SEQ ID NOs: 10-14. The immunoglobulin region may comprise an amino acid sequence comprising 200 or more amino acids based on or derived from any one of SEQ ID NOs: 10-14. The amino acids may be consecutive. Alternatively, or additionally, the amino acids are nonconsecutive. In some embodiments, the immunoglobulin region may comprise amino acids derived from any one of SEQ ID NOs: 10-14 and amino acids not derived from any one of SEQ ID NOs: 10-14. In some embodiments, the immunoglobulin region may comprise amino acids derived from one or more of SEQ ID NOs: 10-14 and amino acids not derived from any one of SEQ ID NOs: 10-14. In some embodiments, the immunoglobulin region comprises amino acids derived from 1, 2, 3, or 4 of SEQ ID NOs: 10-14.

The immunoglobulin region may be encoded by a nucleotide sequence that is based on or derived from any one of SEQ ID NOs: 3-7. The immunoglobulin region may be encoded by a nucleotide sequence that is at least about 50% homologous to any one of SEQ ID NOs: 3-7. The immunoglobulin region may be encoded by a nucleotide sequence that is at least about 60%, 65%, 70%, 75%, 80%, 85%, 90%, 95%, or 97% homologous to any one of SEQ ID NOs: 3-7. The immunoglobulin region may be encoded by a nucleotide sequence that is at least about 70% homologous to any one of SEQ ID NOs: 3-7. The immunoglobulin region may be encoded by a nucleotide sequence that is at least about 80% homologous to any one of SEQ ID NOs: 3-7. The immunoglobulin region may be encoded by a nucleotide sequence that is at least about 50% identical to any one of SEQ ID NOs: 3-7. The immunoglobulin region may be encoded by a nucleotide sequence that is at least about 60%, 65%, 70%, 75%, 80%, 85%, 90%, 95%, or 97% identical to any one of SEQ ID NOs: 3-7. The immunoglobulin region may be encoded by a nucleotide sequence that is at least about 70% identical to any one of SEQ ID NOs: 3-7. The immunoglobulin region may be encoded by a nucleotide sequence that is at least about 80% identical to any one of SEQ ID NOs: 3-7. The immunoglobulin region may be encoded by a nucleotide sequence that is 100% identical to any one of SEQ ID NOs: 3-7. The immunoglobulin region includes a Fab region that is based on or derived from a sequence from any one of SEQ ID NOs: 3-7. In some embodiments, the immunoglobulin region comprises an amino acid Fab sequence derived from a sequence that is at least about 70%, 80%, 80%, 90%, 95% or 100% to any one of SEQ ID NOs: 3-7.

The immunoglobulin region may be encoded by a nucleotide sequence comprising 10, 20, 30, 40, 50, 60, 70, 80, 90, 100 or more nucleotides based on or derived from any one of SEQ ID NOs: 3-7. The immunoglobulin region may be encoded by a nucleotide sequence comprising 125, 150, 175, 200, 225, 250, 275, 300, 325, 350, 375, 400, 425, 450, 475, 450, 500 or more nucleotides based on or derived from any one of SEQ ID NOs: 3-7. The immunoglobulin region may be encoded by a nucleotide sequence comprising 600, 650, 700, 750, 800, 850, 900, 950, 1000 or more nucleotides based on or derived from any one of SEQ ID NOs: 3-7. The immunoglobulin region may be encoded by a nucleotide sequence comprising 1100, 1200, 1300, 1400, 1500 or more nucleotides based on or derived from any one of SEQ ID NOs: 3-7. The immunoglobulin region may be encoded by a nucleotide sequence comprising 100 or more nucleotides based on or derived from any one of SEQ ID NOs: 3-7. The immunoglobulin region may be encoded by a nucleotide sequence comprising 500 or more nucleotides based on or derived from any one of SEQ ID NOs: 3-7. The immunoglobulin region may be encoded by a nucleotide sequence comprising 1000 or more nucleotides based on or derived from any one of SEQ ID NOs: 3-7. The immunoglobulin region may be encoded by a nucleotide sequence comprising 1300 or more nucleotides based on or derived from any one of SEQ ID NOs: 3-7. The nucleotides may be consecutive. In some embodiments, the immunoglobulin region is encoded by a nucleotide sequence comprising nucleotides derived from any one of SEQ ID NOs: 3-7 and nucleotides not derived from any one of SEQ ID NOs: 3-7. In some embodiments, the immunoglobulin region is encoded by a nucleotide sequence comprising nucleotides derived from one or more of SEQ ID NOs: 3-7 and nucleotides not derived from any one of SEQ ID NOs: 3-7. In some embodiments, the immunoglobulin region is encoded by a nucleotide sequence derived from 1, 2, 3, or 4 of SEQ ID NOs: 3-7.

Relaxin Therapeutic Peptide

In one aspect of the disclosure, provided herein are immunoglobulin fusion proteins comprising a therapeutic peptide and an immunoglobulin region. The immunoglobulin fusion proteins may comprise two or more therapeutic peptides. The immunoglobulin fusion proteins disclosed herein may comprise 3, 4, 5, or more therapeutic peptides. The therapeutic peptide may be attached to an immunoglobulin region via a connecting peptide. In some embodiments, one or more additional therapeutic peptides are attached to the first or a second immunoglobulin region. The one or more therapeutic peptides may be attached to one or more immunoglobulin regions. The two or more therapeutic peptides may be attached to two or more immunoglobulin regions. The two or more therapeutic peptides may be attached to one or more immunoglobulin chains. The two or more therapeutic peptides may be attached to two or more immunoglobulin chains. The two or more therapeutic peptides may be attached to one or more units within the one or more immunoglobulin regions. The two or more therapeutic peptides may be attached to two or more units within the one or more immunoglobulin regions. In some embodiments, the therapeutic peptide is connected to the immunoglobulin region without the aid of a connecting peptide.

The immunoglobulin fusion proteins disclosed herein may comprise one or more therapeutic agents. The therapeutic agent may be a peptide. The therapeutic agent may be a small molecule. The immunoglobulin fusion proteins disclosed herein may comprise two or more therapeutic agents. The immunoglobulin fusion proteins disclosed herein may comprise 3, 4, 5, 6 or more therapeutic agents. The two or more therapeutic agents may be the same. The two or more therapeutic agents may be different.

The therapeutic peptide may comprise any secondary structure, for example alpha helix or beta strand or comprise no regular secondary structure. The therapeutic peptide may comprise amino acids with one or more modifications including, but not limited to, myristoylation, palmitoylation, isoprenylation, glypiation, lipoylation, acylation, acetylation, aklylation, methylation, glycosylation, malonylation, hydroxylation, iodination, nucleotide addition, oxidation, phosphorylation, adenylylation, propionylation, succinylation, sulfation, selenoylation, biotinylation, pegylation, deimination, deamidation, eliminylation, and carbamylation. The therapeutic peptide may comprise one or more amino acids conjugated to one or more small molecules, for example a drug. In some embodiments, the therapeutic peptide comprises one or more non-natural amino acids. In some embodiments, the therapeutic peptide comprises 1, 2, 3, 4, 5, 6, 7, 8, 9, 10, 11, 12, 13, 14, 15, 16, 17, 18, 19, 20, 30, 40, 50 or more non-natural amino acids. In some embodiments, the therapeutic peptide comprises one or more amino acids substitutions. In some embodiments, the therapeutic peptide comprises 1, 2, 3, 4, 5, 6, 7, 8, 9, 10, 11, 12, 13, 14, 15, 16, 17, 18, 19, 20, 30, 40, 50 or more amino acid substitutions.

In some embodiments, one or more regions of the therapeutic peptide is configured to treat heart failure and/or fibrosis. In some embodiments, one or more regions of the therapeutic peptide is configured to treat heart failure and/or fibrosis related conditions. In some embodiments, 2, 3, 4, 5 or more regions of the therapeutic peptide are configured to treat heart failure and/or fibrosis. In some embodiments, 2, 3, 4, 5 or more regions of the therapeutic peptide are configured to treat heart failure and/or fibrosis related conditions. Heart failure related conditions may include coronary heart disease, high blood pressure, diabetes, cardiomyopathy, heart valve disease, arrhythmias, congenital heart defects, obstructive sleep apnea, myocarditis, hyperthyroidism, hypothyroidism, emphysema, hemochromatosis, and amyloidosis. Heart failure may be left-sided heart failure, right-sided heart failure, systolic heart failure, and diastolic heart failure. Fibrosis may include, but is not limited to, pulmonary fibrosis, idiopathic pulmonary fibrosis, cystic fibrosis, cirrhosis, endomyocardial fibrosis, myocardial infarction, atrial fibrosis, mediastinal fibrosis, myelofibrosis, retroperitoneal fibrosis, progressive massive fibrosis, nephrogenic systemic fibrosis, Crohn's disease, keloid, scleroderma/systemic sclerosis, arthrofibrosis, Peyronie's disease, Dupuytren's contracture, and adhesive capsulitis.

In some embodiments, one or more regions of the therapeutic peptide comprises an amino acid sequence based on or derived from an amino acid sequence of a relaxin peptide. In some embodiments, one or more regions of the therapeutic peptide comprises an amino acid sequence based on or derived from an amino acid sequence of a relaxin-2 peptide.

In some embodiments, one or more regions of the therapeutic peptide is configured to treat heart failure. Said heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure. In some embodiments, one or more regions of the therapeutic peptide is configured to treat cardiovascular disease, lung disease, fibrotic disease, kidney disease, pancreatitis, inflammation, cancer, scleroderma, pulmonary fibrosis, renal fibrosis, hepatic fibrosis, fibrosis of the lung, heart, kidney, bone marrow, liver, dermatological fibrosis, fibrotic eye disorder, ischemia, Alzheimer's disease, corneal injury, neurodegenerative disease, cardiovascular disease, fibrotic disease, failure, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, respiratory disorders, chronic obstructive pulmonary disease, chronic bronchitis, interstitial lung disease, asthma, pulmonary emphysema, bronchiectases, cystic fibrosis (mucoviscidosis) and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstitial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematosus, rheumatic immunological systemic diseases, renal artery stenosis, renal artery thrombosis, renal vein thrombosis, analgetics induced nephropathy, polycystic kidney disease, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD-associated pulmonary hypertension, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, pulmonary emphysema induced by cigarette smoke, cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, hypertension, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, or hypercholesterolemia.

In some embodiments, amino acids of the therapeutic peptide, in whole or in part, are based on or derived from any one of SEQ ID NOs: 37-52. The therapeutic peptide may comprise an amino acid sequence that is at least about 50% homologous to any one of SEQ ID NOs: 37-52. The therapeutic peptide may comprise an amino acid sequence that is at least about 60%, 65%, 70%, 75%, 80%, 85%, 90%, 95%, or 97% homologous to any one of SEQ ID NOs: 37-52. The therapeutic peptide may comprise an amino acid sequence that is at least about 70% homologous to any one of SEQ ID NOs: 37-52. The therapeutic peptide may comprise an amino acid sequence that is at least about 80% homologous to any one of SEQ ID NOs: 37-52. The therapeutic peptide may comprise an amino acid sequence that is at least about 50% identical to any one of SEQ ID NOs: 37-52. The therapeutic peptide may comprise an amino acid sequence that is at least about 60%, 65%, 70%, 75%, 80%, 85%, 90%, 95%, or 97% identical to any one of SEQ ID NOs: 37-52. The therapeutic peptide may comprise an amino acid sequence that is at least about 70% identical to any one of SEQ ID NOs: 37-52. The therapeutic peptide may comprise an amino acid sequence that is at least about 80% identical to any one of SEQ ID NOs: 37-52. The therapeutic peptide may comprise an amino acid sequence that is 100% identical to any one of SEQ ID NOs: 37-52. In some embodiments, the therapeutic peptide comprises an amino acid sequence that is at least about 50%, 55%, 60%, 65%, 70%, 75%, 80%, 85%, 90%, 95%, or 97% homologous to an amino acid sequence of any one of SEQ ID NOs: 37-52. In some embodiments, the therapeutic peptide comprises an amino acid sequence that is at least about 50%, 55%, 60%, 65%, 70%, 75%, 80%, 85%, 90%, 95%, or 97% identical to an amino acid sequence of any one of SEQ ID NOs: 37-52. In some embodiments, the therapeutic peptide comprises an amino acid sequence that is 100% identical to an amino acid sequence of any one of SEQ ID NOs: 37-52.

The therapeutic peptide may comprise an amino acid sequence comprising 10, 20, 30, 40, 50, 60, 70, 80, 90, 100 or more amino acids based on or derived from any one of SEQ ID NOs: 37-52. The therapeutic peptide may comprise an amino acid sequence comprising 125, 150, 175, 200, 225, 250, 275, 300, 325, 350, 375, 400, 425, 450, 475, 450, 500 or more amino acids based on or derived from any one of SEQ ID NOs: 37-52. The therapeutic peptide may comprise an amino acid sequence comprising 10 or more amino acids based on or derived from any one of SEQ ID NOs: 37-52. The therapeutic peptide may comprise an amino acid sequence comprising 50 or more amino acids based on or derived from any one of SEQ ID NOs: 37-52. The therapeutic peptide may comprise an amino acid sequence comprising 100 or more amino acids based on or derived from any one of SEQ ID NOs: 37-52. The therapeutic peptide may comprise an amino acid sequence comprising 200 or more amino acids based on or derived from any one of SEQ ID NOs: 37-52. The amino acids may be consecutive. Alternatively, or additionally, the amino acids are nonconsecutive. In some embodiments, the therapeutic peptide may comprise amino acids derived from any one of SEQ ID NOs: 37-52 and amino acids not derived from any one of SEQ ID NOs: 37-52. In some embodiments, the therapeutic peptide may comprise amino acids derived from one or more of SEQ ID NOs: 37-52 and amino acids not derived from any one of SEQ ID NOs: 37-52. In some embodiments, the therapeutic peptide comprises amino acids derived from 1, 2, 3, or 4 of SEQ ID NOs: 37-52.

The therapeutic peptide may comprise a protease cleavage site. The protease cleavage site may be inserted within the therapeutic peptide. In some embodiments, the therapeutic peptide comprises a first therapeutic peptide region and a second therapeutic peptide region. In some embodiments, the therapeutic peptide comprises a protease cleavage site disposed between the first therapeutic peptide region and the second therapeutic peptide region. In some embodiments, the first therapeutic peptide region and the second therapeutic peptide region are derived from the same protein or set of amino acid sequences. In some embodiments, the first therapeutic peptide region and the second therapeutic peptide regions are derived from different proteins or sets of amino acid sequences. The one or more protease cleavage sites may be attached to the N-terminus, C-terminus or both the N- and C-termini of a region of a therapeutic peptide.

The therapeutic peptide may comprise one or more linker peptides. The therapeutic peptide may comprise two or more linker peptides. The therapeutic peptide may comprise 3, 4, 5, 6, 7 or more linker peptides. The linker peptides may be different. The linker peptides may be the same. The linker peptide may be inserted within the therapeutic peptide. In some embodiments, the therapeutic peptide comprises a first therapeutic region, a second therapeutic region, an one or more linker peptides positioned between the first therapeutic region and the second therapeutic region. The one or more linker peptides may be attached to the N-terminus, C-terminus or both the N- and C-termini of a region of a therapeutic peptide. In some embodiments, the linker peptide is derived from amino acids of any of SEQ ID NOs: 61-62.

The therapeutic peptide may comprise one or more internal linker. The internal linker may be inserted within the therapeutic peptide. In some embodiments, the therapeutic peptide comprises a first therapeutic peptide region and a second therapeutic peptide region. In some embodiments, the therapeutic peptide comprises a internal linker disposed between the first therapeutic peptide region and the second therapeutic peptide region. In some embodiments, the first therapeutic peptide region and the second therapeutic peptide region are derived from the same protein or set of amino acid sequences. In some embodiments, the first therapeutic peptide region and the second therapeutic peptide regions are derived from different proteins or sets of amino acid sequences. In some embodiments, the internal linker is derived from amino acids of any of SEQ ID NOs: 63-71. In some embodiments, the internal linker comprises amino acids having repeating sequences. In some embodiments, the internal linker has 2, 3, 4, 5, 6, 7, 8, 9, 10 or more repeating sequences. In some embodiments, the internal linker is low immunogenic. In some embodiments, the internal linker is biodegradable.

Linkers and Connecting Peptides

The immunoglobulin fusion proteins, immunoglobulin regions, therapeutic peptides, and/or non-immunoglobulin regions may further comprise one or more linkers. The immunoglobulin fusion proteins, immunoglobulin regions, and/or non-immunoglobulin regions may further comprise 2, 3, 4, 5, 6, 7, 8, 9, 10 or more linkers.

The one or more linkers are attached to the N-terminus, C-terminus or both N- and C-termini of a therapeutic peptide. The one or more linkers are attached to the N-terminus, C-terminus or both N- and C-termini of a proteolytic cleavage site. The one or more linkers may be attached to a therapeutic peptide, proteolytic cleavage site, immunoglobulin region, non-immunoglobulin region or a combination thereof.

The one or more linkers may comprise an amino acid sequence selected from any one of SEQ ID NOs:61-62. The one or more linkers may comprise an amino acid sequence that is at least about 50% homologous to any one of SEQ ID NOs: 61-62. The one or more linkers may comprise an amino acid sequence that is at least about 60%, 65%, 70%, 75%, 80%, 85%, 90%, 95% or more homologous to any one of SEQ ID NOs: 61-62. The one or more linkers may comprise an amino acid sequence that is at least about 70% homologous to any one of SEQ ID NOs: 61-62. The one or more linkers may comprise an amino acid sequence that is at least about 80% homologous to any one of SEQ ID NOs: 61-62.

In some embodiments, the linker is a connecting linker. The connecting linker may link the therapeutic peptide to an immunoglobulin region. The connecting linker may comprise an amino acid sequence that is at least about 50% homologous to any of SEQ ID NOs: 53-60. The connecting linker may comprise an amino acid sequence that is at least about 60%, 65%, 70%, 75%, 80%, 85%, 90%, 95% or more homologous to any one of SEQ ID NOs: 53-60. The connecting linker may comprise an amino acid sequence that is at least about 70% homologous to any one of SEQ ID NOs: 53-60. The connecting linker may comprise an amino acid sequence that is at least about 80% homologous to any one of SEQ ID NOs: 53-60.

In some embodiments, the linker is an internal linker. The internal linker may be a portion of a therapeutic peptide. The internal linker may link two regions of a therapeutic peptide. The internal linker may link two therapeutic peptides derived from two different peptides or proteins. The internal linker may link two therapeutic peptides derived from the same peptide or protein. The internal linker may comprise an amino acid sequence that is at least about 50% homologous to any of SEQ ID NOs: 63-71. The internal linker may comprise an amino acid sequence that is at least about 60%, 65%, 70%, 75%, 80%, 85%, 90%, 95% or more homologous to any one of SEQ ID NOs: 63-71. The internal linker may comprise an amino acid sequence that is at least about 70% homologous to any one of SEQ ID NOs: 63-71. The internal linker may comprise an amino acid sequence that is at least about 80% homologous to any one of SEQ ID NOs: 63-71.

Proteolytic Cleavage Site

The immunoglobulin fusion proteins disclosed herein may further comprise one or more proteolytic cleavage sites. The immunoglobulin fusion proteins disclosed herein may further comprise 2 or more proteolytic cleavage sites. The immunoglobulin fusion proteins disclosed herein may further comprise 3 or more proteolytic cleavage sites. The immunoglobulin fusion proteins disclosed herein may further comprise 4, 5, 6, 7 or more proteolytic cleavage sites.

The therapeutic peptides disclosed herein may further comprise one or more proteolytic cleavage sites.

The one or more proteolytic cleavage sites may be attached to the N-terminus, C-terminus or both N- and C-termini of a therapeutic peptide. The one or more proteolytic cleavage sites may attached to the N-terminus, C-terminus or both N- and C-termini of a linker. The one or more proteolytic cleavage sites may be attached to a therapeutic peptide, linker, immunoglobulin region, non-immunoglobulin region or a combination thereof.

In some embodiments, the proteolytic cleavage site is located within the amino acid sequence of the therapeutic peptide, immunoglobulin region, or a combination thereof. The therapeutic peptide may comprise one or more proteolytic cleavage sites within its amino acid sequence. For example, SEQ ID NOs: 37-39 disclose a relaxin protein comprising two internal proteolytic cleavage sites.

Two or more proteolytic cleavage sites may surround a therapeutic peptide, linker, immunoglobulin region, or combination thereof. Digestion of the proteolytic cleavage site may result in release of a peptide fragment located between the two or more proteolytic cleavage sites. For example, the proteolytic cleavage sites may flank a therapeutic peptide-linker peptide. Digestion of the proteolytic cleavage sites may result in release of the therapeutic peptide-linker.

The proteolytic cleavage site may be recognized by one or more proteases. The one or more proteases may be a serine protease, threonine protease, cysteine protease, aspartate protease, glutamic protease, metalloprotease, exopeptidases, endopeptidases, or a combination thereof. The proteases may be selected from the group comprising Factor VII or Factor Xa. Additional examples of proteases include, but are not limited to, aminopeptidases, carboxypeptidases, trypsin, chymotrypsin, pepsin, papain, and elastase. The protease may be PC2. In some embodiments, the protease recognizes the amino acid sequence KR. In some embodiments, the protease recognizes the amino acid sequence RKKR.

Vectors, Host Cells and Recombinant Methods

Immunoglobulin fusion proteins, as disclosed herein, may be expressed and purified by known recombinant and protein purification methods. In some instances, the activity of the immunoglobulin fusion protein is affected by expression and/or purification methods. For example, the activity of an immunoglobulin fusion protein configured for use as a therapeutic, is enhanced or attenuated based on the identity of the expression vector, identity of the recombinant host, identity of the cell line, expression reaction conditions, purification methods, protein processing, or any combination thereof. Expression reaction conditions include, but are not limited to, temperature, % $CO_2$, media, expression time, cofactors, and chaperones. Purification methods include, but are not limited to, purification temperatures, chromatography resins, protease inhibitors, and buffer compositions.

Immunoglobulin fusion proteins, as disclosed herein, may be expressed by recombinant methods. Generally, a nucleic acid encoding an immunoglobulin fusion protein may be isolated and inserted into a replicable vector for further cloning (amplification of the DNA) or for expression. DNA encoding the immunoglobulin fusion protein may be prepared by PCR amplification and sequenced using conventional procedures (e.g., by using oligonucleotide probes that are capable of binding specifically to nucleotides encoding Immunoglobulin fusion proteins). In an exemplary embodiment, nucleic acid encoding an immunoglobulin fusion protein is PCR amplified, restriction enzyme digested and gel purified. The digested nucleic acid may be inserted into a replicable vector. The replicable vector containing the digested immunoglobulin fusion protein insertion may be transformed or transduced into a host cell for further cloning (amplification of the DNA) or for expression. Host cells may be prokaryotic or eukaryotic cells.

Polynucleotide sequences encoding polypeptide components (e.g., immunoglobulin region, therapeutic peptide) of the immunoglobulin fusion proteins may be obtained by PCR amplification. Polynucleotide sequences may be isolated and sequenced from cells containing nucleic acids encoding the polypeptide components. Alternatively, or additionally, polynucleotides may be synthesized using nucleotide synthesizer or PCR techniques. Once obtained, sequences encoding the polypeptide components may be inserted into a recombinant vector capable of replicating and expressing heterologous polynucleotides in prokaryotic and/or eukaryotic hosts.

In addition, phage vectors containing replicon and control sequences that are compatible with the host microorganism may be used as transforming vectors in connection with these hosts. For example, bacteriophage such as λGEM™-11 may be utilized in making a recombinant vector which may be used to transform susceptible host cells such as *E. coli* LE392.

Immunoglobulin fusion proteins may be expressed intracellularly (e.g., cytoplasm) or extracellularly (e.g., secretion). For extracellular expression, the vector may comprise a secretion signal which enables translocation of the immunoglobulin fusion proteins to the outside of the cell.

Suitable host cells for cloning or expression of immunoglobulin fusion proteins-encoding vectors include prokaryotic or eukaryotic cells. The host cell may be a eukaryotic. Examples of eukaryotic cells include, but are not limited to, Human Embryonic Kidney (HEK) cell, Chinese Hamster Ovary (CHO) cell, fungi, yeasts, invertebrate cells (e.g., plant cells and insect cells), lymphoid cell (e.g., YO, NSO, Sp20 cell). Other examples of suitable mammalian host cell lines are monkey kidney CV1 line transformed by SV40 (COS-7); baby hamster kidney cells (BHK); mouse sertoli cells; monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; and FS4 cells. The host cell may be a prokaryotic cell (e.g., *E. coli*).

Host cells may be transformed with vectors containing nucleotides encoding an immunoglobulin fusion proteins. Transformed host cells may be cultured in media. The media may be supplemented with one or more agents for inducing promoters, selecting transformants, or amplifying or expressing the genes encoding the desired sequences. Methods for transforming host cells are known in the art and may include electroporation, calcium chloride, or polyethylene glycol/DMSO.

Alternatively, host cells may be transfected or transduced with vectors containing nucleotides encoding an immunoglobulin fusion proteins. Transfected or transduced host cells may be cultured in media. The media may be supplemented with one or more agents for inducing promoters, selecting transfected or transduced cells, or expressing genes encoding the desired sequences.

The expressed immunoglobulin fusion proteins may be secreted into and recovered from the periplasm of the host cells or transported into the culture media. Protein recovery from the periplasm may involve disrupting the host cell. Disruption of the host cell may comprise osmotic shock, sonication or lysis. Centrifugation or filtration may be used to remove cell debris or whole cells. The immunoglobulin fusion proteins may be further purified, for example, by affinity resin chromatography.

Alternatively, immunoglobulin fusion proteins that are secreted into the culture media may be isolated therein. Cells may be removed from the culture and the culture supernatant being filtered and concentrated for further purification of the proteins produced. The expressed polypeptides may be further isolated and identified using commonly known methods such as polyacrylamide gel electrophoresis (PAGE) and Western blot assay.

Immunoglobulin fusion proteins production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described herein. Cells may be grown for shorter periods prior to induction. Cells are usually induced for about 12-50 hours, although longer or shorter induction time may be used.

To improve the production yield and quality of the immunoglobulin fusion proteins disclosed herein, various fermentation conditions may be modified. For example, to improve the proper assembly and folding of the secreted immunoglobulin fusion proteins polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes may be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available.

Standard protein purification methods known in the art may be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, hydroxylapatite chromatography, gel electrophoresis, dialysis, and affinity chromatography and gel filtration using, for example, Sephadex G-75.

Immunoglobulin fusion proteins may be concentrated using a commercially available protein concentration filter, for example, an Amicon or Millipore Pellicon® ultrafiltration unit.

Protease inhibitors or protease inhibitor cocktails may be included in any of the foregoing steps to inhibit proteolysis of the immunoglobulin fusion proteins.

In some cases, an immunoglobulin fusion protein may not be biologically active upon isolation. Various methods for "refolding" or converting a polypeptide to its tertiary structure and generating disulfide linkages, may be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-mercaptoethanol (bME)/di-thio-b(ME). In many instances, a cosolvent may be used to increase the efficiency of the refolding, and common reagents used for this purpose include glycerol, polyethylene glycol of various molecular weights, arginine and the like.

Compositions

Disclosed herein are compositions comprising an immunoglobulin fusion protein and/or component of an immunoglobulin fusion protein disclosed herein. The compositions may comprise 1, 2, 3, 4, 5, 6, 7, 8, 9, 10 or more immunoglobulin fusion proteins. The immunoglobulin fusion proteins may be different. Alternatively, the immunoglobulin fusion proteins may be the same or similar. The immunoglobulin fusion proteins may comprise different immunoglobulin regions, therapeutic peptides or a combination thereof.

The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Compositions described herein may be formulated for controlled or sustained delivery in a manner that provides local concentration of the product (e.g., bolus, depot effect) and/or increased stability or half-life in a particular local environment. The compositions may comprise the formulation of immunoglobulin fusion proteins, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents. See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals.

The immunoglobulin fusion proteins disclosed herein may be microencapsulated.

A pharmaceutical composition disclosed herein can be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration.

Formulations suitable for intramuscular, subcutaneous, peritumoral, or intravenous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent can be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical composition described herein can be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

Alternatively or additionally, the compositions may be administered locally via implantation into the affected area of a membrane, sponge, or other appropriate material on to which an immunoglobulin fusion protein disclosed herein has been absorbed or encapsulated. Where an implantation device is used, the device may be implanted into any suitable tissue or organ, and delivery of an immunoglobulin fusion protein, nucleic acid, or vector disclosed herein may be directly through the device via bolus, or via continuous administration, or via catheter using continuous infusion.

A pharmaceutical composition comprising an immunoglobulin fusion protein disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations comprising an immunoglobulin fusion protein disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of an immunoglobulin fusion protein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size.

Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

The compositions disclosed herein may be useful for providing prognostic or providing diagnostic information.

"Pharmaceutically acceptable" may refer to approved or approvable by a regulatory agency of the Federal or a state government or listed in the U.S. Pharmacopeia or other generally recognized pharmacopeia for use in animals, including humans.

"Pharmaceutically acceptable salt" may refer to a salt of a compound that is pharmaceutically acceptable and that possesses the desired pharmacological activity of the parent compound.

"Pharmaceutically acceptable excipient, carrier or adjuvant" may refer to an excipient, carrier or adjuvant that may be administered to a subject, together with at least one immunoglobulin of the present disclosure, and which does not destroy the pharmacological activity thereof and is nontoxic when administered in doses sufficient to deliver a therapeutic amount of the compound.

"Pharmaceutically acceptable vehicle" may refer to a diluent, adjuvant, excipient, or carrier with which at least one immunoglobulin of the present disclosure is administered.

Kits

Further disclosed herein are kits which comprise one or more immunoglobulin fusion proteins or components thereof. The immunoglobulin fusion proteins may be packaged in a manner which facilitates their use to practice methods of the present disclosure. For example, a kit comprises an immunoglobulin fusion protein described herein packaged in a container with a label affixed to the container or a package insert that describes use of the immunoglobulin fusion protein in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The kit may comprise a container with an immunoglobulin fusion protein contained therein. The kit may comprise a container with (a) an immunoglobulin region of an immunoglobulin fusion protein. The kit may further comprise a package insert indicating that the first and second compositions may be used to treat a particular condition. Alternatively, or additionally, the kit may further comprise a second (or third) container comprising a pharmaceutically-acceptable buffer (e.g., bacteriostatic water for injection (BWFI), phosphate-buffered saline, Ringer's solution and dextrose solution). It may further comprise other materials desirable from a commercial and user standpoint, including, but not limited to, other buffers, diluents, filters, needles, and syringes. The immunoglobulin fusion protein may be packaged in a unit dosage form. The kit may further comprise a device suitable for administering the immunoglobulin fusion protein according to a specific route of administration or for practicing a screening assay. The kit may contain a label that describes use of the immunoglobulin fusion protein composition.

The composition comprising the immunoglobulin fusion protein may be formulated in accordance with routine procedures as a pharmaceutical composition adapted for intravenous administration to mammals, such as humans, bovines, felines, canines, and murines. Typically, compositions for intravenous administration comprise solutions in sterile isotonic aqueous buffer. Where necessary, the composition may also include a solubilizing agent and/or a local anaesthetics such as lignocaine to ease pain at the site of the injection. Generally, the ingredients may be supplied either separately or mixed together in unit dosage form. For example, the immunoglobulin fusion protein may be supplied as a dry lyophilized powder or water free concentrate in a hermetically sealed container such as an ampoule or sachette indicating the quantity of the immunoglobulin fusion protein. Where the composition is to be administered by infusion, it may be dispensed with an infusion bottle containing sterile pharmaceutical grade water or saline. Where the composition is administered by injection, an ampoule of sterile water for injection or saline may be provided so that the ingredients may be mixed prior to administration.

The amount of the composition described herein which will be effective in the treatment, inhibition and/or prevention of a disease or disorder associated with aberrant expression and/or activity of a therapeutic peptide may be determined by standard clinical techniques. In addition, in vitro assays may optionally be employed to help identify optimal dosage ranges. The precise dose to be employed in the formulation may also depend on the route of administration, and the seriousness of the disease or disorder, and should be decided according to the judgment of the practitioner and each patient's circumstances. Effective doses may be extrapolated from dose-response curves derived from in vitro, animal model test systems or clinical trials.

Therapeutic Use

Further disclosed herein are immunoglobulin fusion proteins for use in methods of treating, alleviating, inhibiting and/or preventing one or more diseases and/or conditions. The method may comprise administering to a subject in need thereof a composition comprising one or more immunoglobulin fusion proteins disclosed herein. The immunoglobulin fusion protein may comprise an immunoglobulin region attached to a therapeutic peptide. In some embodiments, the therapeutic peptide is attached the amino terminus of the immunoglobulin region. The immunoglobulin fusion protein may comprise an immunoglobulin region attached to a non-immunoglobulin region. The composition may further comprise a pharmaceutically acceptable carrier. The subject may be a mammal. The mammal may be a human. Alternatively, the mammal is a bovine. The therapeutic peptide may be a peptide or derivative or variant thereof. Alternatively, therapeutic peptide is a small molecule. The therapeutic peptide may be relaxin or derivative or variant thereof. The immunoglobulin region may comprise one or more immunoglobulin domains. The immunoglobulin region may be an immunoglobulin A, an immunoglobulin D, an immunoglobulin E, an immunoglobulin G, or an immunoglobulin M. The immunoglobulin region may be an immunoglobulin heavy chain region or fragment thereof. In some instances, the immunoglobulin region is from a mammalian immunoglobulin.

Alternatively, the immunoglobulin region is from a chimeric immunoglobulin. The immunoglobulin region may be from an engineered immunoglobulin or recombinant immunoglobulin. The immunoglobulin region may be from a humanized, human engineered or fully human immunoglobulin. The mammalian immunoglobulin may be a bovine immunoglobulin. The mammalian immunoglobulin may be a human immunoglobulin. In other instances, the mammalian immunoglobulin is a murine immunoglobulin. The immunoglobulin fusion protein, immunoglobulin region, and/or therapeutic peptide may further comprise one or more linkers. The linker may attach a proteolytic cleavage site to the immunoglobulin region or therapeutic peptide. The linker may be a connecting linker. The connecting linker may connect the therapeutic peptide to the amino terminus of the immunoglobulin region.

Further disclosed herein are immunoglobulin fusion proteins for use in methods of treating, alleviating, inhibiting and/or preventing one or more diseases and/or conditions. The method may comprise administering to a subject in need thereof a composition comprising one or more immunoglobulin fusion proteins disclosed herein. The immunoglobulin fusion protein may comprise an immunoglobulin region comprising a Palivizumab attached to a relaxin peptide, wherein the therapeutic peptide is attached the amino terminus of the immunoglobulin region. The immunoglobulin fusion protein may comprise a heavy chain fusion with an amino acid sequence selected from SEQ ID NO: 20 and 22 and a light chain with an amino acid sequence selected from SEQ ID NO: 10-12. The immunoglobulin fusion protein may comprise a heavy chain fusion with an amino acid sequence at least 70% identical to SEQ ID NO: 22 and a light chain with an amino acid sequence at least 70% identical to SEQ ID NO: 12. The immunoglobulin fusion protein may comprise a heavy chain fusion with an amino acid sequence at least 90% identical to SEQ ID NO: 22 and a light chain with an amino acid sequence at least 90% identical to SEQ ID NO: 12. The immunoglobulin fusion protein may comprise a heavy chain fusion with an amino acid sequence at least 95% identical to SEQ ID NO: 22 and a light chain with an amino acid sequence at least 95% identical to SEQ ID NO: 12. The immunoglobulin fusion protein may comprise a heavy chain fusion with an amino acid sequence at least 99% identical to SEQ ID NO: 22 and a light chain with an amino acid sequence at least 99% identical to SEQ ID NO: 12. The composition may further comprise a pharmaceutically acceptable carrier. The subject may be a mammal. The mammal may be a human. Alternatively, the mammal is a bovine.

The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. In some instances, the disease is heart related, for example, heart failure, acute coronary syndrome, atrial fibrillation, cardiac fibrosis, or coronary artery disease. In some embodiments, the heart failure is non-ischemic acute heart failure, chronic heart failure, acute decompensated heart failure, stable compensated heart failure, acute heart failure, or chronic heart failure. Additional non-limiting examples of disease and conditions include, ischemia reperfusion associated with solid organ transplant (e.g., lung, kidney, liver, heart), cardiopulmonary bypass for organ protection (e.g., renal), ischemic stroke, corneal healing (ocular administration), diabetic nephropathy, cirrhosis, portal hypertension, diabetic would healing, systemic sclerosis, cervical ripening at time of labor, preeclampsia, portal hypertension, and fibrosis.

In some embodiments, the therapeutic peptide is exendin-4 and the disease or condition is obesity, obesity related conditions, diabetes, and/or diabetes related conditions. In some embodiments, the therapeutic peptide is leptin and the disease or condition is obesity, obesity related conditions, diabetes, and/or diabetes related conditions. In some embodiments, the therapeutic peptide is glucagon and the disease or condition is obesity, obesity related conditions, diabetes, and/or diabetes related conditions. In some embodiments, the therapeutic peptide is a glucagon analog, for example ZP1, and the disease or condition is obesity, obesity related conditions, diabetes, and/or diabetes related conditions. In some embodiments, the therapeutic peptide is insulin, and the disease or condition is obesity, obesity related conditions, diabetes, and/or diabetes related conditions. In some embodiments, the therapeutic peptide is oxyntomodulin, and the disease or condition is obesity, obesity related conditions, diabetes, and/or diabetes related conditions. In some embodiments, the therapeutic peptide is a glucagon like protein, for example GLP-1 or GLP-2, and the disease or condition is obesity, obesity related conditions, diabetes, and/or diabetes related conditions.

In some embodiments, the therapeutic peptide is relaxin and the disease or condition is heart failure, heart failure related conditions, fibrosis, fibrosis related conditions, or other disease. Relaxin includes relaxin2 and relaxins comprising internal linkers such as relaxin2 (XT100), relaxin2 (XT35), relaxin2 (single), relaxin2 (insulin C peptide), relaxin2 (XT21), relaxin2 (30GS), relaxin2 (9GS), and relaxin2 (GGGPRR). In some embodiments, the therapeutic peptide is relaxin and the disease or condition is heart failure, acute coronary syndrome, atrial fibrillation, cardiac fibrosis, or coronary artery disease. In some embodiments, the therapeutic peptide is relaxin and the disease or condition is ischemia reperfusion associated with solid organ transplant (e.g., lung, kidney, liver, heart), cardiopulmonary bypass for organ protection (e.g., renal), ischemic stroke, corneal healing (ocular administration), diabetic nephropathy, cirrhosis, portal hypertension, diabetic would healing, systemic sclerosis, cervical ripening at time of labor, preeclampsia, portal hypertension, or fibrosis. In some embodiments, heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure. In some embodiments, the therapeutic peptide is relaxin and the disease or condition is cardiovascular disease, lung disease, fibrotic disease, kidney disease, pancreatitis, inflammation, cancer, scleroderma, pulmonary fibrosis, renal fibrosis, hepatic fibrosis, fibrosis of the lung, heart, kidney, bone marrow, liver, dermatological fibrosis, fibrotic eye disorder, ischemia, Alzheimer's disease, corneal injury, neurodegenerative disease, cardiovascular disease, fibrotic disease, failure, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, respiratory disorders, chronic obstructive pulmonary disease, chronic bronchitis, interstitial lung disease, asthma, pulmonary emphysema, bronchiectases, cystic fibrosis (mucoviscidosis) and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstistial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematosus, rheumatic immunological systemic diseases, renal artery stenosis, renal artery thrombosis, renal vein thrombosis, analgetics induced nephropathy, polycystic kidney disease, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD-associated pulmonary hypertension, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, pulmonary emphysema induced by cigarette smoke, cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, hypertension, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, or hypercholesterolemia.

The disease and/or condition may be a chronic disease or condition. Alternatively, the disease and/or condition is an acute disease or condition. The disease or condition may be recurrent, refractory, accelerated, or in remission. The disease or condition may affect one or more cell types. The one or more diseases and/or conditions may be an autoimmune disease, inflammatory disease, cardiovascular disease, metabolic disorder, pregnancy, and cell proliferative disorder.

The disease or condition may be an autoimmune disease. In some cases, the autoimmune disease may be scleroderma, diffuse scleroderma or systemic scleroderma.

The disease or condition may be an inflammatory disease. In some cases, the inflammatory disease may be hepatitis, fibromyalgia or psoriasis.

The disease or condition may be a rheumatic disease. In some cases, the rheumatic disease may be Ankylosing spondylitis, back pain, bursitis, tendinitis, shoulder pain, wrist pain, bicep pain, leg pain, knee pain, ankle pain, hip pain, Achilles pain, Capsulitis, neck pain, osteoarthritis, systemic lupus, erythematosus, rheumatoid arthritis, juvenile arthritis, Sjögren syndrome, Polymyositis, Behçet's disease, Reiter's syndrome, or Psoriatic arthritis. The rheumatic disease may be chronic. Alternatively, the rheumatic disease is acute.

The disease or condition may be a cardiovascular disease. In some cases, the cardiovascular disease may be acute heart failure, congestive heart failure, compensated heart failure, decompensated heart failure, hypercholesterolemia, atherosclerosis, coronary heart disease or ischemic stroke. The cardiovascular disease may be cardiac hypertrophy.

The disease or condition may be a metabolic disorder. In some cases, the metabolic disorder may be hypercholesterolemia, hypobetalipoproteinemia, hypertriglyceridemia, hyperlipidemia, dyslipidemia, ketosis, hypolipidemia, refractory anemia, appetite control, gastric emptying, non-alcoholic fatty liver disease, obesity, type I diabetes mellitus, type II diabetes mellitus, gestational diabetes mellitus, metabolic syndrome. The metabolic disorder may be type I diabetes. The metabolic disorder may be type II diabetes.

The disease or condition may be pregnancy. The immunoglobulin fusion proteins may be used to treat preeclampsia or induce labor.

Disclosed herein are methods of treating a disease or condition in a subject in need thereof, the method comprising administering to the subject a composition comprising an immunoglobulin fusion protein disclosed herein. In some embodiments, the immunoglobulin fusion protein comprises a therapeutic peptide attached to an immunoglobulin region. In some embodiments, the therapeutic peptide is attached to the immunoglobulin region via a chemical linker referred to as a connecting peptide. In some embodiments, the therapeutic peptide is attached to the amino terminus of the immunoglobulin region. In some embodiments, the therapeutic peptide is relaxin. In some embodiments, the immunoglobulin fusion protein comprises an immunoglobulin region comprising a Palivizumab attached to a relaxin peptide, wherein the therapeutic peptide is attached the amino terminus of the immunoglobulin region. In some embodiments, the immunoglobulin fusion protein comprises a heavy chain fusion with an amino acid sequence selected from SEQ ID NO: 20 and 22 and a light chain with an amino acid sequence selected from SEQ ID NO: 10-12. In some embodiments, the immunoglobulin fusion protein comprises a heavy chain fusion with an amino acid sequence at least 70% identical to SEQ ID NO: 22 and a light chain with an amino acid sequence at least 70% identical to SEQ ID NO: 12. In some embodiments, the immunoglobulin fusion protein comprises a heavy chain fusion with an amino acid sequence at least 90% identical to SEQ ID NO: 22 and a light chain with an amino acid sequence at least 90% identical to SEQ ID NO: 12. In some embodiments, the immunoglobulin fusion protein comprises a heavy chain fusion with an amino acid sequence at least 95% identical to SEQ ID NO: 22 and a light chain with an amino acid sequence at least 95% identical to SEQ ID NO: 12. In some embodiments, the immunoglobulin fusion protein comprises a heavy chain fusion with an amino acid sequence at least 99% identical to SEQ ID NO: 22 and a light chain with an amino acid sequence at least 99% identical to SEQ ID NO: 12. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The immunoglobulin fusion protein may be used to treat preeclampsia or induce labor. In some embodiments, heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure. In some embodiments, the immunoglobulin fusion protein may be used to treat a disease selected from the group consisting of cardiovascular disease, lung disease, fibrotic disease, kidney disease, pancreatitis, inflammation, cancer, scleroderma, pulmonary fibrosis, renal fibrosis, hepatic fibrosis, fibrosis of the lung, heart, kidney, bone marrow, liver, dermatological fibrosis, fibrotic eye disorder, ischemia, Alzheimer's disease, corneal injury, neurodegenerative disease, cardiovascular disease, fibrotic disease, failure, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, respiratory disorders, chronic obstructive pulmonary disease, chronic bronchitis, interstitial lung disease, asthma, pulmonary emphysema, bronchiectases, cystic fibrosis (mucoviscidosis) and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstistial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematosus, rheumatic immunological systemic diseases, renal artery stenosis, renal artery thrombosis, renal vein thrombosis, analgetics induced nephropathy, polycystic kidney disease, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD-associated pulmonary hypertension, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, pulmonary emphysema induced by cigarette smoke, cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, hypertension, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia.

Disclosed herein may be a method of preventing or treating a disease or condition in a subject in need thereof comprising administering to the subject a composition comprising one or more immunoglobulin fusion proteins disclosed herein. The immunoglobulin fusion protein may comprise an immunoglobulin region attached to therapeutic peptide. The immunoglobulin fusion protein may comprise one or more immunoglobulin heavy chains, light chains, or a combination thereof. The immunoglobulin fusion protein sequence may share 50%, 60%, 70%, 80%, 85%, 90%, 95%, 97%, 99%, or more amino acid sequence identity to a heavy chain sequence provided by SEQ ID NOs: 20-22. The immunoglobulin fusion protein sequence may share 50%, 60%, 70%, 80%, 85%, 90%, 95%, 97%, 99%, or more amino acid sequence identity to a heavy chain sequence provided by SEQ ID NO: 22. The immunoglobulin fusion protein sequence may share 50%, 60%, 70%, 80%, 85%, 90%, 95%, 97%, 99%, or more amino acid sequence identity to a light chain sequence provided by SEQ ID NOs: 9-12. The immunoglobulin fusion protein sequence may share 50%, 60%, 70%, 80%, 85%, 90%, 95%, 97%, 99%, or more amino acid sequence identity to a light chain sequence provided by SEQ ID NO: 12. The immunoglobulin heavy chain may be encoded by a nucleotide sequence that is at least about 50%, 60%, 70%, 80%, 85%, 90%, 95%, 97%, 99%, or more homologous to SEQ ID NOs: 17-19. The immunoglobulin heavy chain may be encoded by a nucleotide sequence that is at least about 50%, 60%, 70%, 80%, 85%, 90%, 95%, 97%, 99%, or more homologous to SEQ ID NO: 19. The immunoglobulin light chain may be encoded by a nucleotide sequence that is at least about 50%, 60%, 70%, 80%, 85%, 90%, 95%, 97%, 99%, or more homologous to SEQ ID NOs: 1-4. The immunoglobulin light chain may be encoded by a nucleotide sequence that is at least about 50%, 60%, 70%, 80%, 85%, 90%, 95%, 97%, 99%, or more homologous to SEQ ID NO: 4. The immunoglobulin fusion protein may further comprise one or more linkers. The immunoglobulin fusion protein may further comprise one or more internal linkers. The immunoglobulin fusion protein may further comprise one or more proteolytic cleavage sites. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. The disease or condition may be a blood disorder. In some instances, the disease or condition may be obesity, diabetes, osteoporosis, anemia, or pain. In some embodiments, the disease or condition is heart failure, acute coronary syndrome, atrial fibrillation, cardiac fibrosis, or coronary artery disease. In some embodiments, the disease or condition is ischemia reperfusion associated with solid organ transplant (e.g., lung, kidney, liver, heart), cardiopulmonary bypass for organ protection (e.g., renal), ischemic stroke, corneal healing (ocular administration), diabetic nephropathy, cirrhosis, portal hypertension, diabetic would healing, systemic sclerosis, cervical ripening at time of labor, preeclampsia, portal hypertension, or fibrosis. In some embodiments, the disease or condition may be heart failure. Said heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure. In some embodiments, the disease or condition is cardiovascular disease, lung disease, fibrotic disease, kidney disease, pancreatitis, inflammation, cancer, scleroderma, pulmonary fibrosis, renal fibrosis, hepatic fibrosis, fibrosis of the lung, heart, kidney, bone marrow, liver, dermatological fibrosis, fibrotic eye disorder, ischemia, Alzheimer's disease, corneal injury, neurodegenerative disease, cardiovascular disease, fibrotic disease, failure, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, respiratory disorders, chronic obstructive pulmonary disease, chronic bronchitis, interstitial lung disease, asthma, pulmonary emphysema, bronchiectases, cystic fibrosis (mucoviscidosis) and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstistial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematosus, rheumatic immunological systemic diseases, renal artery stenosis, renal artery thrombosis, renal vein thrombosis, analgetics induced nephropathy, polycystic kidney disease, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD-associated pulmonary hypertension, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, pulmonary emphysema induced by cigarette smoke, cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, hypertension, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, or hypercholesterolemia.

Disclosed herein is a method of preventing or treating heart failure in a subject in need thereof comprising administering to the subject a composition comprising one or more immunoglobulin fusion proteins described herein, wherein the immunoglobulin fusion protein comprises a heavy chain fusion having an amino acid sequence at least 90% identical to SEQ ID NOs: 20 or 22 and a light chain having an amino acid sequence at least 90% identical to SEQ ID NOs: 10-12. In some embodiments, the immunoglobulin fusion protein comprises a heavy chain fusion having an amino acid sequence at least 90% identical to SEQ ID NOs: 22 and a light chain having an amino acid sequence at least 90% identical to SEQ ID NOs: 12. The composition may further comprise a pharmaceutically acceptable carrier. The subject may be a mammal. The mammal may be a human. The heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure.

Provided are methods of treatment, inhibition and prevention of a disease or condition in a subject in need thereof by administration to the subject of an effective amount of an immunoglobulin fusion protein or pharmaceutical composition described herein. The immunoglobulin fusion protein may be substantially purified (e.g., substantially free from substances that limit its effect or produce undesired side-effects). The subject may be an animal, including but not limited to animals such as cows, pigs, sheep, goats, rabbits, horses, chickens, cats, dogs, mice, etc. The subject may be a mammal. The subject may be a human. The subject may be a non-human primate. Alternatively, the subject may be a bovine. The subject may be an avian, reptile or amphibian.

Methods of treatment disclosed herein comprise administering an immunoglobulin fusion protein comprises an immunoglobulin region comprising a Palivizumab attached to a relaxin peptide, wherein the therapeutic peptide is attached the amino terminus of the immunoglobulin region according to a schedule. In some embodiments, the immunoglobulin fusion protein is administered twice per week. In some embodiments, the immunoglobulin fusion protein is administered once per week. In some embodiments, the immunoglobulin fusion protein is administered once per two weeks. In some embodiments, the immunoglobulin fusion protein is administered four times per month. In some embodiments, the immunoglobulin fusion protein is administered three times per month. In some embodiments, the immunoglobulin fusion protein is administered once per month. In some embodiments, the immunoglobulin fusion protein is administered in an infusion lasting an indicated amount of time. In some embodiments, the immunoglobulin fusion protein is administered for six hours. In some embodiments, the immunoglobulin fusion protein is administered for five hours. In some embodiments, the immunoglobulin fusion protein is administered for four hours. In some embodiments, the immunoglobulin fusion protein is administered for three hours. In some embodiments, the immunoglobulin fusion protein is administered for two hours. In some embodiments, the immunoglobulin fusion protein is administered for one hour. In some embodiments, the immunoglobulin fusion protein is administered subcutaneously. In some embodiments, the immunoglobulin fusion protein is administered intramuscularly. In some embodiments, the immunoglobulin fusion protein is administered intravenously.

Additional Uses

Further disclosed herein are uses of an immunoglobulin fusion protein in the manufacture of a medicament for the treatment of a disease or condition. The immunoglobulin fusion protein may be any of the immunoglobulin fusion proteins disclosed herein. Disclosed herein is the use of an immunoglobulin fusion protein in the manufacture of a medicament for the treatment of a disease or condition, the immunoglobulin fusion protein comprising an immunoglobulin region attached to a therapeutic peptide. In some embodiments, the therapeutic peptide is attached to the amino terminus of an immunoglobulin region. Further disclosed herein is the use of an immunoglobulin fusion protein in the manufacture of a medicament for the treatment of a disease or condition, the immunoglobulin fusion protein comprising an immunoglobulin region attached to a therapeutic peptide. In some embodiments, the therapeutic peptide is attached to the amino terminus of an immunoglobulin region. The immunoglobulin fusion protein may comprise one or more internal linkers, one or more protease cleavage sites, one or more connecting peptides, and any combination thereof. The one or more internal linkers, one or more protease cleavage sites, and/or one or more connecting peptides may be inserted within the immunoglobulin region. The one or more internal linkers, one or more protease cleavage sites, and/or one or more connecting peptides may be inserted within the therapeutic peptide. The one or more internal linkers, one or more protease cleavage sites, and/or one or more connecting peptides may be connected to the amino terminus of the immunoglobulin region. The immunoglobulin region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be an immunoglobulin light chain region or fragment thereof. The immunoglobulin domain may be from an anti-viral, anti-bacterial, anti-parasitic, and/or anti-fungal immunoglobulin. In some instances, the immunoglobulin domain is from a mammalian immunoglobulin. Alternatively, the immunoglobulin domain is from a chimeric immunoglobulin. The immunoglobulin domain may be from an engineered immunoglobulin or recombinant immunoglobulin. The immunoglobulin domain may be from a humanized, human engineered or fully human immunoglobulin. The mammalian immunoglobulin may be a bovine immunoglobulin. The mammalian immunoglobulin may be a human immunoglobulin. In other instances, the mammalian immunoglobulin is a murine immunoglobulin. The therapeutic peptide may be a peptide or derivative or variant thereof. The therapeutic peptide may comprise relaxin. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder. In some embodiments, the disease or condition is heart failure, acute coronary syndrome, atrial fibrillation, cardiac fibrosis, or coronary artery disease. In some embodiments, the disease or condition is ischemia reperfusion associated with solid organ transplant (e.g., lung, kidney, liver, heart), cardiopulmonary bypass for organ protection (e.g., renal), ischemic stroke, corneal healing (ocular administration), diabetic nephropathy, cirrhosis, portal hypertension, diabetic would healing, systemic sclerosis, cervical ripening at time of labor, preeclampsia, portal hypertension, or fibrosis.

Disclosed herein are uses of an immunoglobulin fusion protein in the manufacture of a medicament for the treatment of a disease or condition. In some embodiments, the immunoglobulin fusion protein comprises a therapeutic peptide attached to an immunoglobulin region. In some embodiments, the therapeutic peptide is attached to the immunoglobulin region via a chemical linker referred to as a connecting peptide. In some embodiments, the therapeutic peptide is attached to the amino terminus of the immunoglobulin region. In some embodiments, the therapeutic peptide is relaxin. In some embodiments, the immunoglobulin fusion protein comprises an immunoglobulin region comprising a Palivizumab attached to a relaxin peptide, wherein the therapeutic peptide is attached the amino terminus of the immunoglobulin region. In some embodiments, the immunoglobulin fusion protein comprises a heavy chain fusion with an amino acid sequence selected from SEQ ID NO: 20 and 22 and a light chain with an amino acid sequence selected from SEQ ID NO: 10-12. In some embodiments, the immunoglobulin fusion protein comprises a heavy chain fusion with an amino acid sequence at least 70% identical to SEQ ID NO: 22 and a light chain with an amino acid sequence at least 70% identical to SEQ ID NO: 12. In some embodiments, the immunoglobulin fusion protein comprises a heavy chain fusion with an amino acid sequence at least 90% identical to SEQ ID NO: 22 and a light chain with an amino acid sequence at least 90% identical to SEQ ID NO: 12. In some embodiments, the immunoglobulin fusion protein comprises a heavy chain fusion with an amino acid sequence at least 95% identical to SEQ ID NO: 22 and a light chain with an amino acid sequence at least 95% identical to SEQ ID NO: 12. In some embodiments, the immunoglobulin fusion protein comprises a heavy chain fusion with an amino acid sequence at least 99% identical to SEQ ID NO: 22 and a light chain with an amino acid sequence at least 99% identical to SEQ ID NO: 12. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The immunoglobulin fusion protein may be used to treat preeclampsia or induce labor. In some embodiments, heart failure may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure. In some embodiments, the immunoglobulin fusion protein may be used to treat a disease selected from the group consisting of cardiovascular disease, lung disease, fibrotic disease, kidney disease, pancreatitis, inflammation, cancer, scleroderma, pulmonary fibrosis, renal fibrosis, hepatic fibrosis, fibrosis of the lung, heart, kidney, bone marrow, liver, dermatological fibrosis, fibrotic eye disorder, ischemia, Alzheimer's disease, corneal injury, neurodegenerative disease, cardiovascular disease, fibrotic disease, failure, pancreatitis, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, edemas, ischemias, myocardial infarction, stroke, transient ischemic attack, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, catheter examinations and other surgical procedures, respiratory disorders, chronic obstructive pulmonary disease, chronic bronchitis, interstitial lung disease, asthma, pulmonary emphysema, bronchiectases, cystic fibrosis (mucoviscidosis) and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstistial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematosus, rheumatic immunological systemic diseases, renal artery stenosis, renal artery thrombosis, renal vein thrombosis, analgetics induced nephropathy, polycystic kidney disease, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD-associated pulmonary hypertension, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, pulmonary emphysema induced by cigarette smoke, cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, hypertension, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia.

Disclosed herein is the use of an immunoglobulin fusion protein in the manufacture of a medicament for the treatment of a cardiovascular disease or condition. The immunoglobulin fusion protein may be any of the immunoglobulin fusion proteins disclosed herein. The immunoglobulin fusion protein may comprise an immunoglobulin region attached to one or more therapeutic peptides. In some embodiments, the therapeutic peptide is attached the amino terminus of the immunoglobulin region. The cardiovascular disease or condition may be acute heart failure. The cardiovascular disease or condition may be cardiac hypertrophy. The immunoglobulin region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be an immunoglobulin light chain region or fragment thereof. The immunoglobulin domain may be from an anti-viral, anti-bacterial, anti-parasitic, and/or anti-fungal immunoglobulin. In some instances, the immunoglobulin domain is from a mammalian immunoglobulin. Alternatively, the immunoglobulin domain is from a chimeric immunoglobulin. The immunoglobulin domain may be from an engineered immunoglobulin or recombinant immunoglobulin. The immunoglobulin domain may be from a humanized, human engineered or fully human immunoglobulin. The mammalian immunoglobulin may be a bovine immunoglobulin. The mammalian immunoglobulin may be a human immunoglobulin. In other instances, the mammalian immunoglobulin is a murine immunoglobulin. The immunoglobulin fusion protein, immunoglobulin region and/or therapeutic peptide may further comprise one or more linkers. The linker may attach the therapeutic peptide to the immunoglobulin region. The therapeutic peptide may be a peptide or derivative or variant thereof. Alternatively, therapeutic peptide is a small molecule. The therapeutic peptide may be relaxin.

Disclosed herein is the use of an immunoglobulin fusion protein in the manufacture of a medicament for the treatment of a cardiovascular disease or condition, wherein the immunoglobulin fusion protein comprises a heavy chain fusion having an amino acid sequence at least 90% identical to SEQ ID NOs: 20 or 22 and a light chain having an amino acid sequence at least 90% identical to SEQ ID NOs: 10-12. In some embodiments, the immunoglobulin fusion protein comprises a heavy chain fusion having an amino acid sequence at least 90% identical to SEQ ID NOs: 22 and a light chain having an amino acid sequence at least 90% identical to SEQ ID NOs: 12. The composition may further comprise a pharmaceutically acceptable carrier. The subject may be a mammal. The mammal may be a human. The cardiovascular disease may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure.

Further disclosed herein are uses of an immunoglobulin fusion protein for the treatment of a disease or condition. Disclosed herein is the use of an immunoglobulin fusion protein for the treatment of a disease or condition in a subject in need thereof. The immunoglobulin fusion protein may be any of the immunoglobulin fusion proteins disclosed herein. The immunoglobulin fusion protein may comprise an immunoglobulin region attached to one or more therapeutic peptides. In some embodiments, the therapeutic peptide is attached the amino terminus of the immunoglobulin region. The immunoglobulin region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be an immunoglobulin light chain region or fragment thereof. The immunoglobulin domain may be from an anti-viral, anti-bacterial, anti-parasitic, and/or anti-fungal immunoglobulin. In some instances, the immunoglobulin domain is from a mammalian immunoglobulin. Alternatively, the immunoglobulin domain is from a chimeric immunoglobulin. The immunoglobulin domain may be from an engineered immunoglobulin or recombinant immunoglobulin. The immunoglobulin domain may be from a humanized, human engineered or fully human immunoglobulin. The mammalian immunoglobulin may be a bovine immunoglobulin. The mammalian immunoglobulin may be a human immunoglobulin. In other instances, the mammalian immunoglobulin is a murine immunoglobulin. The immunoglobulin fusion protein, immunoglobulin region and/or therapeutic peptide may further comprise one or more linkers. The linker may attach therapeutic peptide to the immunoglobulin region. The therapeutic peptide may be a peptide or derivative or variant thereof. The therapeutic peptide may be relaxin. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder.

Disclosed herein is the use of an immunoglobulin fusion protein for the treatment of a cardiovascular disease or condition in a subject in need thereof. In some embodiments, the immunoglobulin fusion protein treats a disease or condition selected from heart failure, acute coronary syndrome, atrial fibrillation, cardiac fibrosis, and coronary artery disease. The immunoglobulin fusion protein may be any of the immunoglobulin fusion proteins disclosed herein. The immunoglobulin fusion protein may comprise an immunoglobulin region attached to one or more therapeutic peptides. In some embodiments, the therapeutic peptide is attached the amino terminus of the immunoglobulin region. The cardiovascular disease or condition may be acute heart failure. The cardiovascular disease or condition may be cardiac hypertrophy. The immunoglobulin region may comprise one or more immunoglobulin domains. The immunoglobulin domain may be an immunoglobulin A, an immunoglobulin D, an immunoglobulin E, an immunoglobulin G, or an immunoglobulin M. The immunoglobulin domain may be an immunoglobulin heavy chain region or fragment thereof. The immunoglobulin domain may be an immunoglobulin light chain region or fragment thereof. The immunoglobulin domain may be from an anti-viral, anti-bacterial, anti-parasitic, and/or anti-fungal immunoglobulin. In some instances, the immunoglobulin domain is from a mammalian immunoglobulin. Alternatively, the immunoglobulin domain is from a chimeric immunoglobulin. The immunoglobulin domain may be from an engineered immunoglobulin or recombinant immunoglobulin. The immunoglobulin domain may be from a humanized, human engineered or fully human immunoglobulin. The mammalian immunoglobulin may be a bovine immunoglobulin. The mammalian immunoglobulin may be a human immunoglobulin. In other instances, the mammalian immunoglobulin is a murine immunoglobulin. The immunoglobulin fusion protein, immunoglobulin region and/or therapeutic peptide may further comprise one or more linkers. The linker may attach the therapeutic peptide to the immunoglobulin region. The therapeutic peptide may be a peptide or derivative or variant thereof. The therapeutic peptide may be relaxin.

Disclosed herein is the use of an immunoglobulin fusion protein for the treatment of a cardiovascular disease or condition in a subject in need thereof, wherein the immunoglobulin fusion protein comprises a heavy chain fusion having an amino acid sequence at least 90% identical to SEQ ID NOs: 20 or 22 and a light chain having an amino acid sequence at least 90% identical to SEQ ID NOs: 10-12. In some embodiments, the immunoglobulin fusion protein comprises a heavy chain fusion having an amino acid sequence at least 90% identical to SEQ ID NOs: 22 and a light chain having an amino acid sequence at least 90% identical to SEQ ID NOs: 12. The composition may further comprise a pharmaceutically acceptable carrier. The subject may be a mammal. The mammal may be a human. The cardiovascular disease may comprise one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure.

Pharmacological Properties

Further disclosed herein are methods of improving one or more pharmacological properties of a therapeutic peptide. The method may comprise producing an immunoglobulin fusion protein disclosed herein. Examples of pharmacological properties may include, but are not limited to, half-life, stability, solubility, immunogenicity, toxicity, bioavailability, absorption, liberation, distribution, metabolization, and excretion. Liberation may refer to the process of releasing of a therapeutic peptide from the pharmaceutical formulation. Absorption may refer to the process of a substance entering the blood circulation. Distribution may refer to the dispersion or dissemination of substances throughout the fluids and tissues of the body. Metabolization (or biotransformation, or inactivation) may refer to the recognition by an organism that a foreign substance is present and the irreversible transformation of parent compounds into daughter metabolites. Excretion may refer to the removal of the substances from the body.

The half-life of a therapeutic peptide may greater than the half-life of the non-conjugated therapeutic peptide. The half-life of the therapeutic peptide may be greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. The half-life of the therapeutic peptide may be greater than 4 hours when administered to a subject. The half-life of the therapeutic peptide may be greater than 6 hours when administered to a subject.

The half-life of the therapeutic peptide may increase by at least about 2, 4, 6, 8, 10, 12, 14, 16, 18, or 20 or more hours. The half-life of the therapeutic peptide may increase by at least about 2 hours. The half-life of the therapeutic peptide may increase by at least about 4 hours. The half-life of the therapeutic peptide may increase by at least about 6 hours. The half-life of the therapeutic peptide may increase by at least about 8 hours.

The half-life of a therapeutic peptide may be at least about 1.5, 2, 2.5, 3, 3.5, 4, 4.5, 5, 5.5, 6, 6.5, 7, 7.5, 8, 8.5, 9, 9.5, or 10-fold greater than the half-life of the non-conjugated therapeutic peptide. The half-life of a therapeutic peptide an immunoglobulin described herein may be at least about 15, 16, 17, 18, 19, 20, 25, 30, 35, 40, 45, or 50-fold greater than the half-life of the non-conjugated therapeutic peptide. The half-life of a therapeutic peptide an immunoglobulin described herein may be at least about 2-fold greater than the half-life of the non-conjugated therapeutic peptide. The half-life of a therapeutic peptide an immunoglobulin described herein may be at least about 5-fold greater than the half-life of the non-conjugated therapeutic peptide. The half-life of a therapeutic peptide an immunoglobulin described herein may be at least about 10-fold greater than the half-life of the non-conjugated therapeutic peptide.

The half-life of a therapeutic peptide an immunoglobulin described herein may be at least about 5%, 10%, 15%, 20%, 25%, 30%, 35%, 40%, 45%, 55%, 60%, 65%, 70%, 75%, 80%, 85%, 90%, 95%, or 97% greater than the half-life of the non-conjugated therapeutic peptide. The half-life of a therapeutic peptide an immunoglobulin described herein may be at least about 10% greater than the half-life of the non-conjugated therapeutic peptide. The half-life of a therapeutic peptide an immunoglobulin described herein may be at least about 20% greater than the half-life of the non-conjugated therapeutic peptide. The half-life of a therapeutic peptide an immunoglobulin described herein may be at least about 30% greater than the half-life of the non-conjugated therapeutic peptide. The half-life of a therapeutic peptide an immunoglobulin described herein may be at least about 40% greater than the half-life of the non-conjugated therapeutic peptide. The half-life of a therapeutic peptide an immunoglobulin described herein may be at least about 50% greater than the half-life of the non-conjugated therapeutic peptide.

EXAMPLES

The activity data provided in the following examples are generally obtained using the immunoglobulin fusion proteins defined in the example and exemplified by the provided SEQ ID. It is to be understood that the activities of any immunoglobulin fusion protein disclosed herein may be enhanced or attenuated depending on conditions not relating to immunoglobulin fusion protein sequence, for example, expression and purification conditions.

Example 1: Construction of Palivizumab-Relaxin Fusion Protein Vectors for Expression in Mammalian Cells Relaxin nucleic acid sequences were synthesized by IDT (IA, USA), and amplified by polymerase chain reaction (PCR).

The relaxin2 (9GS) (SEQ ID NO: 33) was genetically fused to nucleic acids encoding for a palivizumab heavy chains 1, 2 or 3 (SEQ ID NOs: 6, 7, 8, respectively) using a connecting nucleic acid sequence encoding for the connecting peptide 16GS (SEQ ID NO: 60) by overlap PCR to generate palivizumab(NH1, 2, or 3, 16GS)-relaxin2(9GS) (SEQ ID NOs: 18, 18, 19, respectively). The pPalivizumab (NH1, 2, or 3, 16GS)-relaxin2(9GS) mammalian expression vectors encoding for palivizumab(NH1, 2, or 3, 16GS)-relaxin2(9GS) were created by in-frame ligation of the amplified palivizumab(NH1, 2, or 3, 16GS)-relaxin2(9GS) to the pFuse backbone vector (InvivoGen, CA).

The gene encoding for palivizumab light chain (SEQ ID NO: 1) was amplified and closed into the pFuse vector to generate a pPalivizumab(L) mammalian expression vector. The resulting mammalian expression vectors were verified by DNA sequencing.

Example 2: Expression and Purification of Palivizumab-Relaxin Fusion Proteins

Figure 1B:
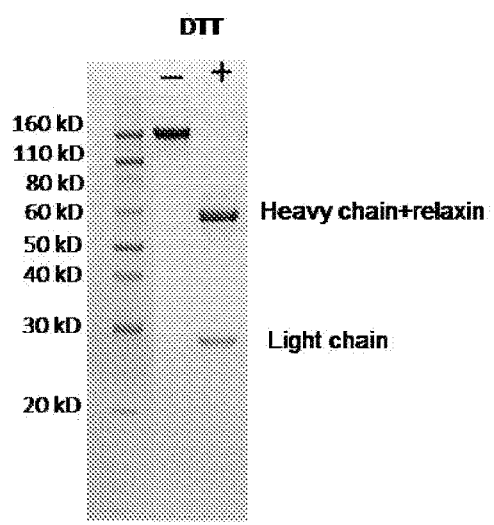
Figure 1C:
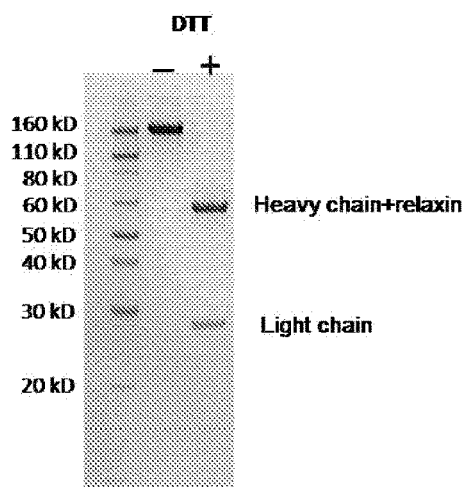

Palivizumab-relaxin heavy chain fusion proteins were each expressed through co-transfection of freestyle HEK293 cells with palivizumab-relaxin heavy chain mammalian expression vectors described in Example 1 and a palivizumab light chain mammalian expression vector. The cells were grown in shaker flasks at 125 rpm with freestyle 293 expression medium (Life Technologies) at 37° C. with 5% CO2. Expressed proteins were secreted into the culture medium and harvested twice every 48 hours after transfection. The fusion proteins were purified by Protein A/G chromatography (Thermo Fisher Scientific, IL) and analyzed by SDS-PAGE gel. Purified heavy chain fusion proteins expressed with palivizumab light chain are shown in the SDS-PAGE gels of FIG. 1A, FIG. 1B, and FIG. 1C. For each gel, the first lane corresponds to a molecular marker, the second lane corresponds to purified protein, and the third lane corresponds to purified protein treated with the reducing agent DTT. FIG. 1A shows purified palivizumab(NH1, 16GS)-relaxin2(9GS) (SEQ ID NO: 20) and palivizumab L (SEQ ID NO: 9), collectively, SCX1. FIG. 1B shows purified palivizumab(NH2, 16GS)-relaxin2(9GS) (SEQ ID NO: 21) and palivizumab L (SEQ ID NO: 9), collectively, SCX2. FIG. 1C shows purified palivizumab(NH3, 16GS)-relaxin2 (9GS) (SEQ ID NO: 22) and palivizumab L (SEQ ID NO: 9), collectively, SCX3.

Example 3: Activity of Palivizumab-Relaxin Fusion Proteins to Activate Relaxin Receptors The activities of palivizumab-relaxin fusion proteins purified in Example 2 were examined by a luciferase assay. HEK293 cells overexpressed with relaxin receptor (LGR7) and cAMP responsive element (CRE)-luciferase (Luc) reporter gene were grown in DMEM supplemented with 10% FBS at 37° C. with 5% CO2. Cells were seeded in 384-well plates for 24 hours and subsequently independently treated with various concentrations of palivizumab-relaxin fusion proteins purified from Example 2 (SCX1, SCX2, or SCX3) or relaxin2 peptide for an additional 24 hours. Luminescence intensities were then measured using One-Glo (Promega) luciferase reagent by following manufacturer's instruction. The $EC_{50}$ values were determined by fitting data into a logistic sigmoidal function: y=A2+(A1-A2)/(1+ (x/x0)p), where A1 is the initial value, A2 is the final value, x0 is the inflection point of the curve, and p is the power. The $EC_{50}$ for relaxin-2 was 22.3 pM.

Figure 2A:
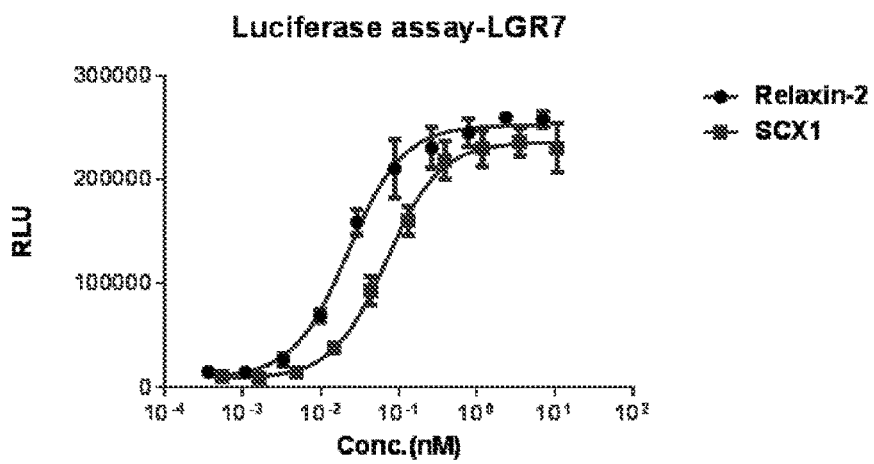
FIG. 2A, FIG. 2B, and FIG. 2C depict graphs of the activities of palivizumab-relaxin fusion proteins.
Figure 2B:
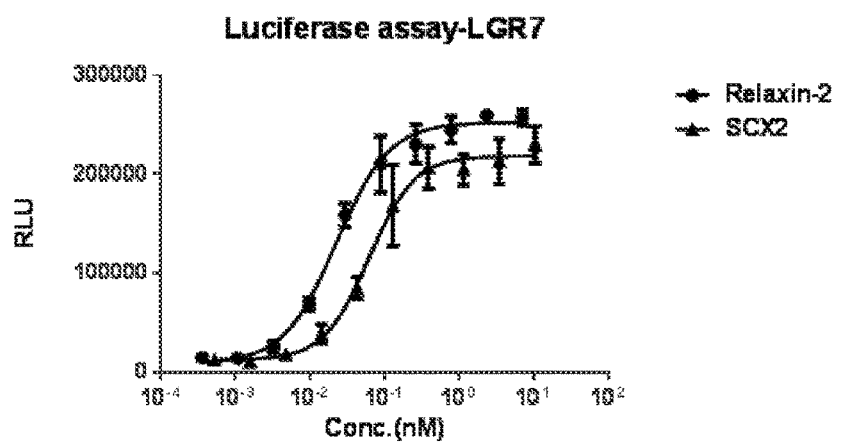
Figure 2C:
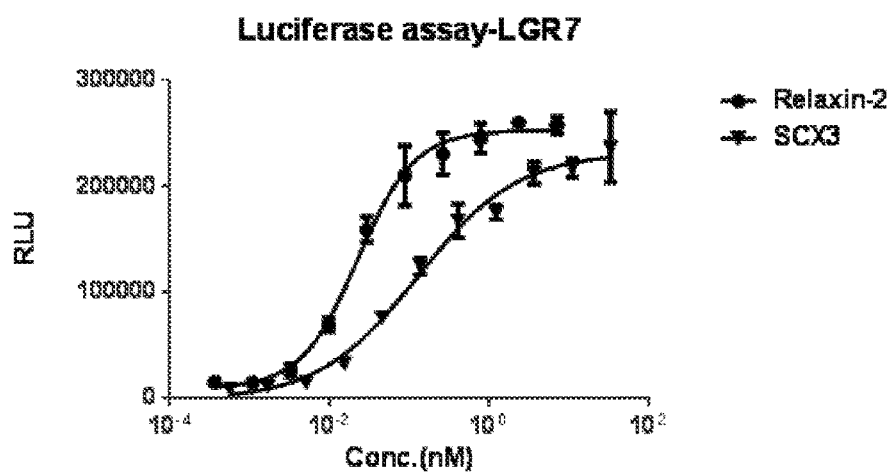

The $EC_{50}$ for SCX1 was 69.1 pM. The $EC_{50}$ for SCX2 was 61.2 pM. The $EC_{50}$ for SCX3 was 129 pM. The corresponding cures are shown in FIG. 2A (SCX1), FIG. 2B (SCX2), and FIG. 2C (SCX3).

Example 4: Binding of Palivizumab-Relaxin Fusion Proteins to RSV-Epitope

Figure 3A:
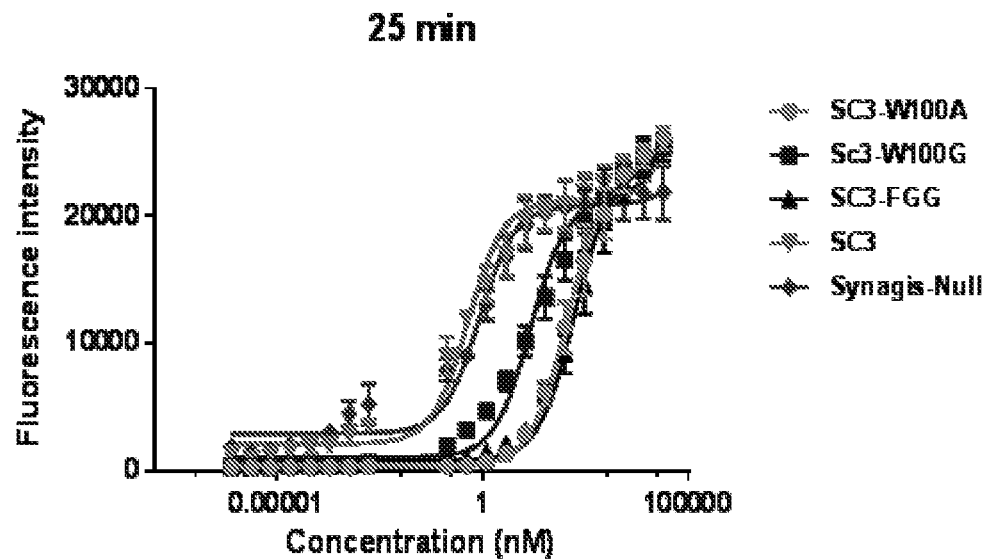
FIG. 3A and FIG. 3B depict graphs of palivizumab-relaxin fusion protein/RSV-epitope binding assay.
Figure 3B:
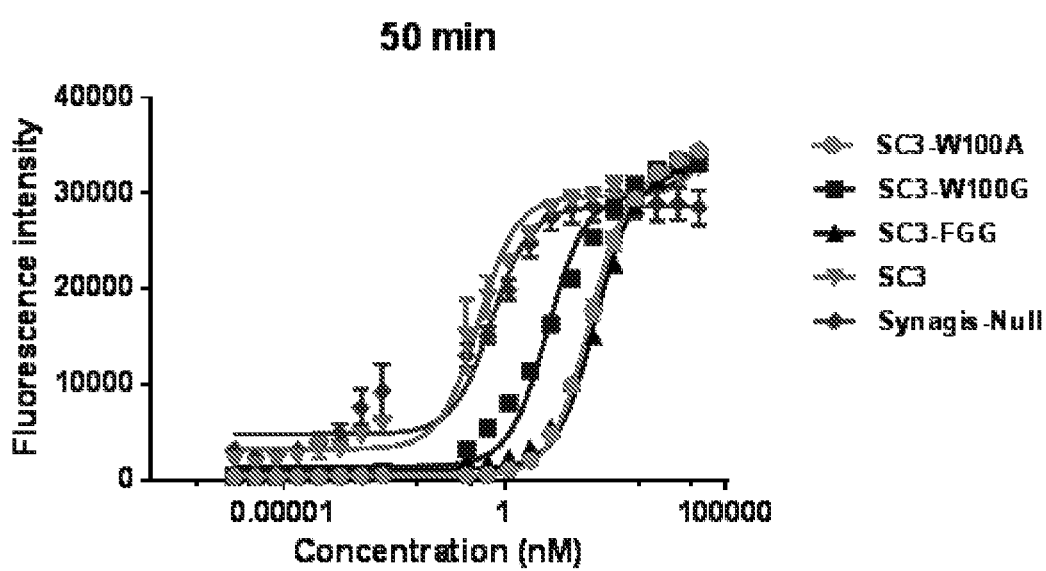

To test the reduction of palivizumab-relaxin fusion protein binding to RSV-epitope, an RSV binding assay was performed. Briefly, 0.1 ug of RSV F protein was coated in a 96 well plate. Palivizumab-relaxin fusion proteins as described in Example 2, SCX1, SCX2, and SCX3, and a null palivizumab antibody were added to separate wells. Anti-human IgG (Fc specific) at a 1:2,000 dilution in 2% BSA, PBS was added to each well. Fluorescence intensity was measured after 25 and 50 minutes. Plots of Fluorescence intensity vs. fusion protein concentration are shown in FIG. 3A (25 min) and FIG. 3B (50 min). Tables 11 and 12 show the corresponding data for each construct tested.

TABLE 11

Fusion protein binding assay to RSV-epitope (25 min)

| Protein name | Heavy chain | Light chain | Yield (mg/L) | LGR7 (nM) | LGR8 (nM) | Kd (nM) |
|---|---|---|---|---|---|---|
| SCX1 | Palivizumab(NH1, 16GS)-relaxin2(9GS) | Palivizumab L | 18.7 | 0.1285 | 939.2 | 111.9 |
| SCX2 | Palivizumab(NH2, 16GS)-relaxin2(9GS) | Palivizumab L | 18 | 0.1154 | 326.6 | 14.4 |
| SCX3 | Palivizumab(NH3, 16GS)-relaxin2(9GS) | Palivizumab L | 18 | 0.1146 | 16290 | 163.3 |
| SC3 | Palivizumab (null, 16GS)-relaxin2(9GS) | Palivizumab L | 25 | 0.205 | 177.1 | 0.425 |
| Palivizumab null | Palivizumab (null) | Palivizumab L | 11.6 | N/D | N/D | 0.80 |

TABLE 12

Fusion protein binding assay to RSV-epitope (50 min)

| Protein name | Heavy chain | Light chain | Yield (mg/L) | LGR7 (nM) | LGR8 (nM) | Kd (nM) |
|---|---|---|---|---|---|---|
| SCX1 | Palivizumab(NH1, 16GS)-relaxin2(9GS) | Palivizumab L | 18.7 | 0.1285 | 939.2 | 83.1 |
| SCX2 | Palivizumab(NH2, 16GS)-relaxin2(9GS) | Palivizumab L | 18 | 0.1154 | 326.6 | 9.034 |
| SCX3 | Palivizumab(NH3, 16GS)-relaxin2(9GS) | Palivizumab L | 18 | 0.1146 | 16290 | 107.1 |
| SC3 | Palivizumab (null, 16GS)-relaxin2(9GS) | Palivizumab L | 25 | 0.205 | 177.1 | 0.249 |
| Palivizumab null | Palivizumab (null) | Palivizumab L | 11.6 | N/D | N/D | 0.49 |

Example 5: Construction of Optimized Palivizumab-Relaxin Fusion Protein Antibodies Optimized palivizumab-relaxin fusion protein antibodies were created by pairing various heavy chain mutations with various light chain mutations. Heavy chain mutations included: NO (SEQ ID NO: 13), N99F, W100G, Y100$_a$G (SEQ ID NO: 22), and W100A (SEQ ID NO: 20). Light chain mutations included germline (SEQ ID NO: 10), S92N (SEQ ID NO: 11), and G91Y (SEQ ID NO: 12). Fc mutations included WT and E233P, L234V, L235A, ΔG236, A327G, A330S, and P331S. Construct components are summarized in Table 13 below.

TABLE 13

Optimized fusion protein summary

| Constructs | Heavy chain Mutations (CDR3H) | Light chain Mutations (CDR3L) | Fc |
|---|---|---|---|
| RLX300 (SC3.s) | NO | * | E233P, L234V, L235A, ΔG236, A327G, A330S, and P331S |
| RLX100 | NO | * | WT |
| RLX303 intact | N99F, W100G, Y100$_a$G* | S92N* | WT |
| RLX301 | N99F, W100G, Y100$_a$G* | * | E233P, L234V, L235A, ΔG236, A327G, A330S, and P331S |
| RLX302 | N99F, W100G, Y100$_a$G* | G91Y* | E233P, L234V, L235A, ΔG236, A327G, A330S, and P331S |
| RLX303 | N99F, W100G, Y100$_a$G* | S92N* | E233P, L234V, L235A, ΔG236, A327G, A330S, and P331S |
| RLX304 | W100A | * | E233P, L234V, L235A, ΔG236, A327G, A330S, and P331S |
| RLX305 | W100A | G91Y* | E233P, L234V, L235A, ΔG236, A327G, A330S, and P331S |
| RLX306 | W100A | S92N* | E233P, L234V, L235A, ΔG236, A327G, A330S, and P331S |
| SYN100 | NO | * | WT |
| SYN200 | NO | * | E233P, L234V, L235A, ΔG236, A327G, A330S, and P331S |
| SYN300 | N99F, W100G, Y100$_a$G* | S92N* | E233P, L234V, L235A, ΔG236, A327G, A330S, and P331S |

Figure 4:
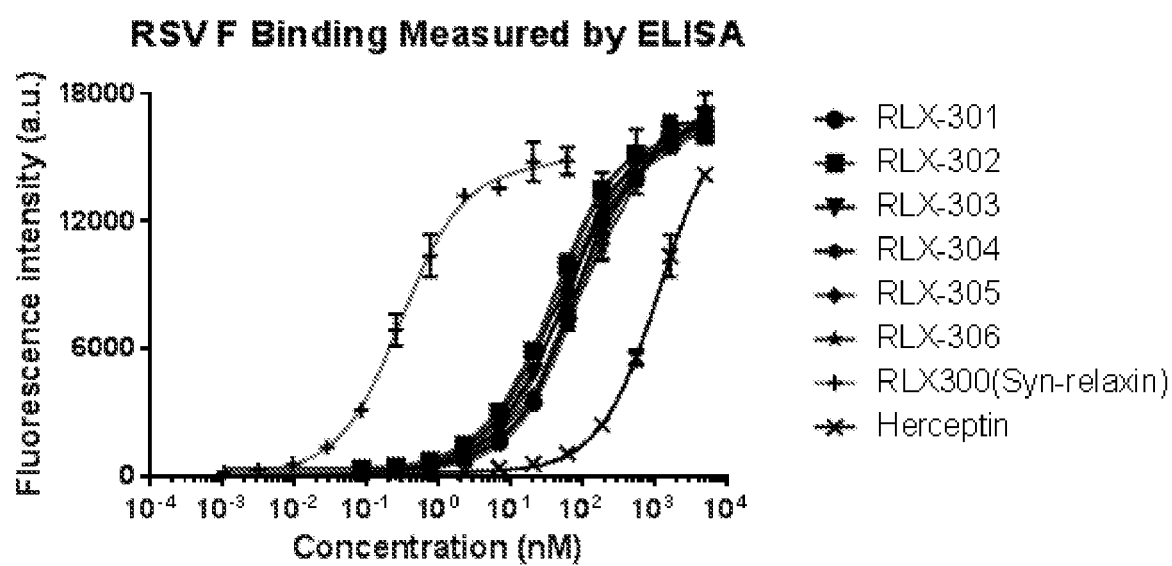
FIG. 4 shows binding of palivizumab-relaxin fusion proteins to RSV.
Figure 5A:
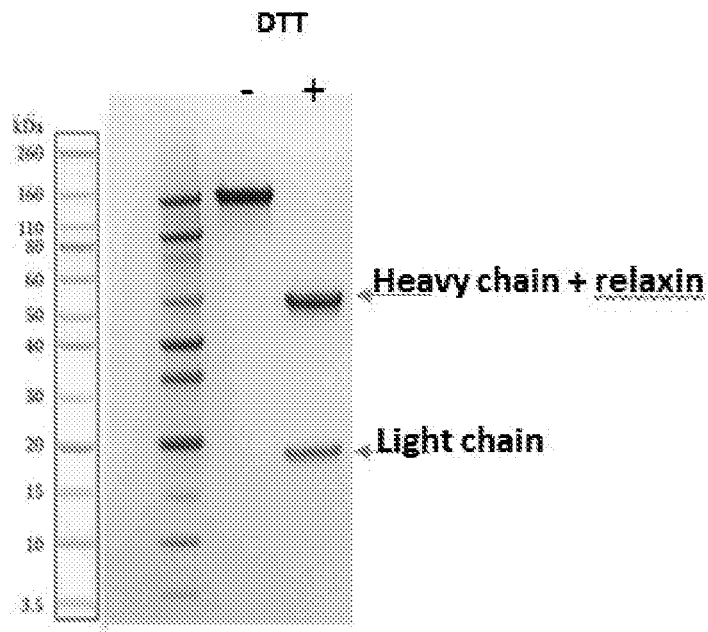
FIG. 5A, FIG. 5B, FIG. 5C, FIG. 5D, FIG. 5E, and FIG. 5F show SDS-PAGE gels of purified palivizumab-relaxin fusion proteins.
Figure 5B:
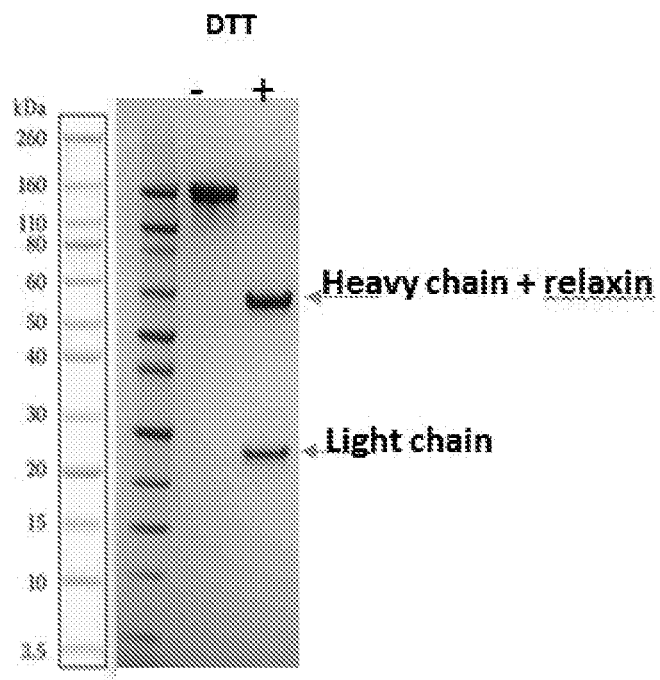
Figure 5C:
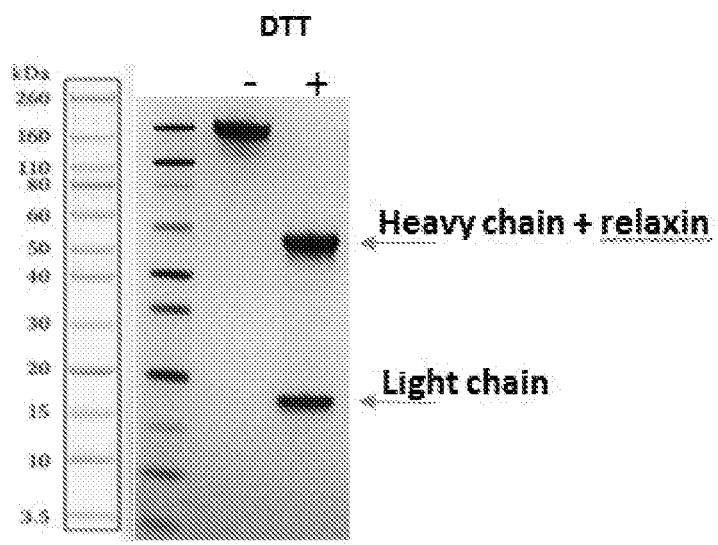
Figure 5D:
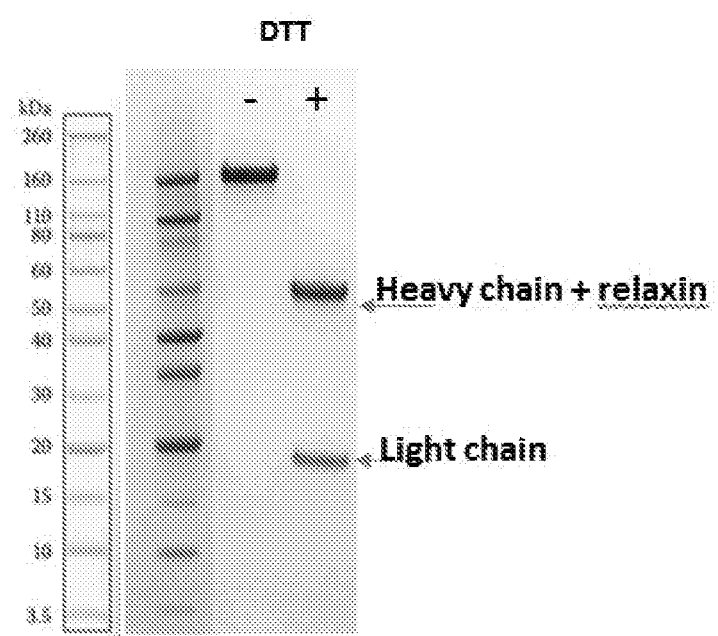
Figure 5E:
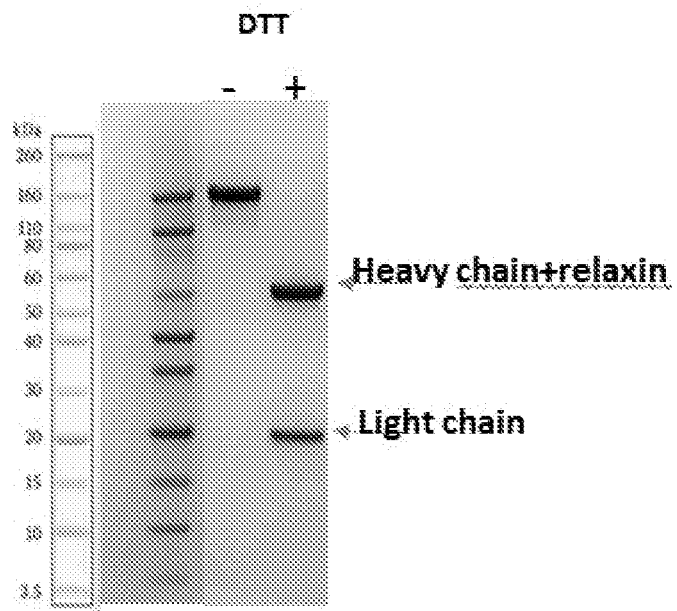
Figure 5F:
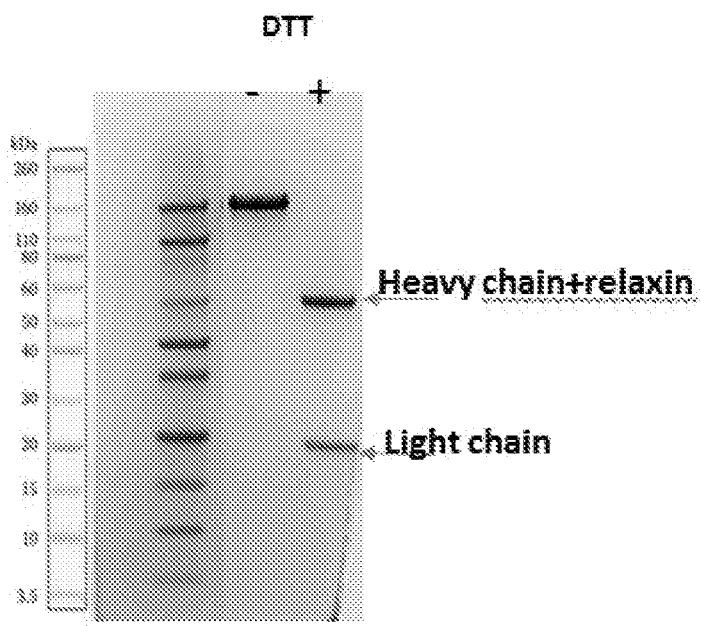
Figure 6A:
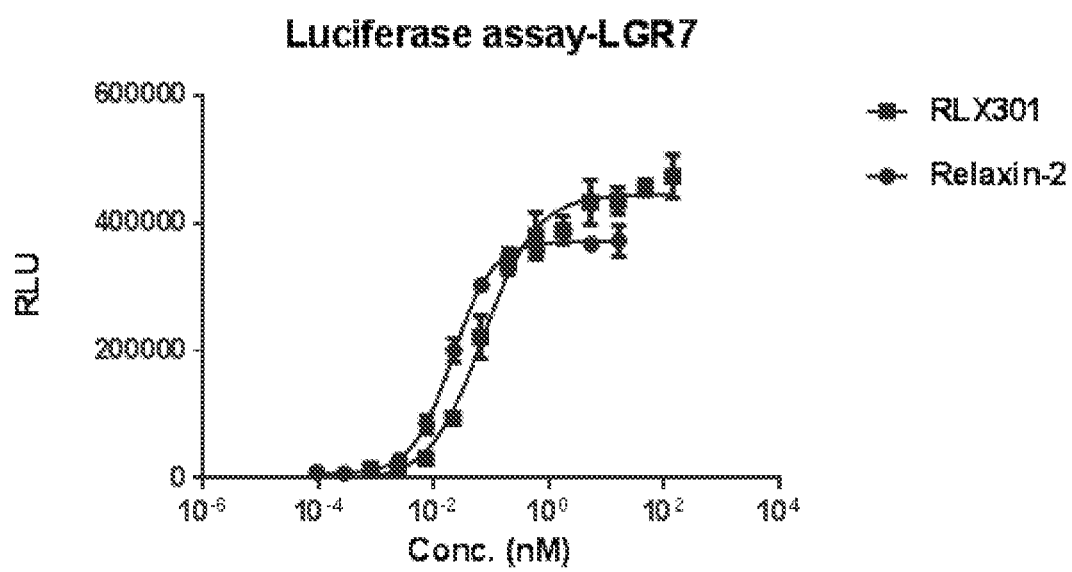
FIG. 6A, FIG. 6B, FIG. 6C, FIG. 6D, FIG. 6E, and FIG. 6F show graphs of the activities of palivizumab-relaxin fusion proteins.
Figure 6B:
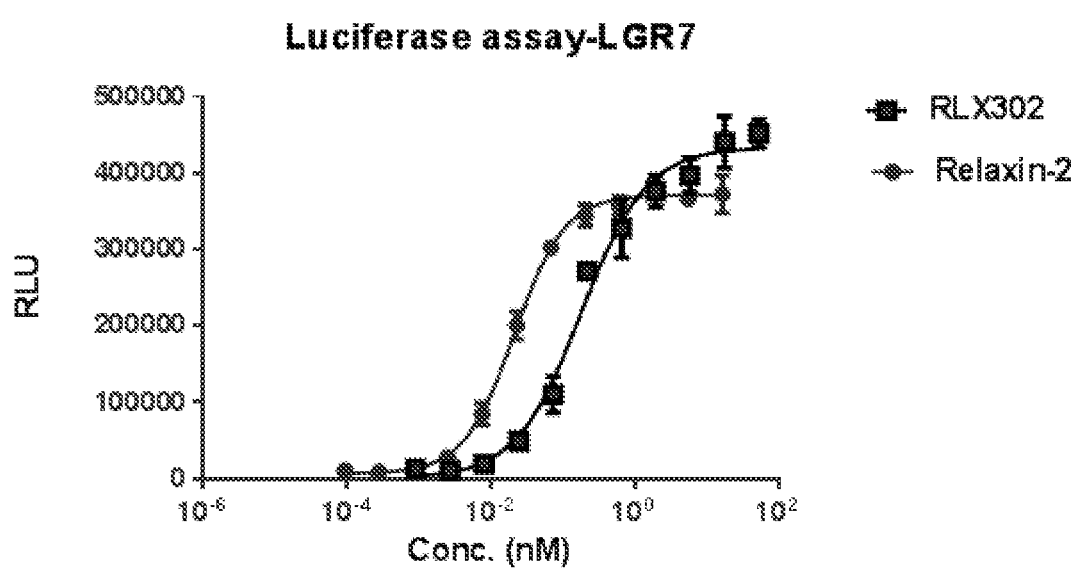
Figure 6C:
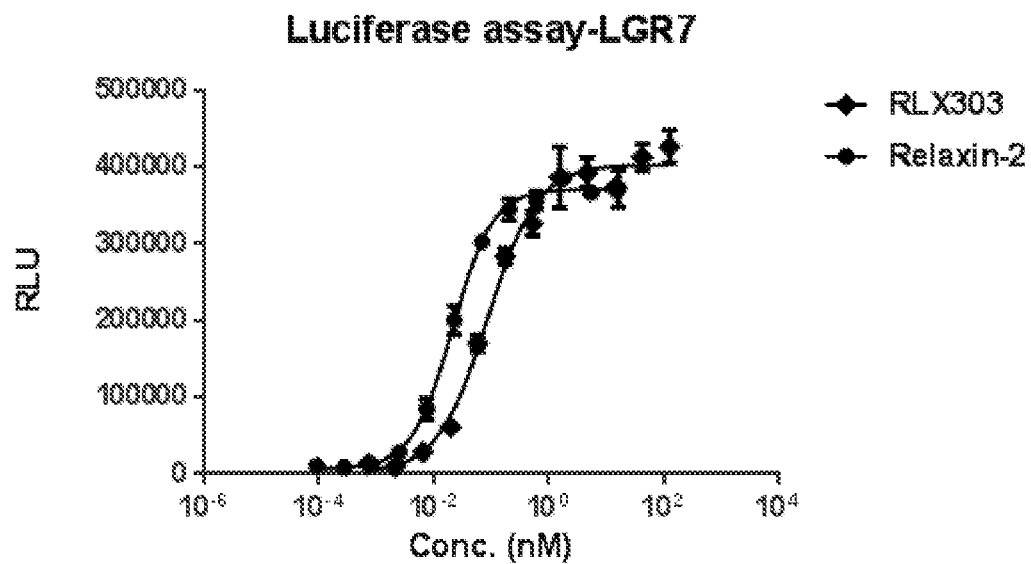
Figure 6D:
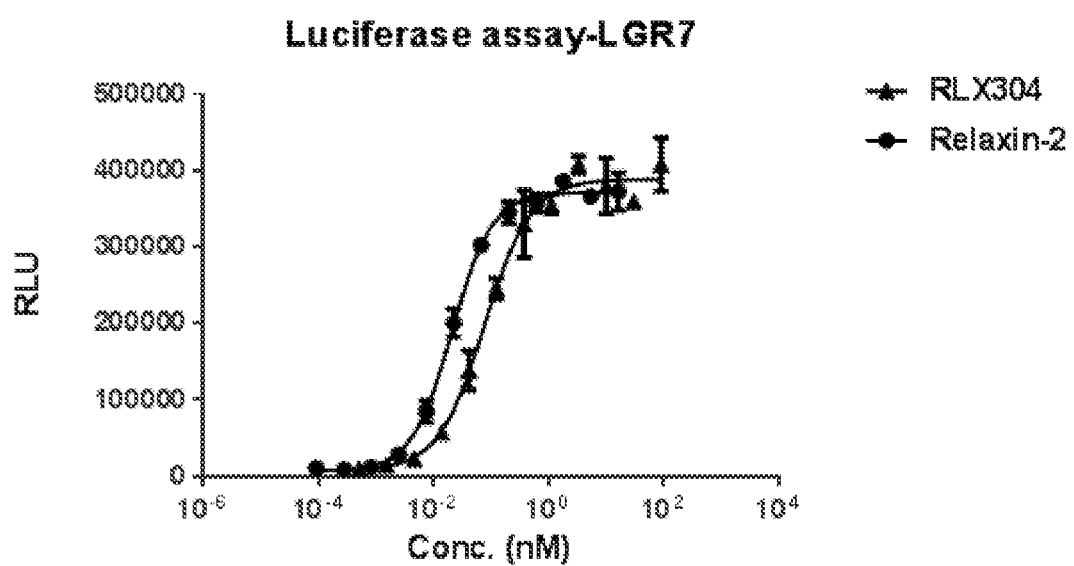
Figure 6E:
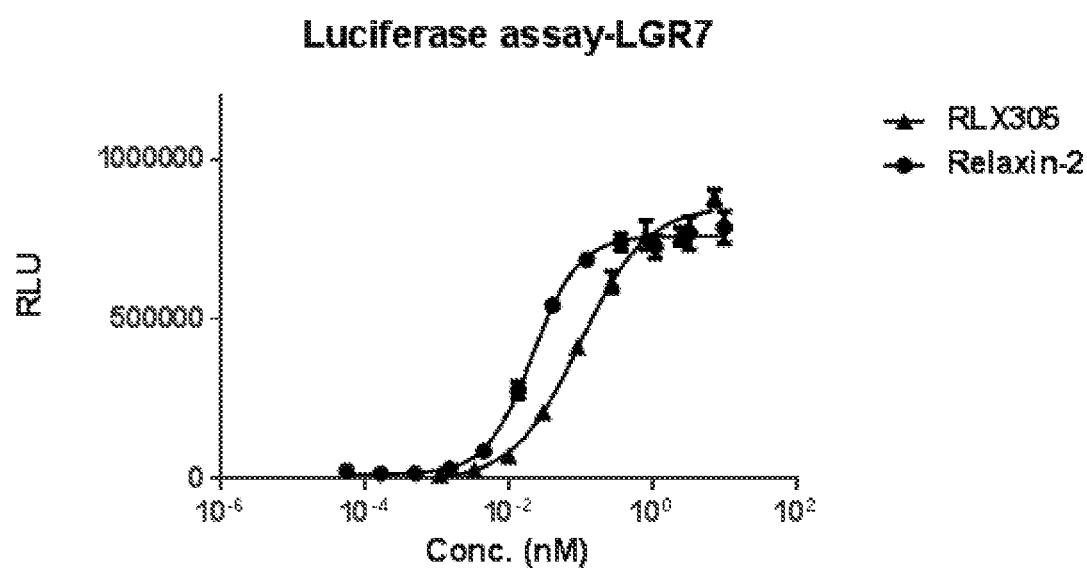
Figure 6F:
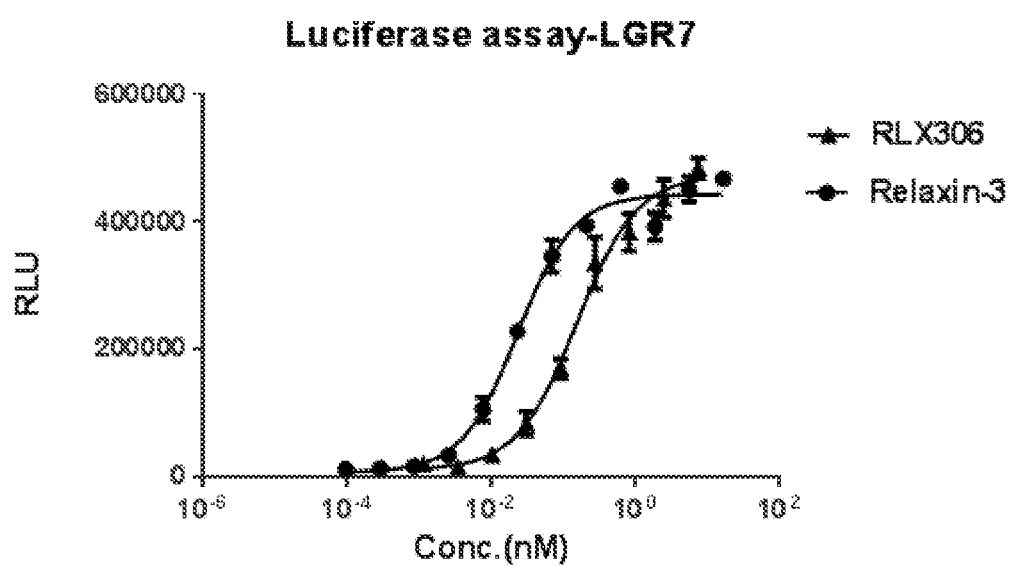
Figure 7A:
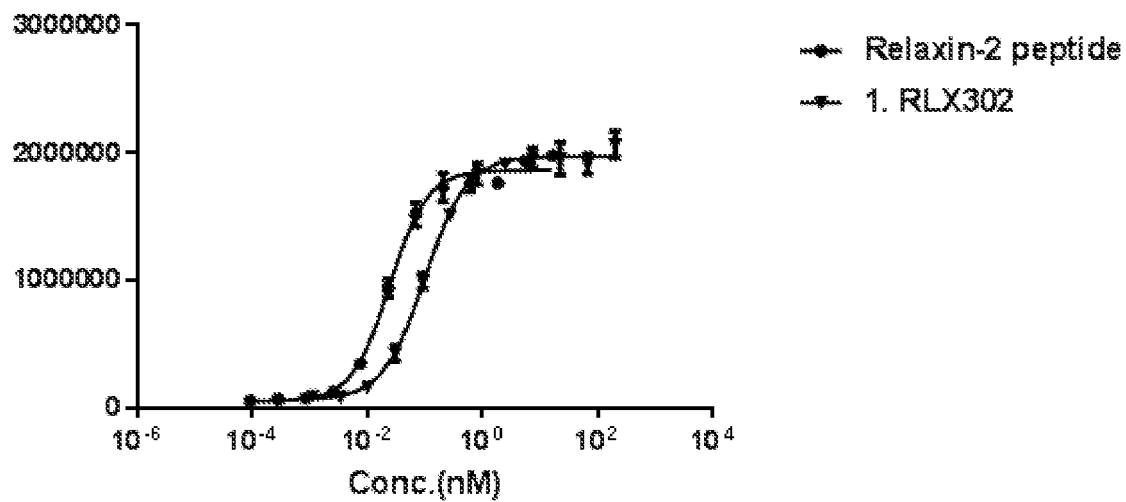
FIG. 7A and FIG. 7B show graphs of the activities of palivizumab-relaxin fusion proteins.
Figure 7B:
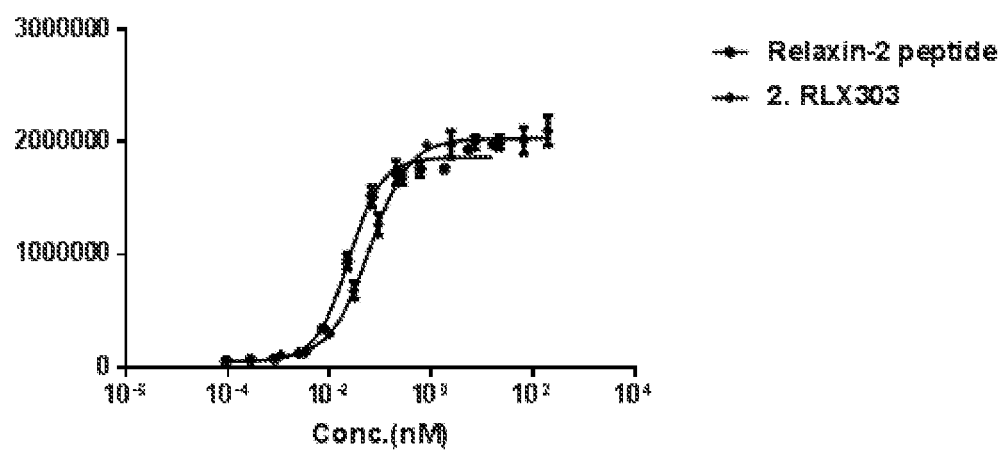
Figure 8A:
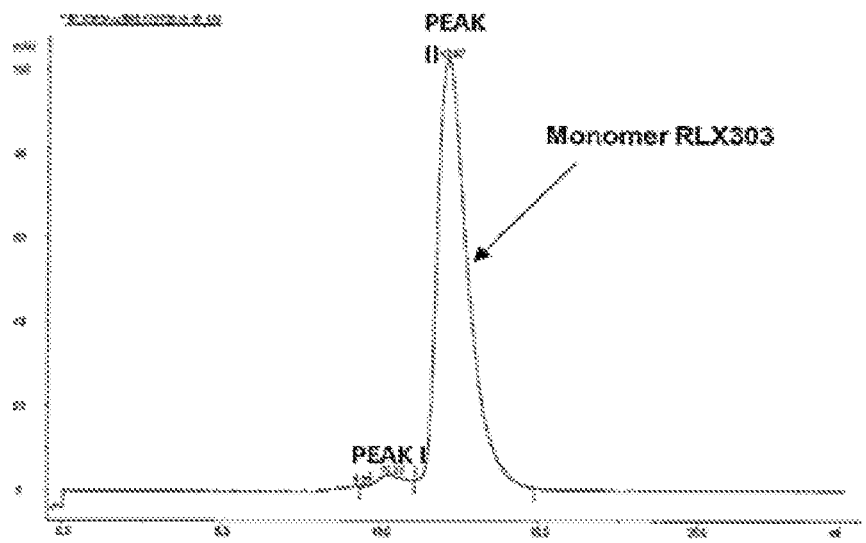
FIG. 8A and FIG. 8B show protein characterization of palivizumab-relaxin fusion protein RLX303.
Figure 8B:
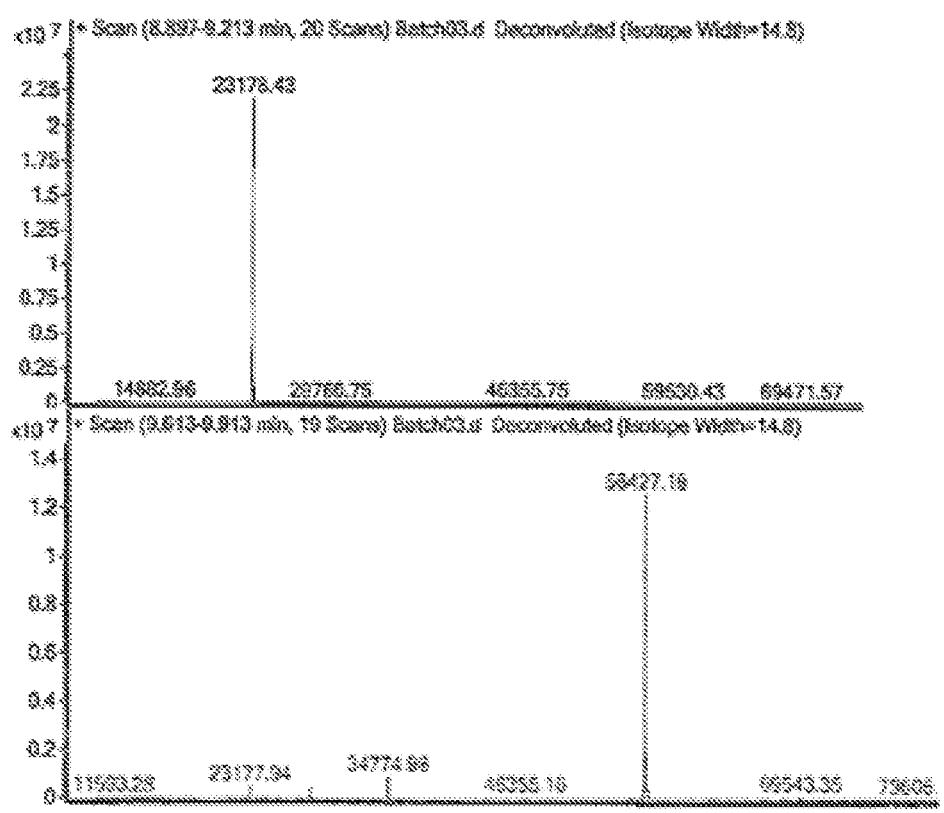

Example 5: Measurement of RSV Binding by Optimized Palivizumab-Relaxin Fusion Protein Antibodies Optimized palivizumab-relaxin fusion protein antibodies were tested for binding to RSV by ELISA assay. 100 ng/well RSV F protein was coated on 96-well plate in PBS 4° C. overnight. The plate was blocked with 2% BSA/PBS at room temperature for 1 hr, then washed twice with 200 μL PBS. The fusion antibodies were incubated at various concentrations (as indicated in FIG. 4) in 2% BSA/PBS at room temperature for 1 hr. Plates were washed with PBS (0.025% Tween-20 in PBS) four times and washed with PBS one time. Then plates were incubated with horseradish peroxidase-conjugated anti-human IgG (Fc specific) in PBS at room temperature for 1 hr, washed with PBS (0.025% Tween-20 in PBS) five times, developed with QuantaBlu fluorogenic peroxidase substrate (Thermo Fisher Scientific, IL). Binding was quantified using Spectramax fluorescence plate reader with excitation at 325 nm and emission at 420 nm. Binding curves are shown in FIG. 5. Binding Kd values were determined (Table 14).

TABLE 14

Fusion protein binding assay (10 min)

| Protein | Kd (nM) |
|---|---|
| RLX300 (no mutations) | .301 |
| RLX301 | 79.3 |
| RLX302 | 37.7 |
| RLX303 | 52.1 |
| RLX304 | 38.2 |
| RLX305 | 75.2 |
| RLX306 | 82.7 |
| Herceptin | 1351 |

Example 6: Measurement of Thermal Stability of Optimized Palivizumab-Relaxin Fusion Protein Antibodies Thermal stability of optimized palivizumab-relaxin fusion protein antibodies was determined. Results of this assay are shown in Table 15 below. The thermal stabilities were measured using a fluorescent protein binding dye (Protein Thermal Shift assay, Life Technologies Co., CA). Briefly, Samples with a working volume of 20 μL per well were prepared by mixing 5 ul protein Thermal shift buffer, 2.5 μL of 8× protein thermal shift Dye with 12.5 μL of antibody (0.5 mg/mL) in DPBS buffer, loaded onto a 96-well 0.2 thin-wall PCR plate, and sealed with S MicroAmp® Optical Adhesive Film. Then a melt curve was run on a real-time PCR instrument. Data were collected at 1° C. intervals from 25° C. through 99° C. on the StepOnePlus™ Real-Time PCR System and analyzed using the Protein Thermal Shift™ Software.

TABLE 15

| Fusion protein thermal stability | | |
|---|---|---|
| Protein | $1^{st}$ Tm (° C.) | $2^{nd}$ Tm (° C.) |
| RLX301 | 67.83 ± 0.19 | 85.4 ± 0.76 |
| RLX302 | 67.95 ± 0.0 | 83.25 ± 0.38 |
| RLX303 | 67.82 ± 0.19 | 83.66 ± 0.19 |
| RLX304 | 67.82 ± 0.19 | 85.53 ± 0.57 |
| RLX305 | 68.09 ± 0.19 | 83.39 ± 0.19 |
| RLX306 | 68.09 ± 0.19 | 85.52 ± 0.0 |

Example 7: Expression and Purification of Optimized Palivizumab-Relaxin Fusion Proteins Palivizumab-relaxin heavy chain fusion proteins were each expressed through co-transfection of freestyle HEK293 cells with palivizumab-relaxin heavy chain mammalian expression vectors described in Example 5. The cells were grown in shaker flasks at 125 rpm with freestyle 293 expression medium (Life Technologies) at 37° C. with 5% CO2. Expressed proteins were secreted into the culture medium and harvested twice every 48 hours after transfection. The fusion proteins were purified by Protein A/G chromatography (Thermo Fisher Scientific, IL) and analyzed by SDS-PAGE gel. Purified heavy chain fusion proteins expressed with palivizumab light chain are shown in the SDS-PAGE gels of FIGS. 5A-F. For each gel, the first lane corresponds to a molecular marker, the second lane corresponds to purified protein, and the third lane corresponds to purified protein treated with the reducing agent DTT. FIG. 5A shows purified RLX301 (SEQ ID NO: 22) and (SEQ ID NO: 10). FIG. 5B shows purified RLX302 (SEQ ID NO: 22) and (SEQ ID NO: 12). FIG. 5C shows purified RLX303 (SEQ ID NO: 22) and (SEQ ID NO: 11). FIG. 5D shows purified RLX304 (SEQ ID NO: 20) and (SEQ ID NO: 10). FIG. 5E shows purified RLX305 (SEQ ID NO: 20) and (SEQ ID NO: 12). FIG. 5F shows purified RLX306 (SEQ ID NO: 20) and (SEQ ID NO: 11).

Example 8: Activity of Optimized Palivizumab-Relaxin Fusion Proteins to Activate Relaxin Receptors The activities of optimized palivizumab-relaxin fusion proteins purified in Example 7 were examined by a luciferase assay. HEK293 cells overexpressed with relaxin receptor (LGR7) and cAMP responsive element (CRE)-luciferase (Luc) reporter gene were grown in DMEM supplemented with 10% FBS at 37° C. with 5% CO2. Cells were seeded in 384-well plates for 24 hours and subsequently independently treated with various concentrations of palivizumab-relaxin fusion proteins purified from Example 7 (RLX301, RLX302, RLX303, RLX304, RLX305, or RLX306) or relaxin2 peptide for an additional 24 hours. Luminescence intensities were then measured using One-Glo (Promega) luciferase reagent by following manufacturer's instruction.

The $EC_{50}$ values were determined by fitting data into a logistic sigmoidal function: y=A2+(A1-A2)/(1+(x/x0)p), where A1 is the initial value, A2 is the final value, x0 is the inflection point of the curve, and p is the power. The $EC_{50}$ for relaxin-2 was 22 pM. The $EC_{50}$ for RLX301 was 72 pM. The $EC_{50}$ for RLX302 was 179 pM. The $EC_{50}$ for RLX303 was 86 pM. The $EC_{50}$ for RLX304 was 78 pM. The $EC_{50}$ for RLX305 was 98 pM. The $EC_{50}$ for RLX306 was 153 pM. The corresponding cures are shown in FIG. 6A (RLX301), FIG. 6B (RLX302), FIG. 6C (RLX303), FIG. 6D (RLX304), FIG. 6E (RLX305), and FIG. 6F (RLX306).

Activities of optimized palivizumab-relaxin fusion proteins, RLX 302 and RLX303, were further examined using UL-hLGR7-Cre-Luc reporter cell line. The $EC_{50}$ for relaxin-2 was 20 pM and SA was 1000 units/μg. The $EC_{50}$ for RLX302 was 130 pM and SA was 5.9 units/μg. The $EC_{50}$ for RLX303 was 93 pM and SA was 8.0 units/μg. The corresponding curves are shown in FIG. 7A (RLX302) and FIG. 7B (RLX303).

Example 9: RLX303 Protein Characterization

RLX303 was characterized by analytical size-excusion chromatography and liquid chromatography-mass spectroscopy. RLX303 was confirmed to contain 96% of RLX303 monomer protein with correct light chain and heavy chain masses. Protein concentration was found to be 26-29 mg/ml in PBS (pH 7.4). Analytical size-exchange chromatography is shown in FIG. 8A. Liquid chromatography-mass spectroscopy is shown in FIG. 8B.

Example 10: Relaxin-Ig Fusion Serum Stability

Figure 9A:
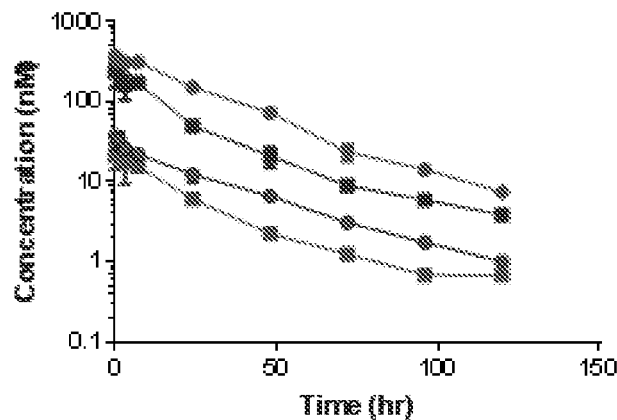
FIG. 9A, FIG. 9B, and FIG. 9C show serum stability of relaxin-2 peptide and palivizumab-relaxin fusion proteins RLX302 and RLX303.
Figure 9B:
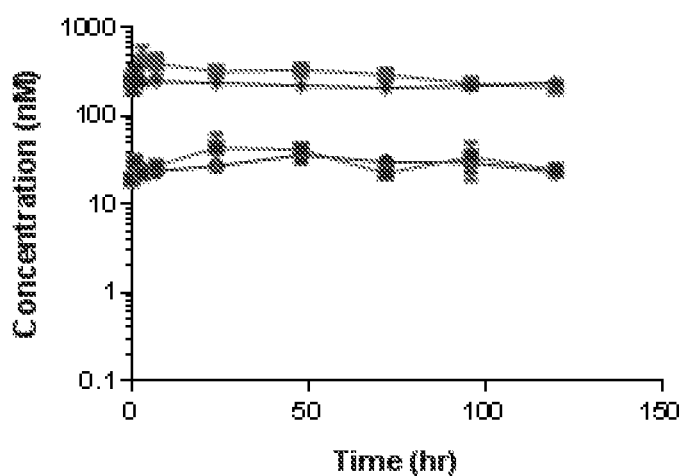
Figure 9C:
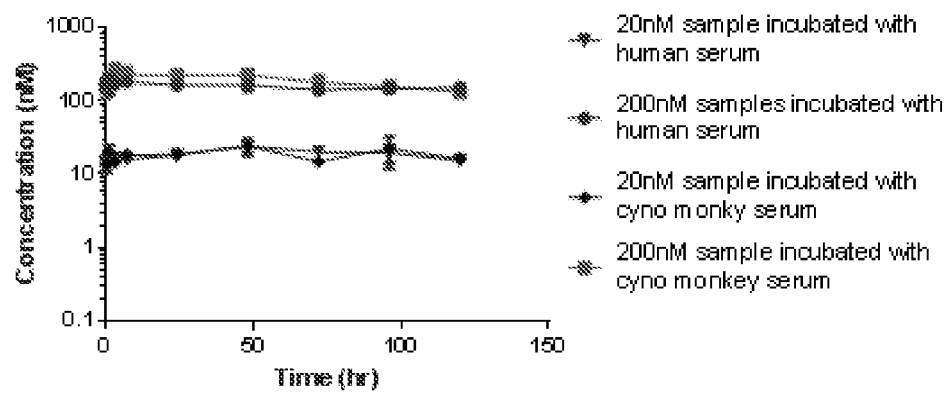

Serum stability of Relaxin-2 peptide, RLX302, and RLX303 was determined. Proteins were incubated with serum, then activity was measured in cell-based assays. Relaxin-Ig fusions remained stable over 5 days in human serum with about 15% loss of activity in cyno serum. Over 95% of human relaxin-2 peptide is gone after 5 days with degradation more rapid in cyno serum than in human serum. Sample concentrations were determined by ELISA and LC/MS was used to evaluate the chemical stability of the Relaxin-Ig fusions in serum. Stability curves are shown in FIG. 9A (Relaxin-2 peptide), FIG. 9B (RLX302), and FIG. 9C (RLX303).

Example 11: Relaxin Ig-Fusion PK Analysis

Figure 10:
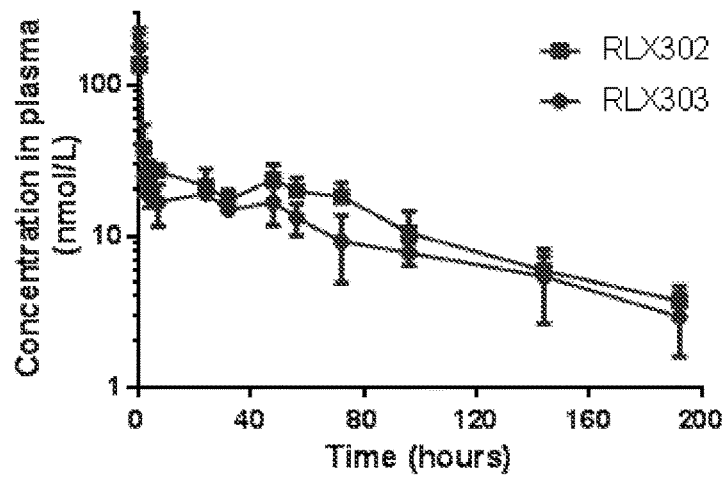
FIG. 10 shows mouse pharmacokinetic analysis of palivizumab-relaxin fusion proteins.

Pharmacokinetic properties of RLX302 and RLX303 were evaluated in mice using a single IV injection in CD1 mice at a dose of 3.7 mg/kg (n=3). Comparable exposure and half-life was found between the RLX302 and RLX303 fusion proteins. Pharmacokinetic data for the mouse experiments is found in Table 16. Pharmacokinetic curves for the mouse experiments are shown in FIG. 10.

TABLE 16

Mouse PK Analysis

| Protein | $T_{1/2}$ (hr) | $T_{max}$ (hr) | $C_{max}$ (nmol/L) | AUC (nmol · hr/L) |
|---|---|---|---|---|
| RLX302 | 63.78 | 0.5 | 137.06 | 3023.74 |
| RLX303 | 68.18 | 0.5 | 178.29 | 2372.33 |

Figure 11A:
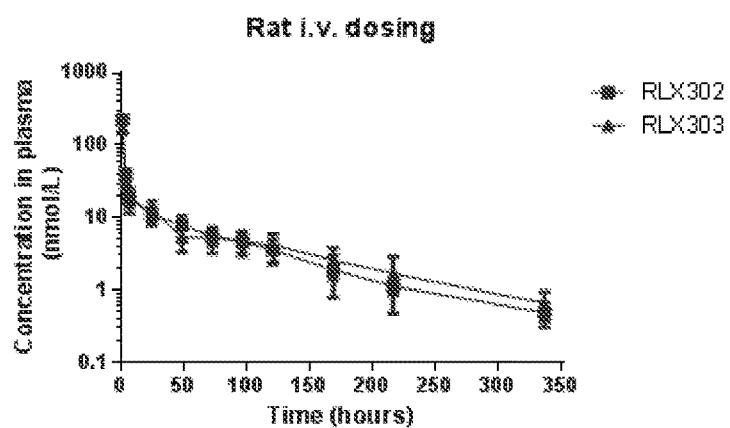
FIG. 11A and FIG. 11B show rat pharmacokinetic analysis of palivizumab-relaxin fusion proteins.
Figure 11B:
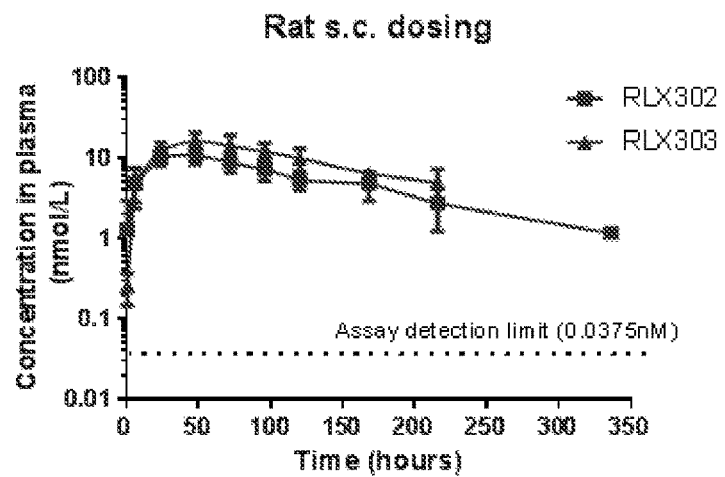

Pharmacokinetic properties of RLX302 and RLX303 were evaluated through a single i.v. or s.c injection in SD1 rats at a dosage of 2.1 mg/kg (n=3). Comparable exposure and half-life was found between the RLX302 and RLX303 fusion proteins. For s.c. dosing, in the RLX302 dosed animals, samples from 2 out 3 rats at timepoint 336 hr were out of detection range. In the RLX303 s.c. dosed animals, all animals were below assay detection at timepoint 336 hr Pharmacokinetic data for the rat experiments is found in Table 17. Pharmacokinetic curves for the rat experiments are shown in FIG. 11A and FIG. 11B.

TABLE 17

Rat PK Analysis

| Dosing Route | Protein | $T_{1/2}$ (hr) | $T_{max}$ (hr) | $C_{max}$ (nmol/L) | AUC (nmol · hr/L) |
|---|---|---|---|---|---|
| IV. | RLX302 | 68 | 0.33 | 226 | 1756 |
|  | RLX303 | 85 | 0.33 | 176 | 1750 |
| S.C. | RLX302 | 91 | 48 | 11 | 1780 |
|  | RLX303 | 91 | 48 | 17 | 2795 |

Example 12: Mouse Pharmacodynamics Analysis

Figure 12A:
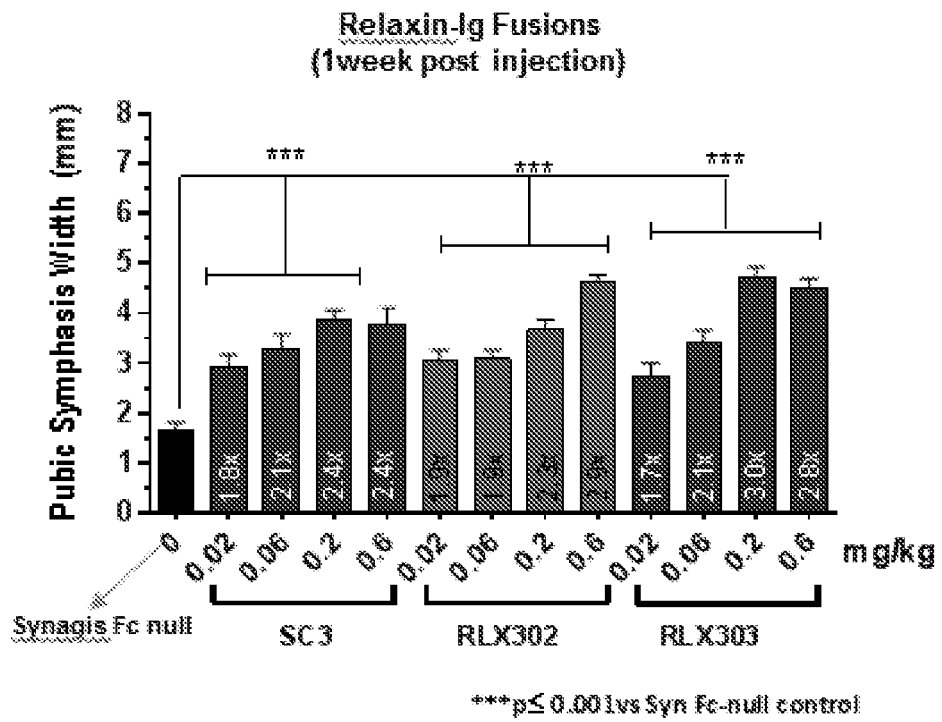
FIG. 12A and FIG. 12B show pharmacodynamics analysis of palivizumab-relaxin fusion proteins.
Figure 12B:
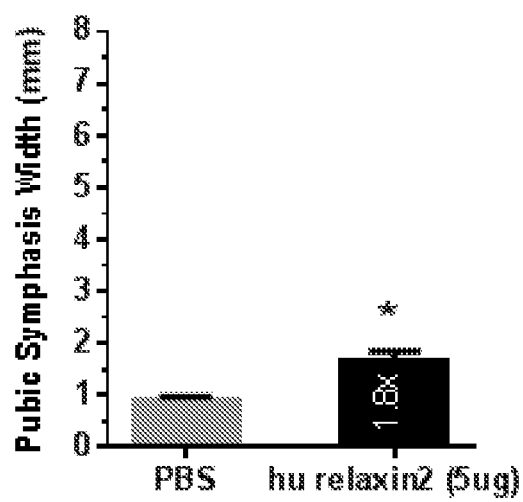

Pharmacodynamic properties of RLX302 and RLX303 were evaluated using a s.c. dose between 0.02 to 0.6 mg/kg in estrogen-primed CD1 female mice (n=8-12). Mice were treated with human relaxin-2 peptide as a control Interpubic ligament width was measured at 1 week post dosing. Pharmacodynamic data is shown in FIG. 12A. Mice were treated with human relaxin-2 peptide as a control and pubic symphasis width was measured 24 hours post injection. Control data is shown in FIG. 12B.

Example 13: Phase 1 Clinical Trials

Cohorts of 10 volunteers, 8 'active' and 2 placebo, are recruited for single ascending dose safety evaluation and PD measures of RLX302 and RLX303 in healthy volunteers. Five dose-levels are used having a starting dose ~0.1 mg/kg IV, half-log escalating dose groups (0.1, 0.3, 1.0, 3.0, 10 mg/kg). Intravenous doses are used initially to support future acute/subacute indications where rapid onset of action is preferred (based on differences seen preclinically); also allows discontinuation of infusion if acute adverse events occur. 2-3 dose-levels are used (high, mid, +/−low) with subcutaneous (SC) dosing to establish SC safety, local tolerability, PK, and bioavailability. Additional subjects (optional) are specified in the protocol to add up to 2 lower or intermediate dose groups depending on safety/tolerability/PD effects. Patients are followed for 3 months for PK, safety.

For multiple ascending dose safety evaluation, 5 dose groups are used: 1, 3, 10 mg/kg SC Q2w and 1.5 mg/kg Q1w dosing. Q2w group receives 7 SC injections over 12 weeks; Q1w group receives 13 injections over 12 weeks. Cohorts of ten healthy volunteers, 8 'active' and 2 placebo, safety evaluation and PD measures in healthy volunteers. The goal is to establish safety/tolerability/PK and PD across dose range in healthy volunteers. Potential for immunogenicity (ADAs) is evaluated using pooled data. Additional subjects (optional 2 cohorts) specified in the protocol to explore lower, intermediate, and alternate frequency (Q month, additional Q1w groups) Total follow up for 5 months (from initial dose) for PK, safety.

Example 14: Phase 1b Clinical Trials

Long-acting relaxin-immunoglobulin fusion, RLX302 is studied in a Phase 1b clinical trial for reducing heart failure hospitalization, cardiovascular death, and dyspnea. The primary objective is, using parallel groups, randomized, Pbo-controlled safety, tolerability, PK and PD study in subjects with compensated stable HFrEF to support the safety assessment and dose range selection for a chronic dosing Phase 2 Program in chronic heart failure by: 1) Characterizing the safety and tolerability of subcutaneous RLX302 in patients with stable compensated HFrEF and 2) Characterize the PK of subcutaneous RLX302 in patients with HFrEF. The secondary objective is: 1) characterize the cardiac PD effects of RLX302 using blood and imaging markers in a population of HFrEF patients with baseline elevated NT-proBNP (>600 pg/ml—TBD) and 2) Characterize the renal PD effects of RLX302 in a population of HFrEF patients with baseline elevated NT-proBNP (>600 pg/ml—TBD). Tertiary objectives include characterizing the effects of RLX302 on markers of cardiac damage and clinical outcomes related to RLX302 effect on cardiac and renal physiology. Primary endpoints are: 1) Safety measurements including standard clinical and laboratory evaluations (BP, din labs, ECG, etc.), 2) PK, and 3) immunogenicity assessments (ADAs, AEs). Secondary endpoints include: 1) Cardiac biomarkers: NT-proBNP, 2) Cardiac Imaging (transthoracic echocardiography): Left Atrial size, EF, strain, diastolic function, remodeling indices, and 3) Renal physiology/injury markers: renal blood flow, GFR, cystatin C, KIM1, plasma BUN & creatinine. Tertiary endpoints include: 1) MACE events, HF hospitalization, CV death, all cause mortality; 2) composite clinical assessment (NYHA classification, Pt Global Assessment, MACE); 3) Hospitalization for renal failure; and 4) Adjustments in diuretics and other HF medications (evidence of intensification of therapy or potential diuretic sparing effect) from baseline. The strategic goals are: 1) Early capture of potential mechanism-based biologic and clinical benefits to enable accelerated investment in further development activities (chronic tox, Ph 2 startup, etc.) and 2) Trigger transition points in collaboration. Study rationale is to assess the safety, tolerability, and early signs of efficacy for RLX302 in the major eventual target population of HFrEF patients. Strong biologic and/or clinical signals of treatment benefit would enhance confidence for further investment and potential timeline acceleration. Key biomarker objectives include ≥30% reduction in NT-proBNP during first week of treatment. Key inclusion criteria are: HFrEF, NYHA class Recent HF hospitalization within 3-6 months, other enrichment criteria for high risk HF e.g. NT-proBNP≥600-900 pg/mL, and eGFR (limit to be determined based on projected impact on enrollment). Key exclusion criteria are HFpEF, CrCl<30 (advanced renal dysfunction), and BP restrictions similar to Pre-RELAX AHF/RELAX AHF/PARADIGM (e.g. SBP<100). Key features of the trial are: 1) randomized, double blind, multiple dose; 2) HFrEF patients, 3) four week exposure (2 SC doses), 4 weeks timepoint from baseline=primary endpoint; assessments continued at weeks 8 and 12 (study completion); 4) 2-3 dose levels+placebo (approx. 120 subjects total); and 5) interim analysis based on 1 or 2 wk follow up data and 75% recruitment—potential to trigger investment in chronic tox and/or manufacturing of drug product. Treatment arms will include PBO, dose levels MTD, mid- and low-dose guided by SAD in HV. Sample sizes will be 30-40 subjects per arm as guided by available data.

Clinically meaningful, dose dependent changes in multiple aspects of potential therapeutic benefit are observed (as outlined in the key biomarker objectives and below). Signals are concordant and of sufficient magnitude to reasonably preclude a chance finding. Therapeutic benefits include: reduction in NT-proBNP, reduction in hs-TnI/T, improvement in Echo parameters, e.g., reduction in LA size (in patients with increased LA size at baseline), reduction of clinical signs of congestion (clinical signs/diuretic use, LFTs), decreased serum creatinine and BUN, improved renal hemodynamics (improved RPF with stable or improved GFR±reduced Filtration Fraction), improvement of dyspnea (symptom scores; includes DOE, PND), worsening HF over 4-12 weeks (during active treatment phase and/or follow-up period), hospital admission for AHF or Renal Failure over 4 weeks (during active treatment phase and/or follow-up period). Treatment with RLX302 results in improved outcomes with more convenient dosing schedules than current relaxin-based treatments (e.g. serelaxin).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references cited herein are incorporated by reference in their entirety and for all purposes to the same extent as if each individual publication or patent or patent application was specifically and individually indicated to be incorporated by reference in its entirety for all purposes.

TABLE 1

Immunoglobulin Light Chain (LC) and Heavy Chain (HC)-Nucleotide Sequence

| NAME | SEQ ID NO | SEQUENCE |
|---|---|---|
| Palivizumab L | 1 | GACATCCAGATGACCCAGTCCCCCTCCACCCTGTCCGCCTCCGTGG<br>GCGACCGCGTGACCATCACCTGCAAGTGCCAGCTGTCCGTGGGCT<br>ACATGCACTGGTACCAGCAGAAGCCCGGCAAGGCCCCCAAGCTGC<br>TGATCTACGACACCTCCAAGCTGGCCTCCGGCGTGCCCTCCCGCTT<br>CTCCGGCTCCGGCTCCGGCACCGAGTTCACCCTGACCATCTCCTCC<br>CTGCAGCCCGACGACTTCGCCACCTACTACTGCTTCCAGGGCTCCG<br>GCTACCCCTTCACCTTCGGCGGCGGCACCAAGCTGGAGATCAAAC<br>GAACTGTGGCTGCACCATCTGTCTTCATCTTCCCGCCATCTGATGA<br>GCAGTTGAAATCTGGAACTGCCTCTGTCGTGTGCCTGCTGAATAAC<br>TTCTATCCCAGAGAGGCCAAAGTACAGTGGAAGGTGGATAACGCC<br>CTCCAATCGGGTAACTCCCAGGAGAGTGTCACAGAGCAGGACAGC<br>AAGGACAGCACCTACAGCCTCAGCAGCACCCTGACGCTGAGCAAA<br>GCAGACTACGAGAAACACAAAGTCTACGCCTGCGAAGTCACCCAT<br>CAGGGCCTGTCCTCGCCCGTCACAAAGAGCTTCAACAGGGGAGAG<br>TGT |
| Palivizumab L (germline) | 2 | GACATCCAGATGACCCAGTCCCCCTCCACCCTGTCCGCCTCCGTGG<br>GCGACCGCGTGACCATCACCTGCAAGTGCCAGCTGTCCGTGGGCT |

TABLE 1-continued

Immunoglobulin Light Chain (LC) and Heavy Chain (HC)-Nucleotide Sequence

| NAME | SEQ ID NO | SEQUENCE |
|---|---|---|
| | | ACATGCACTGGTACCAGCAGAAGCCCGGCAAGGCCCCCAAGCTGC<br>TGATCTACGACACCTCCAAGCTGGCCTCCGGCGTGCCCTCCCGCTT<br>CTCCGGCTCCGGCTCCGGCACCGCCTTCACCCTGACCATCTCCTCC<br>CTGCAGCCCGACGACTTCGCCACCTACTACTGCTTCCAGGGCTCCG<br>GCTACCCCTTCACCTTCGGCGGCGGCACCAAGCTGGAGATCAAAC<br>GAACTGTGGCTGCACCATCTGTCTTCATCTTCCCGCCATCTGATGA<br>GCAGTTGAAATCTGGAACTGCCTCTGTCGTGTGCCTGCTGAATAAC<br>TTCTATCCCAGAGAGGCCAAAGTACAGTGGAAGGTGGATAACGCC<br>CTCCAATCGGGTAACTCCCAGGAGAGTGTCACAGAGCAGGACAGC<br>AAGGACAGCACCTACAGCCTCAGCAGCACCCTGACGCTGAGCAAA<br>GCAGACTACGAGAAACACAAAGTCTACGCCTGCGAAGTCACCCAT<br>CAGGGCCTGTCCTCGCCCGTCACAAAGAGCTTCAACAGGGGAGAG<br>TGT |
| Palivizumab L (G91Y) | 3 | GACATCCAGATGACCCAGTCCCCCTCCACCCTGTCCGCCTCCGTGG<br>GCGACCGCGTGACCATCACCTGCAAGTGCCAGCTGTCCGTGGGCT<br>ACATGCACTGGTACCAGCAGAAGCCCGGCAAGGCCCCCAAGCTGC<br>TGATCTACGACACCTCCAAGCTGGCCTCCGGCGTGCCCTCCCGCTT<br>CTCCGGCTCCGGCTCCGGCACCGCCTTCACCCTGACCATCTCCTCC<br>CTGCAGCCCGACGACTTCGCCACCTACTACTGCTTCCAGTACTCCG<br>GCTACCCCTTCACCTTCGGCGGCGGCACCAAGCTGGAGATCAAAC<br>GAACTGTGGCTGCACCATCTGTCTTCATCTTCCCGCCATCTGATGA<br>GCAGTTGAAATCTGGAACTGCCTCTGTCGTGTGCCTGCTGAATAAC<br>TTCTATCCCAGAGAGGCCAAAGTACAGTGGAAGGTGGATAACGCC<br>CTCCAATCGGGTAACTCCCAGGAGAGTGTCACAGAGCAGGACAGC<br>AAGGACAGCACCTACAGCCTCAGCAGCACCCTGACGCTGAGCAAA<br>GCAGACTACGAGAAACACAAAGTCTACGCCTGCGAAGTCACCCAT<br>CAGGGCCTGTCCTCGCCCGTCACAAAGAGCTTCAACAGGGGAGAG<br>TGT |
| Palivizumab L (S92N) | 4 | GACATCCAGATGACCCAGTCCCCCTCCACCCTGTCCGCCTCCGTGG<br>GCGACCGCGTGACCATCACCTGCAAGTGCCAGCTGTCCGTGGGCT<br>ACATGCACTGGTACCAGCAGAAGCCCGGCAAGGCCCCCAAGCTGC<br>TGATCTACGACACCTCCAAGCTGGCCTCCGGCGTGCCCTCCCGCTT<br>CTCCGGCTCCGGCTCCGGCACCGCCTTCACCCTGACCATCTCCTCC<br>CTGCAGCCCGACGACTTCGCCACCTACTACTGCTTCCAGGGCAAC<br>GGCTACCCCTTCACCTTCGGCGGCGGCACCAAGCTGGAGATCAAA<br>CGAACTGTGGCTGCACCATCTGTCTTCATCTTCCCGCCATCTGATG<br>AGCAGTTGAAATCTGGAACTGCCTCTGTCGTGTGCCTGCTGAATAA<br>CTTCTATCCCAGAGAGGCCAAAGTACAGTGGAAGGTGGATAACGC<br>CCTCCAATCGGGTAACTCCCAGGAGAGTGTCACAGAGCAGGACAG<br>CAAGGACAGCACCTACAGCCTCAGCAGCACCCTGACGCTGAGCAA<br>AGCAGACTACGAGAAACACAAAGTCTACGCCTGCGAAGTCACCCA<br>TCAGGGCCTGTCCTCGCCCGTCACAAAGAGCTTCAACAGGGGAGA<br>GTGT |
| Palivizumab H | 5 | CAGGTGACCCTGCGCGAGTCCGGCCCTGCACTGGTGAAGCCCACC<br>CAGACCCTGACCCTGACCTGCACCTTCTCCGGCTTCTCCCTGTCCA<br>CCTCCGGCATGTCCGTGGGCTGGATCCGGCAGCCTCCCGGCAAGG<br>CCCTGGAGTGGCTGGCTGACATCTGGTGGGACGACAAGAAGGACT<br>ACAACCCCTCCCTGAAGTCCCGCCTGACCATCTCCAAGGACACCTC<br>CAAGAACCAGGTGGTGCTGAAGGTGACCAACATGGACCCCGCCGA<br>CACCGCCACCTACTACTGCGCCCGCTCAATGATTACCAACTGGTAC<br>TTCGACGTGTGGGGAGCCGGTACCACCGTGACCGTGTCTTCCGCCT<br>CCACCAAGGGCCCATCGGTCTTCCCCCTGGCACCCTCCTCCAAGAG<br>CACCTCTGGGGGCACAGCGGCCCTGGGCTGCCTGGTCAAGGACTA<br>CTTCCCCGAACCGGTGACGGTGTCGTGGAACTCAGGCGCCCTGAC<br>CAGCGGCGTGCACACCTTCCCGGCTGTCCTACAGTCCTCAGGACTC<br>TACTCCCTCAGCAGCGTGGTGACTGTGCCCTCTAGCAGCTTGGGCA<br>CCCAGACCTACATCTGCAACGTGAATCACAAGCCCAGCAACACCA<br>AGGTGGACAAGAAAGTTGAACCCAAATCTTGCGACAAAACTCACA<br>CATGCCCACCGTGCCCAGCACCTCCAGTCGCCGACCGTCAGTCTT<br>CCTCTTCCCTCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCG<br>TGTGGTCAGCGTCCTCACCGTCCTGCACCAGGACTGGCTGAATGG<br>CAAGGAGTACAAGTGCAAGGTCTCCAACAAAGGCCTCCCAAGCTC<br>CATCGAGAAAACCATCTCCAAAGCCAAAGGGCAGCCCCGAGAAC<br>CACAGGTGTACACCCTGCCTCCATCCCGGGATGAGCTGACCAAGA<br>ACCAGGTCAGCCTGACCTGCCTGGTCAAAGGCTTCTATCCCAGCG<br>ACATCGCCGTGGAGTGGGAGAGCAATGGGCAGCCGGAGAACAAC<br>TACAAGACCACGCCTCCCGTGCTGGACTCCGACGGCTCCTTCTTCC<br>TCTACAGCAAGCTCACCGTGGACAAGAGCAGGTGGCAGCAGGGG<br>AACGTCTTCTCATGCTCCGTGATGCATGAGGCTCTGCACAACCACT<br>ACACGCAGAAGAGCCTCTCCCTGTCTCCGGGTAAATGATAA |

TABLE 1-continued

Immunoglobulin Light Chain (LC) and Heavy Chain (HC)-Nucleotide Sequence

| NAME | SEQ ID NO | SEQUENCE |
|---|---|---|
| Palivizumab H2 | 6 | CAGGTGACCCTGCGCGAGTCCGGCCCTGCACTGGTGAAGCCCACC<br>CAGACCCTGACCCTGACCTGCACCTTCTCCGGCTTCTCCCTGTCCA<br>CCTCCGGCATGTCCGTGGGCTGGATCCGGCAGCCTCCCGGCAAGG<br>CCCTGGAGTGGCTGGCTGACATCTGGTGGGACGACAAGAAGGACT<br>ACAACCCCTCCCTGAAGTCCGCCTGACCATCTCCAAGGACACCTC<br>CAAGAACCAGGTGGTGCTGAAGGTGACCAACATGGACCCCGCCGA<br>CACCGCCACCTACTACTGCGCCCGCTCAATGATTACCAACGCCTAC<br>TTCGACGTGTGGGGAGCCGGTACCACCGTGACCGTGTCTTCCGCCT<br>CCACCAAGGGCCCATCGGTCTTCCCCCTGGCACCCTCCTCCAAGAG<br>CACCTCTGGGGGCACAGCGGCCCTGGGCTGCCTGGTCAAGGACTA<br>CTTCCCCGAACCGGTGACGGTGTCGTGGAACTCAGGCGCCCTGAC<br>CAGCGGCGTGCACACCTTCCCGGCTGTCCTACAGTCCTCAGGACTC<br>TACTCCCTCAGCAGCGTGGTGACTGTGCCCTCTAGCAGCTTGGGCA<br>CCCAGACCTACATCTGCAACGTGAATCACAAGCCCAGCAACACCA<br>AGGTGGACAAGAAAGTTGAACCCAAATCTTGCGACAAAACTCACA<br>CATGCCCACCGTGCCCAGCACCTCCAGTCGCCGGACCGTCAGTCTT<br>CCTCTTCCCTCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCG<br>TGTGGTCAGCGTCCTCACCGTCCTGCACCAGGACTGGCTGAATGG<br>CAAGGAGTACAAGTGCAAGGTCTCCAACAAAGGCCTCCCAAGCTC<br>CATCGAGAAAACCATCTCCAAAGCCAAAGGGCAGCCCCGAGAAC<br>CACAGGTGTACACCCTGCCTCCATCCCGGGATGAGCTGACCAAGA<br>ACCAGGTCAGCCTGACCTGCCTGGTCAAAGGCTTCTATCCCAGCG<br>ACATCGCCGTGGAGTGGGAGAGCAATGGGCAGCCGGAGAACAAC<br>TACAAGACCACGCCTCCCGTGCTGGACTCCGACGGCTCCTTCTTCC<br>TCTACAGCAAGCTCACCGTGGACAAGAGCAGGTGGCAGCAGGGG<br>AACGTCTTCTCATGCTCCGTGATGCATGAGGCTCTGCACAACCACT<br>ACACGCAGAAGAGCCTCTCCCTGTCTCCGGGTAAATGATAA |
| Palivizumab H3 | 7 | CAGGTGACCCTGCGCGAGTCCGGCCCTGCACTGGTGAAGCCCACC<br>CAGACCCTGACCCTGACCTGCACCTTCTCCGGCTTCTCCCTGTCCA<br>CCTCCGGCATGTCCGTGGGCTGGATCCGGCAGCCTCCCGGCAAGG<br>CCCTGGAGTGGCTGGCTGACATCTGGTGGGACGACAAGAAGGACT<br>ACAACCCCTCCCTGAAGTCCGCCTGACCATCTCCAAGGACACCTC<br>CAAGAACCAGGTGGTGCTGAAGGTGACCAACATGGACCCCGCCGA<br>CACCGCCACCTACTACTGCGCCCGCTCAATGATTACCAACGGCTAC<br>TTCGACGTGTGGGGAGCCGGTACCACCGTGACCGTGTCTTCCGCCT<br>CCACCAAGGGCCCATCGGTCTTCCCCCTGGCACCCTCCTCCAAGAG<br>CACCTCTGGGGGCACAGCGGCCCTGGGCTGCCTGGTCAAGGACTA<br>CTTCCCCGAACCGGTGACGGTGTCGTGGAACTCAGGCGCCCTGAC<br>CAGCGGCGTGCACACCTTCCCGGCTGTCCTACAGTCCTCAGGACTC<br>TACTCCCTCAGCAGCGTGGTGACTGTGCCCTCTAGCAGCTTGGGCA<br>CCCAGACCTACATCTGCAACGTGAATCACAAGCCCAGCAACACCA<br>AGGTGGACAAGAAAGTTGAACCCAAATCTTGCGACAAAACTCACA<br>CATGCCCACCGTGCCCAGCACCTCCAGTCGCCGGACCGTCAGTCTT<br>CCTCTTCCCTCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCG<br>TGTGGTCAGCGTCCTCACCGTCCTGCACCAGGACTGGCTGAATGG<br>CAAGGAGTACAAGTGCAAGGTCTCCAACAAAGGCCTCCCAAGCTC<br>CATCGAGAAAACCATCTCCAAAGCCAAAGGGCAGCCCCGAGAAC |

TABLE 1-continued

Immunoglobulin Light Chain (LC) and Heavy Chain (HC)-Nucleotide Sequence

| NAME | SEQ ID NO | SEQUENCE |
|---|---|---|
| | | CACAGGTGTACACCCTGCCTCCATCCCGGGATGAGCTGACCAAGA |
| | | ACCAGGTCAGCCTGACCTGCCTGGTCAAAGGCTTCTATCCCAGCG |
| | | ACATCGCCGTGGAGTGGGAGAGCAATGGGCAGCCGGAGAACAAC |
| | | TACAAGACCACGCCTCCCGTGCTGGACTCCGACGGCTCCTTCTTCC |
| | | TCTACAGCAAGCTCACCGTGGACAAGAGCAGGTGGCAGCAGGGG |
| | | AACGTCTTCTCATGCTCCGTGATGCATGAGGCTCTGCACAACCACT |
| | | ACACGCAGAAGAGCCTCTCCCTGTCTCCGGGTAAATGATAA |
| Palivizumab H4 | 8 | CAGGTGACCCTGCGCGAGTCCGGCCCTGCACTGGTGAAGCCCACC |
| | | CAGACCCTGACCCTGACCTGCACCTTCTCCGGCTTCTCCCTGTCCA |
| | | CCTCCGGCATGTCCGTGGGCTGGATCCGGCAGCCTCCCGGCAAGG |
| | | CCCTGGAGTGGCTGGCTGACATCTGGTGGGACGACAAGAAGGACT |
| | | ACAACCCCTCCCTGAAGTCCCGCCTGACCATCTCCAAGGACACCTC |
| | | CAAGAACCAGGTGGTGCTGAAGGTGACCAACATGGACCCCGCCGA |
| | | CACCGCCACCTACTACTGCGCCCGCTCAATGATTACCTTCGGGGGC |
| | | TTCGACGTGTGGGGAGCCGGTACCACCGTGACCGTGTCTTCCGCCT |
| | | CCACCAAGGGCCCATCGGTCTTCCCCCTGGCACCCTCCTCCAAGAG |
| | | CACCTCTGGGGGCACAGCGGCCCTGGGCTGCCTGGTCAAGGACTA |
| | | CTTCCCCGAACCGGTGACGGTGTCGTGGAACTCAGGCGCCCTGAC |
| | | CAGCGGCGTGCACACCTTCCCGGCTGTCCTACAGTCCTCAGGACTC |
| | | TACTCCCTCAGCAGCGTGGTGACTGTGCCCTCTAGCAGCTTGGGCA |
| | | CCCAGACCTACATCTGCAACGTGAATCACAAGCCCAGCAACACCA |
| | | AGGTGGACAAGAAAGTTGAACCCAAATCTTGCGACAAAACTCACA |
| | | CATGCCCACCGTGCCCAGCACCTCCAGTCGCCGGACCGTCAGTCTT |
| | | CCTCTTCCCTCCAAAACCCAAGGACACCCTCATGATCTCCCGGACC |
| | | CCTGAGGTCACATGCGTGGTGGTGGACGTGAGCCACGAAGACCCT |
| | | GAGGTCAAGTTCAACTGGTACGTGGACGGCGTGGAGGTGCATAAT |
| | | GCCAAGACAAAGCCGCGGGAGGAGCAGTACAACAGCACGTACCG |
| | | TGTGGTCAGCGTCCTCACCGTCCTGCACCAGGACTGGCTGAATGG |
| | | CAAGGAGTACAAGTGCAAGGTCTCCAACAAAGGCCTCCCAAGCTC |
| | | CATCGAGAAAACCATCTCCAAAGCCAAAGGGCAGCCCCGAGAAC |
| | | CACAGGTGTACACCCTGCCTCCATCCCGGGATGAGCTGACCAAGA |
| | | ACCAGGTCAGCCTGACCTGCCTGGTCAAAGGCTTCTATCCCAGCG |
| | | ACATCGCCGTGGAGTGGGAGAGCAATGGGCAGCCGGAGAACAAC |
| | | TACAAGACCACGCCTCCCGTGCTGGACTCCGACGGCTCCTTCTTCC |
| | | TCTACAGCAAGCTCACCGTGGACAAGAGCAGGTGGCAGCAGGGG |
| | | AACGTCTTCTCATGCTCCGTGATGCATGAGGCTCTGCACAACCACT |
| | | ACACGCAGAAGAGCCTCTCCCTGTCTCCGGGTAAATGATAA |

TABLE 2

Immunoglobulin Light Chain (LC) and Heavy Chain (HC)-Amino Acid Sequence

| Name | SEQ ID NO | Sequence |
|---|---|---|
| Palivizumab L | 9 | DIQMTQSPSTLSASVGDRVTITCKCQLSVGYMHWYQQKPGKAPKLLI YDTSKLASGVPSRFSGSGSGTEFTLTISSLQPDDFATYYCFQGSGYPFT FGGGTKLEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| Palivizumab L (germline) | 10 | DIQMTQSPSTLSASVGDRVTITCKCQLSVGYMHWYQQKPGKAPKLLI YDTSKLASGVPSRFSGSGSGTAFTLTISSLQPDDFATYYCFQGSGYPFT FGGGTKLEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| Palivizumab L (G91Y) | 11 | DIQMTQSPSTLSASVGDRVTITCKCQLSVGYMHWYQQKPGKAPKLLI YDTSKLASGVPSRFSGSGSGTAFTLTISSLQPDDFATYYCFQYSGYPFT FGGGTKLEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| Palivizumab L (S92N) | 12 | DIQMTQSPSTLSASVGDRVTITCKCQLSVGYMHWYQQKPGKAPKLLI YDTSKLASGVPSRFSGSGSGTAFTLTISSLQPDDFATYYCFQGNYPFT FGGGTKLEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| Paliv TABLE 2-continued Immunoglobulin Light Chain (LC) and Heavy Chain (HC)-Amino Acid Sequence

| Name | SEQ ID NO | Sequence |
|---|---|---|
| | | EVHNAKTKPREEQYNSTYRVVSVLTVLHQDWLNGKEYKCKVSNKG LPSSIEKTISKAKGQPREPQVYTLPPSRDELTKNQVSLTCLVKGFYPSD IAVEWESNGQPENNYKTTPPVLDSDGSFFLYSKLTVDKSRWQQGNVF SCSVMHEALHNHYTQKSLSLSPGK |

TABLE 3

Immunoglobulin fusion protein-Nucleotide Sequence

| NAME | SEQ ID NO | SEQUENCE |
|---|---|---|
| Palivizumab (NH1, 16GS) Relaxin2 (9GS) | 17 | GACTCTTGGATGGAAGAAGTTATCAAACTGTGCGGTCGTGAACTGG TTCGTGCTCAGATCGCTATCTGCGGTATGTCTACCTGGTCTGGCGG GGGTGGGAGCGGGGGAGGCGGACAGCTGTACTCTGCTCTGGCTA ACAAATGCTGCCACGTTGGTTGCACCAAACGTTCTCTGGCTCGTTT CTGCGGCGGAGGCGGATCCGGAGGCGGAGGTTCCGGCGGGGG TGGGAGCGGGCAGGTGACCCTGCGCGAGTCCGGCCCTGCACT GGTGAAGCCCACCCAGACCCTGACCCTGACCTGCACCTTCTCC GGCTTCTCCCTGTCCACCTCCGGCATGTCCGTGGGCTGGATCC GGCAGCCTCCCGGCAAGGCCCTGGAGTGGCTGGCTGACATCTG GTGGGACGACAAGAAGGACTACAACCCCTCCCTGAAGTCCCG CCTGACCATCTCCAAGGACACCTCCAAGAACCAGGTGGTGCTG AAGGTGACCAACATGGACCCCGCCGACACCGCCACCTACTACT GCGCCCGCTCAATGATTACCAACGCCTACTTCGACGTGTGGGG AGCCGGTACCACCGTGACCGTGTCTTCCGCCTCCACCAAGGGC CCATCGGTCTTCCCCCTGGCACCCTCCTCCAAGAGCACCTCTG GGGGCACAGCGGCCCTGGGCTGCCTGGTCAAGGACTACTTCCC CGAACCGGTGACGGTGTCGTGGAACTCAGGCGCCCTGACCAG CGGCGTGCACACCTTCCCGGCTGTCCTACAGTCCTCAGGACTC TACTCCCTCAGCAGCGTGGTGACTGTGCCCTCTAGCAGCTTGG GCACCCAGACCTACATCTGCAACGTGAATCACAAGCCCAGCA ACACCAAGGTGGACAAGAAAGTTGAACCCAAATCTTGCGACA AAACTCACACATGCCCACCGTGCCCAGCACCTCCAGTCGCCGG ACCGTCAGTCTTCCTCTTCCCTCCAAAACCCAAGGACACCCTC ATGATCTCCCGGACCCCTGAGGTCACATGCGTGGTGGTGGACG TGAGCCACGAAGACCCTGAGGTCAAGTTCAACTGGTACGTGG ACGGCGTGGAGGTGCATAATGCCAAGACAAAGCCGCGGGAGG AGCAGTACAACAGCACGTACCGTGTGGTCAGCGTCCTCACCGT CCTGCACCAGGACTGGCTGAATGGCAAGGAGTACAAGTGCAA GGTCTCCAACAAAGGCCTCCCAAGCTCCATCGAGAAAACCATC TCCAAAGCCAAAGGGCAGCCCCGAGAACCACAGGTGTACACC CTGCCTCCATCCCGGGATGAGCTGACCAAGAACCAGGTCAGCC TGACCTGCCTGGTCAAAGGCTTCTATCCCAGCGACATCGCCGT |

TABLE 3-continued

| Immunoglobulin fusion protein-Nucleotide Sequence | | |
|---|---|---|
| NAME | SEQ ID NO | SEQUENCE |
| | | GGAGTGGGAGAGCAATGGGCAGCCGGAGAACAACTACAAGAC |
| | | CACGCCTCCCGTGCTGGACTCCGACGGCTCCTTCTTCCTCTACA |
| | | GCAAGCTCACCGTGGACAAGAGCAGGTGGCAGCAGGGGAACG |
| | | TCTTCTCATGCTCCGTGATGCATGAGGCTCTGCACAACCACTA |
| | | CACGCAGAAGAGCCTCTCCCTGTCTCCGGGTAAATGATAA |
| Palivizumab (NH2, 16GS) Relaxin2 (9GS) | 18 | *GACTCTTGGATGGAAGAAGTTATCAAACTGTGCGGTCGTGAACTGG* *TTCGTGCTCAGATCGCTATCTGCGGTATGTCTACCTGGTCT*GGCGG |
| | | GGGTGGGAGCGGGGGAGGCGGACAGCTGTACTCTGCTCTGGCTA |
| | | ACAAATGCTGCCACGTTGGTTGCACCAAACGTTCTCTGGCTCGTTT |
| | | CTGCGGCGGAGGCGGATCCGGAGGCGGAGGTTCCGGCGGGGG |
| | | TGGGAGCGGGCAGGTGACCCTGCGCGAGTCCGGCCCTGCACT |
| | | GGTGAAGCCCACCCAGACCCTGACCCTGACCTGCACCTTCTCC |
| | | GGCTTCTCCCTGTCCACCTCCGGCATGTCCGTGGGCTGGATCC |
| | | GGCAGCCTCCCGGCAAGGCCCTGGAGTGGCTGGCTGACATCTG |
| | | GTGGGACGACAAGAAGGACTACAACCCCTCCCTGAAGTCCCG |
| | | CCTGACCATCTCCAAGGACACCTCCAAGAACCAGGTGGTGCTG |
| | | AAGGTGACCAACATGGACCCCGCCGACACCGCCACCTACTACT |
| | | GCGCCCGCTCAATGATTACCAACGGCTACTTCGACGTGTGGGG |
| | | AGCCGGTACCACCGTGACCGTGTCTTCCGCCTCCACCAAGGGC |
| | | CCATCGGTCTTCCCCCTGGCACCCTCCTCCAAGAGCACCTCTG |
| | | GGGGCACAGCGGCCCTGGGCTGCCTGGTCAAGGACTACTTCCC |
| | | CGAACCGGTGACGGTGTCGTGGAACTCAGGCGCCCTGACCAG |
| | | CGGCGTGCACACCTTCCCGGCTGTCCTACAGTCCTCAGGACTC |
| | | TACTCCCTCAGCAGCGTGGTGACTGTGCCCTCTAGCAGCTTGG |
| | | GCACCCAGACCTACATCTGCAACGTGAATCACAAGCCCAGCA |
| | | ACACCAAGGTGGACAAGAAAGTTGAACCCAAATCTTGCGACA |
| | | AAACTCACACATGCCCACCGTGCCCAGCACCTCCAGTCGCCGG |
| | | ACCGTCAGTCTTCCTCTTCCCTCCAAAACCCAAGGACACCCTC |
| | | ATGATCTCCCGGACCCCTGAGGTCACATGCGTGGTGGTGGACG |
| | | TGAGCCACGAAGACCCTGAGGTCAAGTTCAACTGGTACGTGG |
| | | ACGGCGTGGAGGTGCATAATGCCAAGACAAAGCCGCGGGAGG |
| | | AGCAGTACAACAGCACGTACCGTGTGGTCAGCGTCCTCACCGT |
| | | CCTGCACCAGGACTGGCTGAATGGCAAGGAGTACAAGTGCAA |
| | | GGTCTCCAACAAAGGCCTCCCAAGCTCCATCGAGAAAACCATC |
| | | TCCAAAGCCAAAGGGCAGCCCCGAGAACCACAGGTGTACACC |
| | | CTGCCTCCATCCCGGGATGAGCTGACCAAGAACCAGGTCAGCC |

TABLE 3-continued

Immunoglobulin fusion protein-Nucleotide Sequence

| NAME | SEQ ID NO | SEQUENCE |
|------|-----------|----------|
| | | TGACCTGCCTGGTCAAAGGCTTCTATCCCAGCGACATCGCCGT |
| | | GGAGTGGGAGAGCAATGGGCAGCCGGAGAACAACTACAAGAC |
| | | CACGCCTCCCGTGCTGGACTCCGACGGCTCCTTCTTCCTCTACA |
| | | GCAAGCTCACCGTGGACAAGAGCAGGTGGCAGCAGGGGAACG |
| | | TCTTCTCATGCTCCGTGATGCATGAGGCTCTGCACAACCACTA |
| | | CACGCAGAAGAGCCTCTCCCTGTCTCCGGGTAAATGATAA |
| Palivizumab (NH3, 16GS) | 19 | *GACTCTTGGATGGAAGAAGTTATCAAACTGTGCGGTCGTGAACTGG* |
| | | *TTCGTGCTCAGATCGCTATCTGCGGTATGTCTACCTGGTCTGGCGG* |
| Relaxin2 (9GS) | | *GGGTGGGAGCGGGGGAGGCGGACAGCTGTACTCTGCTCTGGCTA* |
| | | *ACAAATGCTGCCACGTTGGTTGCACCAAACGTTCTCTGGCTCGTTT* |
| | | *CTGCGGCGGAGGCGGATCCGGAGGCGGAGGTTCCGGCGGGG* |
| | | TGGGAGCGGGCAGGTGACCCTGCGCGAGTCCGGCCCTGCACT |
| | | GGTGAAGCCCACCCAGACCCTGACCCTGACCTGCACCTTCTCC |
| | | GGCTTCTCCCTGTCCACCTCCGGCATGTCCGTGGGCTGGATCC |
| | | GGCAGCCTCCCGGCAAGGCCCTGGAGTGGCTGGCTGACATCTG |
| | | GTGGGACGACAAGAAGGACTACAACCCCTCCCTGAAGTCCCG |
| | | CCTGACCATCTCCAAGGACACCTCCAAGAACCAGGTGGTGCTG |
| | | AAGGTGACCAACATGGACCCCGCCGACACCGCCACCTACTACT |
| | | GCGCCCGCTCAATGATTACCTTCGGGGGCTTCGACGTGTGGGG |
| | | AGCCGGTACCACCGTGACCGTGTCTTCCGCCTCCACCAAGGGC |
| | | CCATCGGTCTTCCCCCTGGCACCCTCCTCCAAGAGCACCTCTG |
| | | GGGGCACAGCGGCCCTGGGCTGCCTGGTCAAGGACTACTTCCC |
| | | CGAACCGGTGACGGTGTCGTGGAACTCAGGCGCCCTGACCAG |
| | | CGGCGTGCACACCTTCCCGGCTGTCCTACAGTCCTCAGGACTC |
| | | TACTCCCTCAGCAGCGTGGTGACTGTGCCCTCTAGCAGCTTGG |
| | | GCACCCAGACCTACATCTGCAACGTGAATCACAAGCCCAGCA |
| | | ACACCAAGGTGGACAAGAAAGTTGAACCCAAATCTTGCGACA |
| | | AAACTCACACATGCCCACCGTGCCCAGCACCTCCAGTCGCCGG |
| | | ACCGTCAGTCTTCCTCTTCCCTCCAAAACCCAAGGACACCCTC |
| | | ATGATCTCCCGGACCCCTGAGGTCACATGCGTGGTGGTGGACG |
| | | TGAGCCACGAAGACCCTGAGGTCAAGTTCAACTGGTACGTGG |
| | | ACGGCGTGGAGGTGCATAATGCCAAGACAAAGCCGCGGGAGG |
| | | AGCAGTACAACAGCACGTACCGTGTGGTCAGCGTCCTCACCGT |
| | | CCTGCACCAGGACTGGCTGAATGGCAAGGAGTACAAGTGCAA |
| | | GGTCTCCAACAAAGGCCTCCCAAGCTCCATCGAGAAAACCATC |
| | | TCCAAAGCCAAAGGGCAGCCCCGAGAACCACAGGTGTACACC |
| | | CTGCCTCCATCCCGGGATGAGCTGACCAAGAACCAGGTCAGCC |
| | | TGACCTGCCTGGTCAAAGGCTTCTATCCCAGCGACATCGCCGT |
| | | GGAGTGGGAGAGCAATGGGCAGCCGGAGAACAACTACAAGAC |
| | | CACGCCTCCCGTGCTGGACTCCGACGGCTCCTTCTTCCTCTACA |
| | | GCAAGCTCACCGTGGACAAGAGCAGGTGGCAGCAGGGGAACG |

TABLE 3-continued

Immunoglobulin fusion protein-Nucleotide Sequence

| NAME | SEQ ID NO | SEQUENCE |
|---|---|---|
| | | TCTTCTCATGCTCCGTGATGCATGAGGCTCTGCACAACCACTA |
| | | CACGCAGAAGAGCCTCTCCCTGTCTCCGGGTAAATGATAA |

For SEQ ID NOs: 17-19
Immunoglobulin Region = dashed underline
Peptide/Therapeutic peptide = italic
Peptide/Therapeutic peptide internal linker = italic
Connecting peptide = bold, thick underline
Linker = double underline
Protease site: underline

TABLE 4

Immunoglobulin fusion protein-Amino Acid Sequence

| Name | SEQ ID NO | Sequence |
|---|---|---|
| Palivizumab (NH1, 16GS) Relaxin2 (9GS) | 20 | *DSWMEEVIKLCGRELVRAQIAICGMSTWS*GGGGSGGGGQ*LYSALAN KCCHVGCTKRSLARF*CGGGGSGGGGSGGGGSGQVTLRESGPALV KPTQTLTLTCTFSGFSLSTSGMSVGWIRQPPGKALEWLADIWWD DKKDYNPSLKSRLTISKDTSKNQVVLKVTNMDPADTATYYCARS MITNAYFDVWGAGTTVTVSSASTKGPSVFPLAPSSKSTSGGTAAL GCLVKDYFPEPVTVSWNSGALTSGVHTFPAVLQSSGLYSLSSVVT VPSSSLGTQTYICNVNHKPSNTKVDKKVEPKSCDKTHTCPPCPAP PVAGPSVFLFPPKPKDTLMISRTPEVTCVVVDVSHEDPEVKFNWY VDGVEVHNAKTKPREEQYNSTYRVVSVLTVLHQDWLNGKEYKC KVSNKGLPSSIEKTISKAKGQPREPQVYTLPPSRDELTKNQVSLTC LVKGFYPSDIAVEWESNGQPENNYKTTPPVLDSDGSFFLYSKLTV DKSRWQQGNVFSCSVMHEALHNHYTQKSLSLSPGK |
| Palivizumab (NH2, 16GS) Relaxin2 (9GS) | 21 | *DSWMEEVIKLCGRELVRAQIAICGMSTWS*GGGGSGGGGQ*LYSALAN KCCHVGCTKRSLARF*CGGGGSGGGGSGGGGSGQVTLRESGPALV KPTQTLTLTCTFSGFSLSTSGMSVGWIRQPPGKALEWLADIWWD DKKDYNPSLKSRLTISKDTSKNQVVLKVTNMDPADTATYYCARS MITNAYFDVWGAGTTVTVSSASTKGPSVFPLAPSSKSTSGGTAAL GCLVKDYFPEPVTVSWNSGALTSGVHTFPAVLQSSGLYSLSSVVT VPSSSLGTQTYICNVNHKPSNTKVDKKVEPKSCDKTHTCPPCPAP PVAGPSVFLFPPKPKDTLMISRTPEVTCVVVDVSHEDPEVKFNWY VDGVEVHNAKTKPREEQYNSTYRVVSVLTVLHQDWLNGKEYKC KVSNKGLPSSIEKTISKAKGQPREPQVYTLPPSRDELTKNQVSLTC LVKGFYPSDIAVEWESNGQPENNYKTTPPVLDSDGSFFLYSKLTV DKSRWQQGNVFSCSVMHEALHNHYTQKSLSLSPGK |
| Palivizumab (NH3, 16GS) Relaxin2 (9GS) | 22 | *DSWMEEVIKLCGRELVRAQIAICGMSTWS*GGGGSGGGGQ*LYSALAN KCCHVGCTKRSLARF*CGGGGSGGGGSGGGGSGQVTLRESGPALV KPTQTLTLTCTFSGFSLSTSGMSVGWIRQPPGKALEWLADIWWD DKKDYNPSLKSRLTISKDTSKNQVVLKVTNMDPADTATYYCARS MITNAYFDVWGAGTTVTVSSASTKGPSVFPLAPSSKSTSGGTAAL |

TABLE 4-continued

Immunoglobulin fusion protein-Amino Acid Sequence

| Name | SEQ ID NO | Sequence |
|------|-----------|----------|
|  |  | GCLVKDYFPEPVTVSWNSGALTSGVHTFPAVLQSSGLYSLSSVVT |
|  |  | VPSSSLGTQTYICNVNHKPSNTKVDKKVEPKSCDKTHTCPPCPAP |
|  |  | PVAGPSVFLFPPKPKDTLMISRTPEVTCVVVDVSHEDPEVKFNWY |
|  |  | VDGVEVHNAKTKPREEQYNSTYRVVSVLTVLHQDWLNGKEYKC |
|  |  | KVSNKGLPSSIEKTISKAKGQPREPQVYTLPPSRDELTKNQVSLTC |
|  |  | LVKGFYPSDIAVEWESNGQPENNYKTTPPVLDSDGSFFLYSKLTV |
|  |  | DKSRWQQGNVFSCSVMHEALHNHYTQKSLSLSPGK |

For SEQ ID NOs: 20-22
Immunoglobulin region = dashed underline
Peptide/Therapeutic peptide = italic
Peptide/Therapeutic peptide internal linker = italic
Connecting peptide = bold, thick underline
Linker = double underline
Protease site: underline

TABLE 5

Therapeutic Peptides-Nucleotide Sequence

| NAME | SEQ ID NO | SEQUENCE |
|------|-----------|----------|
| Relaxin2 | 23 | *GACTCTTGGATGGAAGAAGTTATCAAACTGTGCGGTCGTGAACTGG TTCGTGCTCAGATCGCTATCTGCGGTATGTCTACCTGGTCTAAACG TTCTCTGTCTCAGGAAGACGCTCCGCAGACCCCGCGTCCGGTTGC TGAAATCGTTCCGTCTTTCATCAACAAAGACACCGAAACCATCAACA TGATGTCTGAATTCGTTGCTAACCTGCCGCAGGAACTGAAACTGAC CCTGTCTGAAATGCAGCCGGCTCTGCCGCAGCTGCAGCAGCACGT TCCGGTTCTGAAAGACTCTTCTCTGCTGTTCGAAGAATTCAAAAAAC TGATCCGTAACCGTCAGTCTGAAGCTGCTGACTCTTCTCCGTCTGA ACTGAAATACCTGGGTCTGGACACCCACTCTCGTAAAAAACGTCAG CTGTACTCTGCTCTGGCTAACAAATGCTGCCACGTTGGTTGCACCA AACGTTCTCTGGCTCGTTTCTGC* |
| Relaxin2 (XT100) | 24 | *GACTCTTGGATGGAAGAAGTTATCAAACTGTGCGGTCGTGAACTGG TTCGTGCTCAGATCGCTATCTGCGGTATGTCTACCTGGTCTAAACG* TGGAGGTGGCGGGAGCGGCACTTCTGAGTCTGCTACTCCAGAAAG CGGCCCAGGTTCTGAACCAGCAACTTCTGGCTCTGAGACTCCAGG CACTTCTGAGTCCGCAACGCCTGAATCCGGTCCTGGTTCTGAACCA GCTACTTCCGGCAGCGAAACCCCAGGTACCGGAGGTGGCGGGAG CCACCATCACCACCACCACGGAGGTGGCGGGAGCTCTGAGTCTGC GACTCCAGAGTCTGGTCCTGGTACTTCCACTGAGCCTAGCGAGGG TTCCGCACCAGGTTCTCCGGCTGGTAGCCCGACCAGCACGGAGGA GGGTACGTCTGAATCTGCAACGCCGGAATCGGGCCCAGGTTCGGA GGGAGGAGGTGGCGGGAGCCGTAAAAAACGTCAGCTGTACTCTG *CTCTGGCTAACAAATGCTGCCACGTTGGTTGCACCAAACGTTCTCT GGCTCGTTTCTGC* |
| Relaxin2 (XT35) | 25 | *GACTCTTGGATGGAAGAAGTTATCAAACTGTGCGGTCGTGAACTGG TTCGTGCTCAGATCGCTATCTGCGGTATGTCTACCTGGTCTAAACG* TGGAGGTGGCGGGAGCTCTGGCAGCGAAACCCCGGGTACCTCCG AATCTGCTACACCGGAAAGCGGTGGAGGTGGCGGGAGCCACCAT CACCACCACCACGGAGGTGGCGGGAGCCCTGGCAGCCCTGGTCC GGGCACTAGCACCGAGCCATCGGAGGGCTCCGCACCAGGAGGTG |

TABLE 5-continued

Therapeutic Peptides-Nucleotide Sequence

| NAME | SEQ ID NO | SEQUENCE |
|---|---|---|
| | | GCGGGAGCCGTAAAAAACGTCAGCTGTACTCTGCTCTGGCTAACA |
| | | AATGCTGCCACGTTGGTTGCACCAAACGTTCTCTGGCTCGTTTCTG C |
| Relaxin2 (single) | 26 | GACTCTTGGATGGAAGAAGTTATCAAACTGTGCGGTCGTGAACTGG TTCGTGCTCAGATCGCTATCTGCGGTATGTCTACCTGGTCTTCTGG |
| | | CAGCGAAACCCCGGGTACCTCCGAATCTGCTACACCGGAAAGCGG |
| | | TCCTGGCAGCCCTGGTCCGGGCACTAGCACCGAGCCATCGGAGG |
| | | GCTCCGCACCACAGCTGTACTCTGCTCTGGCTAACAAATGCTGCCA |
| | | CGTTGGTTGCACCAAACGTTCTCTGGCTCGTTTCTGC |
| Relaxin2 (insulin C peptide) | 27 | GACTCTTGGATGGAAGAAGTTATCAAACTGTGCGGTCGTGAACTGG TTCGTGCTCAGATCGCTATCTGCGGTATGTCTACCTGGTCTCGTCG |
| | | TGAAGCTGAAGACCTGCAGGTTGGTCAGGTTGAACTGGGTGGTGG |
| | | TCCGGGTGCTGGTTCTCTGCAGCCGCTGGCTCTGGAAGGTTCTCT |
| | | GCAGAAACGTCAGCTGTACTCTGCTCTGGCTAACAAATGCTGCCAC |
| | | GTTGGTTGCACCAAACGTTCTCTGGCTCGTTTCTGC |
| Relaxin2 (XT21) | 28 | GACTCTTGGATGGAAGAAGTTATCAAACTGTGCGGTCGTGAACTGG TTCGTGCTCAGATCGCTATCTGCGGTATGTCTAC |
| | | CTGGTCTTCTGGCAGCGAAACCCCGGGTACCTCCGAATCTGCTAC |
| | | ACCGGAAAGCGGTCCTGGCAGCCCTCAGCTGTACT |
| | | CTGCTCTGGCTAACAAATGCTGCCACGTTGGTTGCACCAAACGTTC TCTGGCTCGTTTCTGC |
| Relaxin2a | 29 | GACTCTTGGATGGAAGAAGTTATCAAACTGTGCGGTCGTGAACTGG TTCGTGCTCAGATCGCTATCTGCGGTATGTCTACCTGGTCTAAACG T |
| Relaxin2b | 30 | CGTAAAAAACGTCAGCTGTACTCTGCTCTGGCTAACAAATGCTGCC ACGTTGGTTGCACCA4ACGTTCTCTGGCTCGTTTCTGC |
| Relaxin2 (30GS) | 31 | GACTCTTGGATGGAAGAAGTTATCAAACTGTGCGGTCGTGAACTGG TTCGTGCTCAGATCGCTATCTGCGGTATGTCTACCTGGTCTGGCGG |
| | | GGGAGGCAGCGGGGGAGGCGGGTCCGGAGGCGGGGGATCTGGC |
| | | GGGGGAGGCAGTGGGGGAGGCGGGAGCGGAGGCGGGGGCTCT |
| | | CAGCTGTACTCTGCTCTGGCTAACAAATGCTGCCACGTTGGTTGCA CCAAACGTTCTCTGGCTCGTTTCTGC |
| Relaxin2 Q60A (30GS) | 32 | GACTCTTGGATGGAAGAAGTTATCAAACTGTGCGGTCGTGAACTGG TTCGTGCTCAGATCGCTATCTGCGGTATGTCTACCTGGTCTGGCGG |
| | | GGGAGGCAGCGGGGGAGGCGGGTCCGGAGGCGGGGGATCTGGC |
| | | GGGGGAGGCAGTGGGGGAGGCGGGAGCGGAGGCGGGGGCCCT |
| | | GCGCTGTACTCTGCTCTGGCTAACAAATGCTGCCACGTTGGTTGCA CCAAACGTTCTCTGGCTCGTTCTGC |
| Relaxin2 (9GS) | 33 | GACTCTTGGATGGAAGAAGTTATCAAACTGTGCGGTCGTGAACTGG TTCGTGCTCAGATCGCTATCTGCGGTATGTCTACCTGGTCTGGCGG |
| | | GGGTGGGAGCGGGGGAGGCGGACAGCTGTACTCTGCTCTGGCTA |
| | | ACAAATGCTGCCACGTTGGTTGCACCAAACGTTCTCTGGCTCGTTT CTGC |
| Relaxin2c (9GS) | 34 | GATTCATGGATGGAGGAGGTCATCAAACTGTGTGGCAGGGAGCTG GTGAGAGCACAGATCGCTATCTGTGGGATGAGCACCTGGAGTGGC |
| | | GGGGGAGGGAGCGGGGGAGGCGGACAGCTGTACTCTGCACTGG |
| | | CCAATAAATGCTGCCACGTGGGATGTACCAAGAGATCTCTGGCAC GGTTTTGT |

TABLE 5-continued

Therapeutic Peptides-Nucleotide Sequence

| NAME | SEQ ID NO | SEQUENCE |
|---|---|---|
| Relaxin2 (GGGPRR) | 35 | GACTCTTGGATGGAAGAAGTTATCAAACTGTGCGGTCGTGAACTGG<br>TTCGTGCTCAGATCGCTATCTGCGGTATGTCTACCTGGTCTGGCGG<br>AGGGCCCCGCCGGCAGCTGTACTCTGCTCTGGCTAACAAATGCTG<br>CCACGTTGGTTGCACCAAACGTTCTCTGGCTCGTTTCTGC |
| Relaxin2 (18GS) | 36 | GACTCTTGGATGGAAGAAGTTATCAAACTGTGCGGTCGTGAACTGG<br>TTCGTGCTCAGATCGCTATCTGCGGTATGTCTACCTGGTCTGGCGG<br>AGGCGGATCCGGGGGCGGGGGTTCCGGCGGGGGTGGGAGCGG<br>GGGAGGCCAGCTGTACTCTGCTCTGGCTAACAAATGCTGCCACGT<br>TGGTTGCACCAAACGTTCTCTGGCTCGTTTCTGC |

For SEQ ID NOs: 23-36
Immunoglobulin Region = dashed underline
Peptide/Therapeutic peptide = italic
Peptide/Therapeutic peptide internal linker = italic
Connecting peptide = bold, thick underline
Linker = double underline
Protease site: underline

TABLE 6

Therapeutic Peptides-Amino Acid Sequence

| Name | SEQ ID NO | Sequence |
|---|---|---|
| Relaxin2 | 37 | DSWMEEVIKLCGRELVRAQIAICGMSTWSKRSLSQEDAPQTPRPVAEI<br>VPSFINKDTETINMNISEFVANLPQELKLTLSEMQPALPQLQQHVPVL<br>KDSSLLFEEFKKLIRNRQSEAADSSPSELKYLGLDTHSRKKRQLYSALA<br>NKCCHVGCTKRSLARFC |
| Relaxin2 (XT100) | 38 | DSWMEEVIKLCGRELVRAQIAICGMSTWSKRGGGGSGTSESATPESG<br>PGSEPATSGSETPGTSESATPESGPGSEPATSGSETPGTGGGGSHHHH<br>HHGGGGSSESATPESGPGTSTEPSEGSAPGSPAGSPTSTEEGTSESATP<br>ESGPGSEGGGGGSRKKRQLYSALANKCCHVGCTKRSLARFC |
| Relaxin2 (XT35) | 39 | DSWMEEVIKLCGRELVRAQIAICGMSTWSKRGGGGSSGSETPGTSESA<br>TPESGGGGGSHHHHHHGGGGSPGSPGPGTSTEPSEGSAPGGGGSR<br>KKRQLYSALANKCCHVGCTKRSLARFC |
| Relaxin2 (single) | 40 | DSWMEEVIKLCGRELVRAQIAICGMSTWSSGSETPGTSESATPESGPG<br>SPGPGTSTEPSEGSAPQLYSALANKCCHVGCTKRSLARFC |
| Relaxin2 (insulin C peptide) | 41 | DSWMEEVIKLCGRELVRAQIAICGMSTWSRREAEDLQVGQVELGGGP<br>GAGSLQPLALEGSLQKRQLYSALANKCCHVGCTKRSLARFC |
| Relaxin2 (XT21) | 42 | DSWMEEVIKLCGRELVRAQIAICGMSTWSSGSETPGTSESATPESGPG<br>SPQLYSALANKCCHVGCTKRSLARFC |
| Relaxin2a | 43 | DSWMEEVIKLCGRELVRAQIAICGMSTWSKR |
| Relaxin2b | 44 | RKKRQLYSALANKCCHVGCTKRSLARFC |
| relaxin A chain | 45 | QLYSALANKCCHVGCTKRSLARFC |
| relaxin B chain | 46 | DSWMEEVIKLCGRELVRAQIAICGMSTWS |

TABLE 6-continued

Therapeutic Peptides-Amino Acid Sequence

| Name | SEQ ID NO | Sequence |
|---|---|---|
| Relaxin2 (30GS) | 47 | *DSWMEEVIKLCGRELVRAQIAICGMSTWS*GGGGSGGGGSGGGGSGG GGSGGGGSGGGGS*QLYSALANKCCHVGCTKRSLARFC* |
| Relaxin2 Q60A (30GS) | 48 | *DSWMEEVIKLCGRELVRAQIAICGMSTWS*GGGGSGGGGSGGGGSGG GGSGGGGSGGGG*PALYSALANKCCHVGCTKRSLARFC* |
| Relaxin2 (9GS) | 49 | *DSWMEEVIKLCGRELVRAQIAICGMSTWS*GGGGSGGGGQ*LYSALAN KCCHVGCTKRSLARFC* |
| Relaxin2c (9GS) | 50 | *DSWMEEVIKLCGRELVRAQIAICGMSTWS*GGGGSGGGGQ*LYSALAN KCCHVGCTKRSLARFC* |
| Relaxin2 (GGGPRR) | 51 | *DSWMEEVIKLCGRELVRAQIAICGMSTWS*GGGPRR*QLYSALANKCCH VGCTKRSLARFC* |
| Relaxin2 (18GS) | 52 | *DSWMEEVIKLCGRELVRAQIAICGMSTWS*GGGGSGGGGSGGGGSGG GQ*LYSALANKCCHVGCTKRSLARF* |

For SEQ ID NOs: 37-52
Immunoglobulin Region = dashed underline
Peptide/Therapeutic peptide = italic
Peptide/Therapeutic peptide internal linker = italic
Connecting peptide = bold, thick underline
Linker = double underline
Protease site: underline

TABLE 7

Connecting Peptide Sequences

| Name | SEQ ID NO | Sequence |
|---|---|---|
| (GGGGS)<sub>n</sub> | 53 | GGGGS n = 1-10 |
| (GGGGG)<sub>n</sub> | 54 | GGGGG n = 1-10 |
| CEXa | 55 | NGGPSSGAPPPSGGGGG |
| CEXb | 56 | GGPSSGAPPPSGGGGG |
| EAAAK | 57 | EAAAKEAAAKEAAAK |
| CEXGGGGS | 58 | GGPSSGAPPPSGGGGS |
| XT21 | 59 | SGSETPGTSESATPESGPGSP |
| 16GS | 60 | GGGGSGGGGSGGGGSG |

TABLE 8

Linker Sequences

| Name | SEQ ID NO | Sequence |
|---|---|---|
| Linker a | 61 | GGGGG |
| Linker b | 62 | GGGGS |

TABLE 9

Internal Linker Sequences

| Name | SEQ ID NO | Sequence |
|---|---|---|
| XT100 | 63 | *GTSESATPESGPGSEPATSGSETPGTSESATPESGPGSEPATSGS ETPGTGGGGSHHHHHGGGGSSESATPESGPGTSTEPSEGSAP GSPAGSPTSTEEGTSESATPESGPGSEG* |

TABLE 9-continued

Internal Linker Sequences

| Name | SEQ ID NO | Sequence |
|---|---|---|
| XT35 | 64 | SGSETPGTSESATPESGGGGGSHHHHHGGGGSPGSPGPGTSTEPSEGSAP |
| Insulin C peptide | 65 | RREAEDLQVGQVELGGGPGAGSLQPLALEGSLQKR |
| XT21 | 66 | SGSETPGTSESATPESGPGSP |
| XT35 (noHIS) | 67 | SGSETPGTSESATPESGPGSPGPGTSTEPSEGSAP |
| 30GS | 68 | GGGGSGGGGSGGGGSGGGGSGGGGSGGGGS |
| 9GS | 69 | GGGGSGGGG |
| 18GS | 70 | GGGGSGGGGSGGGGSGGG |
| GGGPRR | 71 | GGGPRR |

TABLE 10

Immunoglobulin Amino Acid Sequences

| NAME | SEQ ID NO | SEQUENCE |
|---|---|---|
| HC CDR1 | 72 | TFSGFSLSTSGMSVG |
| HC CDR2 | 73 | DIWWDDKKDYNPSLKS |
| HC CDR3 original | 74 | SMITNWYFDV |
| HC CDR3 | 75 | SMITX(1)X(2)X(3)FDV; X(1) is F, A, G, or P; X(2) is G, A, S, T, or P; X(3) is G, A, V, L, or P |
| HC CDR3 | 76 | SMITX(1)X(2)X(3)FDV; X(1) is F, A, G, or P; X(2) is W, G, A, S, T, or P; X(3) is Y, G, A, V, L, or P |
| HC CDR3 | 77 | SMITX(1)X(2)X(3)FDV; X(1) is N, F, A, G, or P; X(2) is G, A, S, T, or P; X(3) is Y, G, A, V, L, or P |
| HC CDR3 | 78 | SMITX(1)X(2)X(3)FDV; X(1) is N, F, A, G, or P; X(2) is W, G, A, S, T, or P; X(3) is G, A, V, L, or P |
| HC CDR3 | 79 | SMITFGGFDV |
| HC CDR3 | 80 | SMITNAYFDV |
| HC CDR3 | 81 | SMITNGYFDV |
| HC CDR3 | 82 | SMITFWYFDV |
| HC CDR3 | 83 | SMITFGYFDV |
| HC CDR3 | 84 | SMITFAYFDV |
| HC CDR3 | 85 | SMITFAGFDV |
| HC CDR3 | 86 | SMITNGGFDV |
| HC CDR3 | 87 | SMITNAGFDV |
| HC CDR3 | 88 | SMITNWGFDV |
| LC CDR1 | 89 | KCQLSVGYMH |
| LC CDR2 | 90 | DTSKLAS |
| LC CDR3 (original) | 91 | FQGSGYPFT |
| LC CDR3 | 92 | FQX(4)X(5)GYPFT; X(4) is G, Y, F, W, P, L, V, or A; X(5) is S, N, G, A, V, L, or P |

TABLE 10-continued

Immunoglobulin Amino Acid Sequences

| NAME | SEQ ID NO | SEQUENCE |
| --- | --- | --- |
| LC CDR3 | 93 | FQX(4)X(5)GYPFT; X(4) is Y, F, W, P, L, V, or A; X(5) is S, N, G, A, V, L, or P |
| LC CDR3 | 94 | FQX(4)X(5)GYPFT; X(4) is G, Y, F, W, P, L, V, or A; X(5) is N, G, A, V, L, or P |
| LC CDR3 | 95 | FQYSGYPFT |
| LC CDR3 | 96 | FQGNGYPFT |
| LC CDR3 | 97 | FQYNGYPFT |
| HC $F_C$ | 98 | DKTHTCPPCPAPPVAGPSVFLFPPKPKDTLMISRTPE VTCVVVDVSHEDPEVKFNWYVDGVEVHNAKTKPR EEQYNSTYRVVSVLTVLHQDWLNGKEYKCKVSNK GLPSSIEKTISKAKGQPREPQVYTLPPSRDELTKNQV SLTCLVKGFYPSDIAVEWESNGQPENNYKTTPPVLD SDGSFFLYSKLTVDKSRWQQGNVFSCSVMHEALH NHYTQKSLSLSPGK |

What is claimed is:

1. An immunoglobulin fusion protein comprising a therapeutic peptide inserted into a light chain complementarity determining region 3 (CDR3) of an antibody variable region comprising: a heavy chain comprising a CDR1 of SEQ ID NO: 72, a CDR2 of SEQ ID NO: 73, and a CDR3 sequence selected from SEQ ID NOS: 75-78; and a light chain comprising a CDR1 of SEQ ID NO: 89, a CDR2 of SEQ ID NO: 90, and a CDR3 sequence comprising at least three contiguous amino acids of SEQ ID NO: 91.

2. The immunoglobulin fusion protein of claim 1, comprising SEQ ID NO: 75: SMITX(1)X(2)X(3)FDV; wherein X(1) is F, A, G, or P; X(2) is G, A, S, T, or P; and X(3) is G, A, V, L, or P.

3. The immunoglobulin fusion protein of claim 2, wherein X(1) is F.

4. The immunoglobulin fusion protein of claim 2, wherein X(2) is G.

5. The immunoglobulin fusion protein of claim 2, wherein X(3) is G.

6. The immunoglobulin fusion protein of claim 1, wherein the sequence selected from SEQ ID NOS: 75-78 comprises a sequence selected from SEQ ID NOS: 79-88.

7. The immunoglobulin fusion protein of claim 6, comprising the SEQ ID NO: 79.

8. A method comprising administering to a subject in need thereof the immunoglobulin fusion protein of claim 1.

9. An antibody comprising the immunoglobulin fusion protein of claim 1 and a Fc domain at least 90% homologous to SEQ ID NO: 98.

10. The antibody of claim 9, comprising SEQ ID NO: 16.

11. An antibody comprising a Fc region having SEQ ID NO: 98, and an antibody variable region comprising a heavy chain comprising a sequence at least about 95% identical to SEQ ID NO: 16, and a light chain comprising a therapeutic peptide and a sequence at least about 95% identical to SEQ ID NO: 9.

12. The antibody of claim 11, wherein the therapeutic peptide is positioned within the antibody variable region.

13. The antibody of claim 11, wherein the therapeutic peptide is inserted into the antibody variable region.

* * * * *

SEQUENCE LISTING

<160> NUMBER OF SEQ ID NOS: 99

<210> SEQ ID NO 1
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gacatccaga tgacccagtc cccctccacc ctgtccgcct ccgtgggcga ccgcgtgacc      60
atcacctgca agtgccagct gtccgtgggc tacatgcact ggtaccagca gaagcccggc     120
aaggccccca agctgctgat ctacgacacc tccaagctgg cctccggcgt gccctcccgc     180
ttctccggct ccggctccgg caccgagttc accctgacca tctcctccct gcagcccgac     240
gacttcgcca cctactactg cttccagggc tccggctacc ccttcacctt cggcggcggc     300
accaagctgg agatcaaacg aactgtggct gcaccatctg tcttcatctt cccgccatct     360
gatgagcagt tgaaatctgg aactgcctct gtcgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
tcctcgcccg tcacaaagag cttcaacagg ggagagtgt                            639
```

<210> SEQ ID NO 2
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gacatccaga tgacccagtc cccctccacc ctgtccgcct ccgtgggcga ccgcgtgacc      60
atcacctgca agtgccagct gtccgtgggc tacatgcact ggtaccagca gaagcccggc     120
```

```
aaggcccca agctgctgat ctacgacacc tccaagctgg cctccggcgt gccctcccgc    180
ttctccggct ccggctccgg caccgccttc accctgacca tctcctccct gcagcccgac    240
gacttcgcca cctactactg cttccagggc tccggctacc ccttcacctt cggcggcggc    300
accaagctgg agatcaaacg aactgtggct gcaccatctg tcttcatctt cccgccatct    360
gatgagcagt tgaaatctgg aactgcctct gtcgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
tcctcgcccg tcacaaagag cttcaacagg ggagagtgt                          639
```

<210> SEQ ID NO 3
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gacatccaga tgacccagtc cccctccacc ctgtccgcct ccgtgggcga ccgcgtgacc     60
atcacctgca gtgccagct gtccgtgggc tacatgcact ggtaccagca gaagcccggc    120 aaggcccca agctgctgat ctacgacacc tccaagctgg cctccggcgt gccctcccgc    180
ttctccggct ccggctccgg caccgccttc accctgacca tctcctccct gcagcccgac    240
gacttcgcca cctactactg cttccagtac tccggctacc ccttcacctt cggcggcggc    300
accaagctgg agatcaaacg aactgtggct gcaccatctg tcttcatctt cccgccatct    360
gatgagcagt tgaaatctgg aactgcctct gtcgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
tcctcgcccg tcacaaagag cttcaacagg ggagagtgt                          639
```

<210> SEQ ID NO 4
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gacatccaga tgacccagtc cccctccacc ctgtccgcct ccgtgggcga ccgcgtgacc     60
atcacctgca gtgccagct gtccgtgggc tacatgcact ggtaccagca gaagcccggc    120 aaggcccca agctgctgat ctacgacacc tccaagctgg cctccggcgt gccctcccgc    180
ttctccggct ccggctccgg caccgccttc accctgacca tctcctccct gcagcccgac    240
gacttcgcca cctactactg cttccagggc aacggctacc ccttcacctt cggcggcggc    300
accaagctgg agatcaaacg aactgtggct gcaccatctg tcttcatctt cccgccatct    360
gatgagcagt tgaaatctgg aactgcctct gtcgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
```

```
agcaaagcag actacgagaa acacaaagtc tacgcctgcg aagtcaccca tcagggcctg    600
tcctcgcccg tcacaaagag cttcaacagg ggagagtgt                          639
```

<210> SEQ ID NO 5
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
caggtgaccc tgcgcgagtc cggccctgca ctggtgaagc ccacccagac cctgaccctg    60
acctgcacct ctccggcttc tccctgtcc acctccggca tgtccgtggg ctggatccgg    120
cagcctcccg gcaaggccct ggagtggctg gctgacatct ggtgggacga caagaaggac    180
tacaacccct ccctgaagtc ccgcctgacc atctccaagg acacctccaa gaaccaggtg    240
gtgctgaagg tgaccaacat ggaccccgcc gacaccgcca cctactactg cgcccgctca    300
atgattacca actggtactt cgacgtgtgg ggagccggta ccaccgtgac cgtgtcttcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgact gtgccctcta gcagcttggg cacccagacc    600
tacatctgca acgtgaatca caagcccagc aacaccaagg tggacaagaa agttgaaccc    660
aaatcttgcg acaaaactca cacatgccca ccgtgcccag cacctccagt cgccggaccg    720
tcagtcttcc tcttccctcc aaaacccaag gacaccctca tgatctcccg gaccctgag    780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaaggcctc ccagctccca tcgagaaaac catctccaaa    1020
gccaaagggc agccccgaga accacaggtg tacaccctgc ctccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga taa                                1353
```

<210> SEQ ID NO 6
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
caggtgaccc tgcgcgagtc cggccctgca ctggtgaagc ccacccagac cctgaccctg    60
acctgcacct ctccggcttc tccctgtcc acctccggca tgtccgtggg ctggatccgg    120
cagcctcccg gcaaggccct ggagtggctg gctgacatct ggtgggacga caagaaggac    180
```

| | |
|---|---|
| tacaacccct ccctgaagtc ccgcctgacc atctccaagg acacctccaa gaaccaggtg | 240 |
| gtgctgaagg tgaccaacat ggaccccgcc gacaccgcca cctactactg cgcccgctca | 300 |
| atgattacca acgcctactt cgacgtgtgg ggagccggta ccaccgtgac cgtgtcttcc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctccagt cgccggaccg | 720 |
| tcagtcttcc tcttccctcc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaaggcctc ccaagctcca tcgagaaaac catctccaaa | 1020 |
| gccaaagggc agccccgaga accacaggtg tacaccctgc ctccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatga taa | 1353 |

<210> SEQ ID NO 7
<211> LENGTH: 1353
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 7

| | |
|---|---|
| caggtgaccc tgcgcgagtc cggccctgca ctggtgaagc ccacccagac cctgaccctg | 60 |
| acctgcacct tctccggctt ctccctgtcc acctccggca tgtccgtggg ctggatccgg | 120 |
| cagcctcccg gcaaggccct ggagtggctg gctgacatct ggtgggacga caagaaggac | 180 |
| tacaacccct ccctgaagtc ccgcctgacc atctccaagg acacctccaa gaaccaggtg | 240 |
| gtgctgaagg tgaccaacat ggaccccgcc gacaccgcca cctactactg cgcccgctca | 300 |
| atgattacca acgcctactt cgacgtgtgg ggagccggta ccaccgtgac cgtgtcttcc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctccagt cgccggaccg | 720 |
| tcagtcttcc tcttccctcc aaaacccaag gacaccctca tgatctcccg gacccctgag | 780 |
| gtcacatgcg tggtggtgga cgtgagccac gaagaccctg aggtcaagtt caactggtac | 840 |

| | |
|---|---|
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaaggcctc ccaagctcca tcgagaaaac catctccaaa | 1020 |
| gccaaagggc agccccgaga accacaggtg tacaccctgc ctccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatga taa | 1353 |

<210> SEQ ID NO 8
<211> LENGTH: 1353
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 8

| | |
|---|---|
| caggtgaccc tgcgcgagtc cggccctgca ctggtgaagc ccacccagac cctgaccctg | 60 |
| acctgcacct tctccggctt ctccctgtcc acctccggca tgtccgtggg ctggatccgg | 120 |
| cagcctcccg gcaaggccct ggagtggctg gctgacatct ggtgggacga caagaaggac | 180 |
| tacaacccct ccctgaagtc ccgcctgacc atctccaagg acacctccaa gaaccaggtg | 240 |
| gtgctgaagg tgaccaacat ggaccccgcc gacaccgcca cctactactg cgcccgctca | 300 |
| atgattacct cgggggcttc gacgtgtgg ggagccggta ccaccgtgac cgtgtcttcc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgact gtgccctcta gcagcttggg cacccagacc | 600 |
| tacatctgca acgtgaatca caagcccagc aacaccaagg tggacaagaa agttgaaccc | 660 |
| aaatcttgcg acaaaactca cacatgccca ccgtgcccag cacctccagt cgccggaccg | 720 |
| tcagtcttcc tcttccctcc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaaggcctc ccaagctcca tcgagaaaac catctccaaa | 1020 |
| gccaaagggc agccccgaga accacaggtg tacaccctgc ctccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatga taa | 1353 |

<210> SEQ ID NO 9
<211> LENGTH: 213
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 10
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
```

100                 105                 110
Ser Val Phe Ile Phe Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 11
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Tyr Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 12
<211> LENGTH: 213

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Asn Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 13
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95
```

```
Cys Ala Arg Ser Met Ile Thr Asn Trp Tyr Phe Asp Val Trp Gly Ala
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

-continued

```
Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Asp Lys Lys Asp Tyr Asn Pro Ser
    50                  55                  60
Leu Lys Ser Arg Leu Thr Ile Ser Lys Asp Thr Ser Lys Asn Gln Val
65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Ala Tyr Phe Asp Val Trp Gly Ala
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Pro Val Ala Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
```

```
                        420                 425                 430

Ala Leu His Asn His Tyr Thr Gln Lys Ser Leu Ser Leu Ser Pro Gly
            435                 440                 445

Lys

<210> SEQ ID NO 15
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Gly Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
```

```
                    325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 16
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
                20                  25                  30
Gly Met Ser Val Gly Trp Ile Arg Gln Pro Pro Gly Lys Ala Leu Glu
                35                  40                  45
Trp Leu Ala Asp Ile Trp Trp Asp Asp Lys Lys Asp Tyr Asn Pro Ser
            50                  55                  60
Leu Lys Ser Arg Leu Thr Ile Ser Lys Asp Thr Ser Lys Asn Gln Val
65              70                  75                  80
Val Leu Lys Val Thr Asn Met Asp Pro Ala Asp Thr Ala Thr Tyr Tyr
                85                  90                  95
Cys Ala Arg Ser Met Ile Thr Phe Gly Gly Phe Asp Val Trp Gly Ala
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Pro Val Ala Gly Pro
```

```
              225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 17
<211> LENGTH: 1587
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gactcttgga tggaagaagt tatcaaactg tgcggtcgtg aactggttcg tgctcagatc      60
gctatctgcg gtatgtctac ctggtctggc gggggtggga gcggggagg cggacagctg     120 tactctgctc tggctaacaa atgctgccac gttggttgca ccaaacgttc tctggctcgt    180
ttctgcggcg gaggcggatc cggaggcgga ggttccggcg ggggtgggag cgggcaggtg    240
accctgcgcg agtccggccc tgcactggtg aagcccaccc agaccctgac cctgacctgc    300
accttctccg gcttctccct gtccaccctc ggcatgtccg tgggctggat ccggcagcct    360
cccggcaagg ccctggagtg gctggctgac atctggtggg acgacaagaa ggactacaac    420
ccctccctga gtcccgcct gaccatctcc aaggacacct ccaagaacca ggtggtgctg    480
aaggtgacca catggacccc cgccgacacc gccacctact actgcgcccg ctcaatgatt    540
accaacgcct acttcgacgt gtggggagcc ggtaccaccg tgaccgtgtc ttccgcctcc    600
accaagggcc catcggtctt ccccctggca ccctcctcca agagcacctc tgggggcaca    660
gcggccctgg gctgcctggt caaggactac ttccccgaac cggtgacggt gtcgtggaac    720
tcaggcgccc tgaccagcgg cgtgcacacc ttcccggctg tcctacagtc ctcaggactc    780
```

```
tactccctca gcagcgtggt gactgtgccc tctagcagct tgggcaccca gacctacatc      840
tgcaacgtga atcacaagcc cagcaacacc aaggtggaca agaaagttga acccaaatct      900
tgcgacaaaa ctcacacatg cccaccgtgc ccagcacctc cagtcgccgg accgtcagtc      960
ttcctcttcc ctccaaaacc caaggacacc ctcatgatct cccggacccc tgaggtcaca     1020
tgcgtggtgg tggacgtgag ccacgaagac cctgaggtca agttcaactg gtacgtggac     1080
ggcgtggagg tgcataatgc caagacaaag ccgcgggagg agcagtacaa cagcacgtac     1140
cgtgtggtca gcgtcctcac cgtcctgcac caggactggc tgaatggcaa ggagtacaag     1200
tgcaaggtct ccaacaaagg cctcccaagc tccatcgaga aaaccatctc caaagccaaa     1260
gggcagcccc gagaaccaca ggtgtacacc ctgcctccat cccgggatga gctgaccaag     1320
aaccaggtca gcctgacctg cctggtcaaa ggcttctatc ccagcgacat cgccgtggag     1380
tgggagagca atgggcagcc ggagaacaac tacaagacca cgcctcccgt gctggactcc     1440
gacggctcct tcttcctcta cagcaagctc accgtggaca agagcaggtg gcagcagggg     1500
aacgtcttct catgctccgt gatgcatgag gctctgcaca accactacac gcagaagagc     1560
ctctccctgt ctccgggtaa atgataa                                         1587
```

<210> SEQ ID NO 18
<211> LENGTH: 1587
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gactcttgga tggaagaagt tatcaaactg tgcggtcgtg aactggttcg tgctcagatc       60
gctatctgcg gtatgtctac ctggtctggc gggggtggga gcgggggagg cggacagctg      120
tactctgctc tggctaacaa atgctgccac gttggttgca ccaaacgttc tctggctcgt      180
ttctgcggcg gaggcggatc cggaggcgga ggttccggcg ggggtgggag cggcaggtg      240 accctgcgcg agtccggccc tgcactggtg aagcccaccc agaccctgac cctgacctgc      300
accttctccg gcttctccct gtccaccctcc ggcatgtccg tgggctggat ccggcagcct      360
cccggcaagg ccctggagtg gctggctgac atctggtggg acgacaagaa ggactacaac      420
ccctccctga agtcccgcct gaccatctcc aaggacacct ccaagaacca ggtggtgctg      480
aaggtgacca acatggaccc cgccgacacc gccacctact actgcgcccg ctcaatgatt      540
accaacggct acttcgacgt gtggggagcc ggtaccaccg tgaccgtgtc ttccgcctcc      600
accaagggcc catcggtctt ccccctggca ccctcctcca agagcacctc tgggggcaca      660
gcggccctgg gctgcctggt caaggactac ttccccgaac cggtgacggt gtcgtggaac      720
tcaggcgccc tgaccagcgg cgtgcacacc ttcccggctg tcctacagtc ctcaggactc      780
tactccctca gcagcgtggt gactgtgccc tctagcagct tgggcaccca gacctacatc      840
tgcaacgtga atcacaagcc cagcaacacc aaggtggaca agaaagttga acccaaatct      900
tgcgacaaaa ctcacacatg cccaccgtgc ccagcacctc cagtcgccgg accgtcagtc      960
ttcctcttcc ctccaaaacc caaggacacc ctcatgatct cccggacccc tgaggtcaca     1020
tgcgtggtgg tggacgtgag ccacgaagac cctgaggtca agttcaactg gtacgtggac     1080
ggcgtggagg tgcataatgc caagacaaag ccgcgggagg agcagtacaa cagcacgtac     1140
cgtgtggtca gcgtcctcac cgtcctgcac caggactggc tgaatggcaa ggagtacaag     1200
```

-continued

```
tgcaaggtct ccaacaaagg cctcccaagc tccatcgaga aaaccatctc caaagccaaa    1260
gggcagcccc gagaaccaca ggtgtacacc ctgcctccat cccgggatga gctgaccaag    1320
aaccaggtca gcctgacctg cctggtcaaa ggcttctatc ccagcgacat cgccgtggag    1380
tgggagagca atgggcagcc ggagaacaac tacaagacca cgcctcccgt gctggactcc    1440
gacggctcct tcttcctcta cagcaagctc accgtggaca agagcaggtg gcagcagggg    1500
aacgtcttct catgctccgt gatgcatgag gctctgcaca accactacac gcagaagagc    1560
ctctccctgt ctccgggtaa atgataa                                       1587
```

<210> SEQ ID NO 19
<211> LENGTH: 1587
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gactcttgga tggaagaagt tatcaaactg tgcggtcgtg aactggttcg tgctcagatc      60
gctatctgcg gtatgtctac ctggtctggc ggggtgggga gcggggggagg cggacagctg    120 tactctgctc tggctaacaa atgctgccac gttggttgca ccaaacgttc tctggctcgt    180
ttctgcggcg gaggcggatc cggaggcgga ggttccggcg ggggtgggag cgggcaggtg    240
accctgcgcg agtccggccc tgcactggtg aagcccaccc agaccctgac cctgacctgc    300
accttctccg gcttctccct gtccacctcc ggcatgtccg tgggctggat ccggcagcct    360
cccggcaagg ccctggagtg gctggctgac atctggtggg acgacaagaa ggactacaac    420 ccctcctga gtcccgcct gaccatctcc aaggacacct ccaagaacca ggtggtgctg    480
aaggtgacca acatggaccc cgccgacacc gccacctact actgcgcccg ctcaatgatt    540
accttcgggg gcttcgacgt gtggggagcc ggtaccaccg tgaccgtgtc ttccgcctcc    600
accaagggcc catcggtctt ccccctggca ccctcctcca agagcacctc tgggggcaca    660
gcggccctgg gctgcctggt caaggactac ttccccgaac cggtgacggt gtcgtggaac    720
tcaggcgccc tgaccagcgg cgtgcacacc ttcccggctg tcctacagtc ctcaggactc    780
tactccctca gcagcgtggt gactgtgccc tctagcagct tgggcaccca gacctacatc    840
tgcaacgtga atcacaagcc cagcaacacc aaggtggaca agaaagttga acccaaatct    900
tgcgacaaaa ctcacacatg cccaccgtgc ccagcacctc cagtcgccgg accgtcagtc    960
ttcctcttcc ctccaaaacc caaggacacc ctcatgatct cccggacccc tgaggtcaca   1020
tgcgtggtgg tggacgtgag ccacgaagac cctgaggtca agttcaactg gtacgtggac   1080
ggcgtggagg tgcataatgc caagacaaag ccgcgggagg agcagtacaa cagcacgtac   1140
cgtgtggtca gcgtcctcac cgtcctgcac caggactggc tgaatggcaa ggagtacaag   1200
tgcaaggtct ccaacaaagg cctcccaagc tccatcgaga aaaccatctc caaagccaaa   1260
gggcagcccc gagaaccaca ggtgtacacc ctgcctccat cccgggatga gctgaccaag   1320
aaccaggtca gcctgacctg cctggtcaaa ggcttctatc ccagcgacat cgccgtggag   1380
tgggagagca atgggcagcc ggagaacaac tacaagacca cgcctcccgt gctggactcc   1440
gacggctcct tcttcctcta cagcaagctc accgtggaca agagcaggtg gcagcagggg   1500
aacgtcttct catgctccgt gatgcatgag gctctgcaca accactacac gcagaagagc   1560
ctctccctgt ctccgggtaa atgataa                                      1587
```

<210> SEQ ID NO 20
<211> LENGTH: 527
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Gly Gly
    50                  55                  60

Gly Gly Ser Gly Gly Gly Ser Gly Gly Gly Ser Gly Gln Val
65                  70                  75                  80

Thr Leu Arg Glu Ser Gly Pro Ala Leu Val Lys Pro Thr Gln Thr Leu
                85                  90                  95

Thr Leu Thr Cys Thr Phe Ser Gly Phe Ser Leu Ser Thr Ser Gly Met
            100                 105                 110

Ser Val Gly Trp Ile Arg Gln Pro Pro Gly Lys Ala Leu Glu Trp Leu
        115                 120                 125

Ala Asp Ile Trp Trp Asp Asp Lys Lys Asp Tyr Asn Pro Ser Leu Lys
    130                 135                 140

Ser Arg Leu Thr Ile Ser Lys Asp Thr Ser Lys Asn Gln Val Val Leu
145                 150                 155                 160

Lys Val Thr Asn Met Asp Pro Ala Asp Thr Ala Thr Tyr Tyr Cys Ala
                165                 170                 175

Arg Ser Met Ile Thr Asn Ala Tyr Phe Asp Val Trp Gly Ala Gly Thr
            180                 185                 190

Thr Val Thr Val Ser Ser Ala Ser Thr Lys Gly Pro Ser Val Phe Pro
        195                 200                 205

Leu Ala Pro Ser Ser Lys Ser Thr Ser Gly Gly Thr Ala Ala Leu Gly
    210                 215                 220

Cys Leu Val Lys Asp Tyr Phe Pro Glu Pro Val Thr Val Ser Trp Asn
225                 230                 235                 240

Ser Gly Ala Leu Thr Ser Gly Val His Thr Phe Pro Ala Val Leu Gln
                245                 250                 255

Ser Ser Gly Leu Tyr Ser Leu Ser Ser Val Val Thr Val Pro Ser Ser
            260                 265                 270

Ser Leu Gly Thr Gln Thr Tyr Ile Cys Asn Val Asn His Lys Pro Ser
        275                 280                 285

Asn Thr Lys Val Asp Lys Lys Val Glu Pro Lys Ser Cys Asp Lys Thr
    290                 295                 300

His Thr Cys Pro Pro Cys Pro Ala Pro Pro Val Ala Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
```

```
              355                 360                 365
Thr Lys Pro Arg Glu Glu Gln Tyr Asn Ser Thr Tyr Arg Val Val Ser
370                 375                 380

Val Leu Thr Val Leu His Gln Asp Trp Leu Asn Gly Lys Glu Tyr Lys
385                 390                 395                 400

Cys Lys Val Ser Asn Lys Gly Leu Pro Ser Ile Glu Lys Thr Ile
                405                 410                 415

Ser Lys Ala Lys Gly Gln Pro Arg Glu Pro Gln Val Tyr Thr Leu Pro
                420                 425                 430

Pro Ser Arg Asp Glu Leu Thr Lys Asn Gln Val Ser Leu Thr Cys Leu
                435                 440                 445

Val Lys Gly Phe Tyr Pro Ser Asp Ile Ala Val Glu Trp Glu Ser Asn
        450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
                500                 505                 510

His Asn His Tyr Thr Gln Lys Ser Leu Ser Leu Ser Pro Gly Lys
        515                 520                 525

<210> SEQ ID NO 21
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly
                20                  25                  30

Gly Ser Gly Gly Gly Gly Gln Leu Tyr Ser Ala Leu Ala Asn Lys Cys
            35                  40                  45

Cys His Val Gly Cys Thr Lys Arg Ser Leu Ala Arg Phe Cys Gly Gly
        50                  55                  60

Gly Gly Ser Gly Gly Gly Gly Ser Gly Gly Gly Gly Ser Gly Gln Val
65                  70                  75                  80

Thr Leu Arg Glu Ser Gly Pro Ala Leu Val Lys Pro Thr Gln Thr Leu
                85                  90                  95

Thr Leu Thr Cys Thr Phe Ser Gly Phe Ser Leu Ser Thr Ser Gly Met
                100                 105                 110

Ser Val Gly Trp Ile Arg Gln Pro Pro Gly Lys Ala Leu Glu Trp Leu
            115                 120                 125

Ala Asp Ile Trp Trp Asp Asp Lys Lys Asp Tyr Asn Pro Ser Leu Lys
        130                 135                 140

Ser Arg Leu Thr Ile Ser Lys Asp Thr Ser Lys Asn Gln Val Val Leu
145                 150                 155                 160

Lys Val Thr Asn Met Asp Pro Ala Asp Thr Ala Thr Tyr Tyr Cys Ala
                165                 170                 175

Arg Ser Met Ile Thr Asn Gly Tyr Phe Asp Val Trp Gly Ala Gly Thr
                180                 185                 190
```

```
Thr Val Thr Val Ser Ser Ala Ser Thr Lys Gly Pro Ser Val Phe Pro
            195                 200                 205

Leu Ala Pro Ser Ser Lys Ser Thr Ser Gly Gly Thr Ala Ala Leu Gly
210                 215                 220

Cys Leu Val Lys Asp Tyr Phe Pro Glu Pro Val Thr Val Ser Trp Asn
225                 230                 235                 240

Ser Gly Ala Leu Thr Ser Gly Val His Thr Phe Pro Ala Val Leu Gln
            245                 250                 255

Ser Ser Gly Leu Tyr Ser Leu Ser Ser Val Val Thr Val Pro Ser Ser
            260                 265                 270

Ser Leu Gly Thr Gln Thr Tyr Ile Cys Asn Val Asn His Lys Pro Ser
            275                 280                 285

Asn Thr Lys Val Asp Lys Lys Val Glu Pro Lys Ser Cys Asp Lys Thr
290                 295                 300

His Thr Cys Pro Pro Cys Pro Ala Pro Pro Val Ala Gly Pro Ser Val
305                 310                 315                 320

Phe Leu Phe Pro Pro Lys Pro Lys Asp Thr Leu Met Ile Ser Arg Thr
            325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
            355                 360                 365

Thr Lys Pro Arg Glu Glu Gln Tyr Asn Ser Thr Tyr Arg Val Val Ser
370                 375                 380

Val Leu Thr Val Leu His Gln Asp Trp Leu Asn Gly Lys Glu Tyr Lys
385                 390                 395                 400

Cys Lys Val Ser Asn Lys Gly Leu Pro Ser Ser Ile Glu Lys Thr Ile
            405                 410                 415

Ser Lys Ala Lys Gly Gln Pro Arg Glu Pro Gln Val Tyr Thr Leu Pro
            420                 425                 430

Pro Ser Arg Asp Glu Leu Thr Lys Asn Gln Val Ser Leu Thr Cys Leu
            435                 440                 445

Val Lys Gly Phe Tyr Pro Ser Asp Ile Ala Val Glu Trp Glu Ser Asn
450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
            485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly Lys
            515                 520                 525

<210> SEQ ID NO 22
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30
```

```
Gly Ser Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Gly Gly
    50                  55                  60

Gly Gly Ser Gly Gly Gly Ser Gly Gly Gly Ser Gly Gln Val
65                  70                  75                  80

Thr Leu Arg Glu Ser Gly Pro Ala Leu Val Lys Pro Thr Gln Thr Leu
                85                  90                  95

Thr Leu Thr Cys Thr Phe Ser Gly Phe Ser Leu Ser Thr Ser Gly Met
            100                 105                 110

Ser Val Gly Trp Ile Arg Gln Pro Pro Gly Lys Ala Leu Glu Trp Leu
        115                 120                 125

Ala Asp Ile Trp Trp Asp Asp Lys Asp Tyr Asn Pro Ser Leu Lys
    130                 135                 140

Ser Arg Leu Thr Ile Ser Lys Asp Thr Ser Lys Asn Gln Val Val Leu
145                 150                 155                 160

Lys Val Thr Asn Met Asp Pro Ala Asp Thr Ala Thr Tyr Tyr Cys Ala
                165                 170                 175

Arg Ser Met Ile Thr Phe Gly Gly Phe Asp Val Trp Gly Ala Gly Thr
            180                 185                 190

Thr Val Thr Val Ser Ser Ala Ser Thr Lys Gly Pro Ser Val Phe Pro
        195                 200                 205

Leu Ala Pro Ser Ser Lys Ser Thr Ser Gly Gly Thr Ala Ala Leu Gly
    210                 215                 220

Cys Leu Val Lys Asp Tyr Phe Pro Glu Pro Val Thr Val Ser Trp Asn
225                 230                 235                 240

Ser Gly Ala Leu Thr Ser Gly Val His Thr Phe Pro Ala Val Leu Gln
                245                 250                 255

Ser Ser Gly Leu Tyr Ser Leu Ser Ser Val Val Thr Val Pro Ser Ser
            260                 265                 270

Ser Leu Gly Thr Gln Thr Tyr Ile Cys Asn Val Asn His Lys Pro Ser
        275                 280                 285

Asn Thr Lys Val Asp Lys Lys Val Glu Pro Lys Ser Cys Asp Lys Thr
    290                 295                 300

His Thr Cys Pro Pro Cys Pro Ala Pro Pro Val Ala Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Gly Leu Pro Ser Ser Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Asp Glu Leu Thr Lys Asn Gln Val Ser Leu Thr Cys Leu
        435                 440                 445
```

```
Val Lys Gly Phe Tyr Pro Ser Asp Ile Ala Val Glu Trp Glu Ser Asn
    450                 455                 460
Gly Gln Pro Glu Asn Asn Tyr Lys Thr Thr Pro Pro Val Leu Asp Ser
465                 470                 475                 480
Asp Gly Ser Phe Phe Leu Tyr Ser Lys Leu Thr Val Asp Lys Ser Arg
                485                 490                 495
Trp Gln Gln Gly Asn Val Phe Ser Cys Ser Val Met His Glu Ala Leu
            500                 505                 510
His Asn His Tyr Thr Gln Lys Ser Leu Ser Leu Ser Pro Gly Lys
        515                 520                 525
```

<210> SEQ ID NO 23
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gactcttgga tggaagaagt tatcaaactg tgcggtcgtg aactggttcg tgctcagatc    60
gctatctgcg gtatgtctac ctggtctaaa cgttctctgt ctcaggaaga cgctccgcag   120
accccgcgtc cggttgctga atcgttccg tctttcatca acaaagacac cgaaaccatc   180
aacatgatgt ctgaattcgt tgctaacctg ccgcaggaac tgaaactgac cctgtctgaa   240
atgcagccgg ctctgccgca gctgcagcag cacgttccgg ttctgaaaga ctcttctctg   300
ctgttcgaag aattcaaaaa actgatccgt aaccgtcagt ctgaagctgc tgactcttct   360
ccgtctgaac tgaaatacct gggtctggac acccactctc gtaaaaaacg tcagctgtac   420
tctgctctgg ctaacaaatg ctgccacgtt ggttgcacca acgttctct ggctcgtttc   480
tgc                                                                483
```

<210> SEQ ID NO 24
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gactcttgga tggaagaagt tatcaaactg tgcggtcgtg aactggttcg tgctcagatc    60
gctatctgcg gtatgtctac ctggtctaaa cgtggaggtg gcgggagcgg cacttctgag   120
tctgctactc cagaaagcgg cccaggttct gaaccagcaa cttctggctc tgagactcca   180
ggcacttctg agtccgcaac gcctgaatcc ggtcctggtt ctgaaccagc tacttccggc   240
agcgaaaccc caggtaccgg aggtggcggg agccaccatc accaccacca cggaggtggc   300
gggagctctg agtctgcgac tccagagtct ggtcctggta cttccactga gcctagcgag   360
ggttccgcac aggttctcc ggctggtagc ccgaccagca cggaggaggg tacgtctgaa   420
tctgcaacgc cggaatcggg cccaggttcg gaggggaggag gtggcgggag ccgtaaaaaa   480
cgtcagctgt actctgctct ggctaacaaa tgctgccacg ttggttgcac caaacgttct   540
ctggctcgtt tctgc                                                   555
```

<210> SEQ ID NO 25
<211> LENGTH: 360
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 25

```
gactcttgga tggaagaagt tatcaaactg tgcggtcgtg aactggttcg tgctcagatc    60
gctatctgcg gtatgtctac ctggtctaaa cgtggaggtg gcgggagctc tggcagcgaa   120
accccgggta cctccgaatc tgctacaccg gaaagcggtg gaggtggcgg gagccaccat   180
caccaccacc acggaggtgg cgggagccct ggcagccctg gtccgggcac tagcaccgag   240
ccatcggagg gctccgcacc aggaggtggc gggagccgta aaaaacgtca gctgtactct   300
gctctggcta acaaatgctg ccacgttggt tgcaccaaac gttctctggc tcgtttctgc   360
```

<210> SEQ ID NO 26
<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
gactcttgga tggaagaagt tatcaaactg tgcggtcgtg aactggttcg tgctcagatc    60
gctatctgcg gtatgtctac ctggtcttct ggcagcgaaa ccccgggtac ctccgaatct   120
gctacaccgg aaagcggtcc tggcagccct ggtccgggca ctagcaccga gccatcggag   180
ggctccgcac cacagctgta ctctgctctg gctaacaaat gctgccacgt tggttgcacc   240
aaacgttctc tggctcgttt ctgc                                          264
```

<210> SEQ ID NO 27
<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gactcttgga tggaagaagt tatcaaactg tgcggtcgtg aactggttcg tgctcagatc    60
gctatctgcg gtatgtctac ctggtctcgt cgtgaagctc aagacctgca ggttggtcag   120
gttgaactgg gtggtggtcc gggtgctggt tctctgcagc cgctggctct ggaaggttct   180
ctgcagaaac gtcagctgta ctctgctctg gctaacaaat gctgccacgt tggttgcacc   240
aaacgttctc tggctcgttt ctgc                                          264
```

<210> SEQ ID NO 28
<211> LENGTH: 222
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gactcttgga tggaagaagt tatcaaactg tgcggtcgtg aactggttcg tgctcagatc    60
gctatctgcg gtatgtctac ctggtcttct ggcagcgaaa ccccgggtac ctccgaatct   120
gctacaccgg aaagcggtcc tggcagccct cagctgtact ctgctctggc taacaaatgc   180
tgccacgttg gttgcaccaa acgttctctg gctcgtttct gc                      222
```

<210> SEQ ID NO 29
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gactcttgga tggaagaagt tatcaaactg tgcggtcgtg aactggttcg tgctcagatc    60
gctatctgcg gtatgtctac ctggtctaaa cgt                                 93

<210> SEQ ID NO 30
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cgtaaaaaac gtcagctgta ctctgctctg gctaacaaat gctgccacgt tggttgcacc    60
aaacgttctc tggctcgttt ctgc                                           84

<210> SEQ ID NO 31
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gactcttgga tggaagaagt tatcaaactg tgcggtcgtg aactggttcg tgctcagatc    60
gctatctgcg gtatgtctac ctggtctggc gggggaggca gcgggggagg cgggtccgga   120
ggcgggggat ctggcggggg aggcagtggg ggaggcggga gcggaggcgg ggctctcag    180 ctgtactctg ctctggctaa caaatgctgc cacgttggtt gcaccaaacg ttctctggct   240
cgtttctgc                                                           249

<210> SEQ ID NO 32
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gactcttgga tggaagaagt tatcaaactg tgcggtcgtg aactggttcg tgctcagatc    60
gctatctgcg gtatgtctac ctggtctggc gggggaggca gcgggggagg cgggtccgga   120
ggcgggggat ctggcggggg aggcagtggg ggaggcggga gcggaggcgg gggccctgcg   180
ctgtactctg ctctggctaa caaatgctgc cacgttggtt gcaccaaacg ttctctggct   240
cgtttctgc                                                           249

<210> SEQ ID NO 33
<211> LENGTH: 186
<212> TYPE: DNA
<213> ORGANISM: Artificial Sequence
<220> FEATURE:

<223> OTHER INFORMATION: Description of Artificial Sequence: Synthetic
       polynucleotide

<400> SEQUENCE: 33
gactcttgga tggaagaagt tatcaaactg tgcggtcgtg aactggttcg tgctcagatc    60
gctatctgcg gtatgtctac ctggtctggc ggggtggga gcggggagg cggacagctg    120 tactctgctc tggctaacaa atgctgccac gttggttgca ccaaacgttc tctggctcgt   180
ttctgc                                                              186

<210> SEQ ID NO 34
<211> LENGTH: 186
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 34
gattcatgga tggaggaggt catcaaactg tgtggcaggg agctggtgag agcacagatc    60
gctatctgtg ggatgagcac ctggagtggc gggggaggga gcggggagg cggacagctg    120 tactctgcac tggccaataa atgctgccac gtgggatgta ccaagagatc tctggcacgg   180
ttttgt                                                              186

<210> SEQ ID NO 35
<211> LENGTH: 177
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 35
gactcttgga tggaagaagt tatcaaactg tgcggtcgtg aactggttcg tgctcagatc    60
gctatctgcg gtatgtctac ctggtctggc ggagggcccc gccggcagct gtactctgct   120
ctggctaaca aatgctgcca cgttggttgc accaaacgtt ctctggctcg tttctgc     177

<210> SEQ ID NO 36
<211> LENGTH: 213
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 36
gactcttgga tggaagaagt tatcaaactg tgcggtcgtg aactggttcg tgctcagatc    60
gctatctgcg gtatgtctac ctggtctggc ggaggcggat ccggggcgg gggttccggc    120 gggggtggga gcggggagg ccagctgtac tctgctctgg ctaacaaatg ctgccacgtt    180
ggttgcacca aacgttctct ggctcgtttc tgc                                213

<210> SEQ ID NO 37
<211> LENGTH: 161
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 37

```
Asp Ser Trp Met Glu Val Ile Lys Leu Cys Gly Arg Glu Leu Val
1               5                   10                  15

Arg Ala Gln Ile Ala Ile Cys Gly Met Ser Thr Trp Ser Lys Arg Ser
                20                  25                  30

Leu Ser Gln Glu Asp Ala Pro Gln Thr Pro Arg Pro Val Ala Glu Ile
            35                  40                  45

Val Pro Ser Phe Ile Asn Lys Asp Thr Glu Thr Ile Asn Met Met Ser
50                  55                  60

Glu Phe Val Ala Asn Leu Pro Gln Glu Leu Lys Leu Thr Leu Ser Glu
65                  70                  75                  80

Met Gln Pro Ala Leu Pro Gln Leu Gln Gln His Val Pro Val Leu Lys
                85                  90                  95

Asp Ser Ser Leu Leu Phe Glu Glu Phe Lys Lys Leu Ile Arg Asn Arg
            100                 105                 110

Gln Ser Glu Ala Ala Asp Ser Ser Pro Ser Glu Leu Lys Tyr Leu Gly
        115                 120                 125

Leu Asp Thr His Ser Arg Lys Lys Arg Gln Leu Tyr Ser Ala Leu Ala
    130                 135                 140

Asn Lys Cys Cys His Val Gly Cys Thr Lys Arg Ser Leu Ala Arg Phe
145                 150                 155                 160

Cys
```

<210> SEQ ID NO 38
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Ser Trp Met Glu Val Ile Lys Leu Cys Gly Arg Glu Leu Val
1               5                   10                  15

Arg Ala Gln Ile Ala Ile Cys Gly Met Ser Thr Trp Ser Lys Arg Gly
                20                  25                  30

Gly Gly Gly Ser Gly Thr Ser Glu Ser Ala Thr Pro Glu Ser Gly Pro
            35                  40                  45

Gly Ser Glu Pro Ala Thr Ser Gly Ser Glu Thr Pro Gly Thr Ser Glu
50                  55                  60

Ser Ala Thr Pro Glu Ser Gly Pro Gly Ser Glu Pro Ala Thr Ser Gly
65                  70                  75                  80

Ser Glu Thr Pro Gly Thr Gly Gly Gly Ser His His His His His
                85                  90                  95

His Gly Gly Gly Gly Ser Ser Glu Ser Ala Thr Pro Glu Ser Gly Pro
            100                 105                 110

Gly Thr Ser Thr Glu Pro Ser Glu Gly Ser Ala Pro Gly Ser Pro Ala
        115                 120                 125

Gly Ser Pro Thr Ser Thr Glu Glu Gly Thr Ser Glu Ser Ala Thr Pro
    130                 135                 140

Glu Ser Gly Pro Gly Ser Glu Gly Gly Gly Gly Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Lys Arg Gly
            20                  25                  30

Gly Gly Gly Ser Ser Gly Ser Glu Thr Pro Gly Thr Ser Glu Ser Ala
        35                  40                  45

Thr Pro Glu Ser Gly Gly Gly Gly Ser His His His His His His
    50                  55                  60

Gly Gly Gly Gly Ser Pro Gly Ser Pro Gly Pro Gly Thr Ser Thr Glu
65                  70                  75                  80

Pro Ser Glu Gly Ser Ala Pro Gly Gly Gly Ser Arg Lys Lys Arg
                85                  90                  95

Gln Leu Tyr Ser Ala Leu Ala Asn Lys Cys Cys His Val Gly Cys Thr
            100                 105                 110

Lys Arg Ser Leu Ala Arg Phe Cys
        115                 120

<210> SEQ ID NO 40
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Ser Gly Ser
            20                  25                  30

Glu Thr Pro Gly Thr Ser Glu Ser Ala Thr Pro Glu Ser Gly Pro Gly
        35                  40                  45

Ser Pro Gly Pro Gly Thr Ser Thr Glu Pro Ser Glu Gly Ser Ala Pro
    50                  55                  60

Gln Leu Tyr Ser Ala Leu Ala Asn Lys Cys Cys His Val Gly Cys Thr
65                  70                  75                  80

Lys Arg Ser Leu Ala Arg Phe Cys
                85

<210> SEQ ID NO 41
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Arg Arg Glu

```
                        20                  25                  30

Ala Glu Asp Leu Gln Val Gly Gln Val Glu Leu Gly Gly Gly Pro Gly
            35                  40                  45

Ala Gly Ser Leu Gln Pro Leu Ala Leu Glu Gly Ser Leu Gln Lys Arg
        50                  55                  60

Gln Leu Tyr Ser Ala Leu Ala Asn Lys Cys Cys His Val Gly Cys Thr
 65                  70                  75                  80

Lys Arg Ser Leu Ala Arg Phe Cys
                85

<210> SEQ ID NO 42
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ser Trp Met Glu Glu Val Ile Lys Leu Cys Gly Arg Glu Leu Val
 1               5                  10                  15

Arg Ala Gln Ile Ala Ile Cys Gly Met Ser Thr Trp Ser Ser Gly Ser
            20                  25                  30

Glu Thr Pro Gly Thr Ser Glu Ser Ala Thr Pro Glu Ser Gly Pro Gly
        35                  40                  45

Ser Pro Gln Leu Tyr Ser Ala Leu Ala Asn Lys Cys Cys His Val Gly
    50                  55                  60

Cys Thr Lys Arg Ser Leu Ala Arg Phe Cys
 65                  70

<210> SEQ ID NO 43
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ser Trp Met Glu Glu Val Ile Lys Leu Cys Gly Arg Glu Leu Val
 1               5                  10                  15

Arg Ala Gln Ile Ala Ile Cys Gly Met Ser Thr Trp Ser Lys Arg
            20                  25                  30

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Lys Lys Arg Gln Leu Tyr Ser Ala Leu Ala Asn Lys Cys Cys His
 1               5                  10                  15

Val Gly Cys Thr Lys Arg Ser Leu Ala Arg Phe Cys
            20                  25

<210> SEQ ID NO 45
<211> LENGTH: 24
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 45

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 47
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Ser Gly Gly Gly Ser Gly Gly Gly Gly
        35                  40                  45

Ser Gly Gly Gly Ser Gly Gly Gly Ser Gln Leu Tyr Ser Ala
    50                  55                  60

Leu Ala Asn Lys Cys Cys His Val Gly Cys Thr Lys Arg Ser Leu Ala
65                  70                  75                  80

Arg Phe Cys

<210> SEQ ID NO 48
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Ser Gly Gly Gly Ser Gly Gly Gly Gly
        35                  40                  45

Ser Gly Gly Gly Gly Ser Gly Gly Gly Gly Pro Ala Leu Tyr Ser Ala
    50                  55                  60

```
Leu Ala Asn Lys Cys Cys His Val Gly Cys Thr Lys Arg Ser Leu Ala
 65                  70                  75                  80

Arg Phe Cys

<210> SEQ ID NO 49
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Gln Leu Tyr Ser Ala Leu Ala Asn Lys Cys
        35                  40                  45

Cys His Val Gly Cys Thr Lys Arg Ser Leu Ala Arg Phe Cys
    50                  55                  60

<210> SEQ ID NO 50
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Gln Leu Tyr Ser Ala Leu Ala Asn Lys Cys
        35                  40                  45

Cys His Val Gly Cys Thr Lys Arg Ser Leu Ala Arg Phe Cys
    50                  55                  60

<210> SEQ ID NO 51
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Pro Arg Arg Gln Leu Tyr Ser Ala Leu Ala Asn Lys Cys Cys His Val
        35                  40                  45

Gly Cys Thr Lys Arg Ser Leu Ala Arg Phe Cys
    50                  55

<210> SEQ ID NO 52
<211> LENGTH: 70
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 52

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gly Gly Gly
            20                  25                  30

Gly Ser Gly Gly Gly Gly Ser Gly Gly Gly Ser Gly Gly Gly Gln
        35                  40                  45

Leu Tyr Ser Ala Leu Ala Asn Lys Cys Cys His Val Gly Cys Thr Lys
    50                  55                  60

Arg Ser Leu Ala Arg Phe
65                  70

<210> SEQ ID NO 53
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 53

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 54
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Gly" repeating units

<400> SEQUENCE: 54

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly
    50
```

-continued

```
<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Gly Gly Pro Ser Ser Gly Ala Pro Pro Ser Gly Gly Gly Gly
1               5                   10                  15

Gly

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Pro Ser Ser Gly Ala Pro Pro Ser Gly Gly Gly Gly Gly
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Ala Ala Ala Lys Glu Ala Ala Ala Lys Glu Ala Ala Ala Lys
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Pro Ser Ser Gly Ala Pro Pro Ser Gly Gly Gly Gly Ser
1               5                   10                  15

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Ser Glu Thr Pro Gly Thr Ser Glu Ser Ala Thr Pro Glu Ser
1               5                   10                  15

Gly Pro Gly Ser Pro
            20

<210> SEQ ID NO 60
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 60

Gly Gly Gly Gly Ser Gly Gly Gly Ser Gly Gly Gly Ser Gly
1               5                   10                  15

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Gly Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Gly Gly Ser
1               5

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
                20                  25                  30

Glu Ser Gly Pro Gly Ser Glu Pro Ala Thr Ser Gly Ser Glu Thr Pro
            35                  40                  45

Gly Thr Gly Gly Gly Gly Ser His His His His His Gly Gly Gly
        50                  55                  60

Gly Ser Ser Glu Ser Ala Thr Pro Glu Ser Gly Pro Gly Thr Ser Thr
65                  70                  75                  80

Glu Pro Ser Glu Gly Ser Ala Pro Gly Ser Pro Ala Gly Ser Pro Thr
                85                  90                  95

Ser Thr Glu Glu Gly Thr Ser Glu Ser Ala Thr Pro Glu Ser Gly Pro
                100                 105                 110

Gly Ser Glu Gly
        115

<210> SEQ ID NO 64
<211> LENGTH: 51
<212> TYPE: PRT
<213> ORGANISM: Artificial Sequence
<220> FEATURE:
<223> OTHER INFORMATION: Description of Artificial Sequence: Synthetic
```

```
                         polypeptide

<400> SEQUENCE: 64

Ser Gly Ser Glu Thr Pro Gly Thr Ser Glu Ser Ala Thr Pro Glu Ser
1               5                   10                  15

Gly Gly Gly Gly Gly Ser His His His His His Gly Gly Gly Gly
            20                  25                  30

Ser Pro Gly Ser Pro Gly Pro Gly Thr Ser Thr Glu Pro Ser Glu Gly
        35                  40                  45

Ser Ala Pro
    50

<210> SEQ ID NO 65
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Gly Ser Glu Thr Pro Gly Thr Ser Glu Ser Ala Thr Pro Glu Ser
1               5                   10                  15

Gly Pro Gly Ser Pro
            20

<210> SEQ ID NO 67
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Gly Ser Glu Thr Pro Gly Thr Ser Glu Ser Ala Thr Pro Glu Ser
1               5                   10                  15

Gly Pro Gly Ser Pro Gly Pro Gly Thr Ser Thr Glu Pro Ser Glu Gly
            20                  25                  30

Ser Ala Pro
        35

<210> SEQ ID NO 68
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 68

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Gly Gly Gly Gly
1               5

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly Ser Gly Gly Gly Gly Ser Gly Gly Gly Gly Ser Gly
1               5                   10                  15

Gly Gly

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Pro Arg Arg
1               5

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Ser Gly Phe Ser Leu Ser Thr Ser Gly Met Ser Val Gly
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73
```

```
Asp Ile Trp Trp Asp Asp Lys Lys Asp Tyr Asn Pro Ser Leu Lys Ser
1               5                   10                  15

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Met Ile Thr Asn Trp Tyr Phe Asp Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe, Ala, Gly or Pro
<220> FEATURE:
<221> NAME/KEY: MOD_RES
<222> LOCATION: (6)..(6)
<223> OTHER INFORMATION: Gly, Ala, Ser, Thr or Pro
<220> FEATURE:
<221> NAME/KEY: MOD_RES
<222> LOCATION: (7)..(7)
<223> OTHER INFORMATION: Gly, Ala, Val, Leu or Pro

<400> SEQUENCE: 75

Ser Met Ile Thr Xaa Xaa Xaa Phe Asp Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe, Ala, Gly or Pro
<220> FEATURE:
<221> NAME/KEY: MOD_RES
<222> LOCATION: (6)..(6)
<223> OTHER INFORMATION: Trp, Gly, Ala, Ser, Thr or Pro
<220> FEATURE:
<221> NAME/KEY: MOD_RES
<222> LOCATION: (7)..(7)
<223> OTHER INFORMATION: Tyr, Gly, Ala, Val, Leu or Pro

<400> SEQUENCE: 76

Ser Met Ile Thr Xaa Xaa Xaa Phe Asp Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Asn, Phe, Ala, Gly or Pro
<220> FEATURE:
<221> NAME/KEY: MOD_RES
<222> LOCATION: (6)..(6)
<223> OTHER INFORMATION: Gly, Ala, Ser, Thr or Pro
<220> FEATURE:
<221> NAME/KEY: MOD_RES
<222> LOCATION: (7)..(7)
<223> OTHER INFORMATION: Tyr, Gly, Ala, Val, Leu or Pro

<400> SEQUENCE: 77

Ser Met Ile Thr Xaa Xaa Xaa Phe Asp Val
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asn, Phe, Ala, Gly or Pro
<220> FEATURE:
<221> NAME/KEY: MOD_RES
<222> LOCATION: (6)..(6)
<223> OTHER INFORMATION: Trp, Gly, Ala, Ser, Thr or Pro
<220> FEATURE:
<221> NAME/KEY: MOD_RES
<222> LOCATION: (7)..(7)
<223> OTHER INFORMATION: Gly, Ala, Val, Leu or Pro

<400> SEQUENCE: 78

Ser Met Ile Thr Xaa Xaa Xaa Phe Asp Val
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Met Ile Thr Phe Gly Gly Phe Asp Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Met Ile Thr Asn Ala Tyr Phe Asp Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 81

Ser Met Ile Thr Asn Gly Tyr Phe Asp Val
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Met Ile Thr Phe Trp Tyr Phe Asp Val
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Met Ile Thr Phe Gly Tyr Phe Asp Val
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Met Ile Thr Phe Ala Tyr Phe Asp Val
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Met Ile Thr Phe Ala Gly Phe Asp Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Met Ile Thr Asn Gly Gly Phe Asp Val
1               5                   10

<210> SEQ ID NO 87
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Met Ile Thr Asn Ala Gly Phe Asp Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Met Ile Thr Asn Trp Gly Phe Asp Val
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Cys Gln Leu Ser Val Gly Tyr Met His
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Thr Ser Lys Leu Ala Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Phe Gln Gly Ser Gly Tyr Pro Phe Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Tyr, Phe, Trp, Pro, Leu, Val or Ala
```

```
<220> FEATURE:
<221> NAME/KEY: MOD_RES
<222> LOCATION: (4)..(4)
<223> OTHER INFORMATION: Ser, Asn, Gly, Ala, Val, Leu or Pro

<400> SEQUENCE: 92

Phe Gln Xaa Xaa Gly Tyr Pro Phe Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Trp, Pro, Leu, Val or Ala
<220> FEATURE:
<221> NAME/KEY: MOD_RES
<222> LOCATION: (4)..(4)
<223> OTHER INFORMATION: Ser, Asn, Gly, Ala, Val, Leu or Pro

<400> SEQUENCE: 93

Phe Gln Xaa Xaa Gly Tyr Pro Phe Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Tyr, Phe, Trp, Pro, Leu, Val or Ala
<220> FEATURE:
<221> NAME/KEY: MOD_RES
<222> LOCATION: (4)..(4)
<223> OTHER INFORMATION: Asn, Gly, Ala, Val, Leu or Pro

<400> SEQUENCE: 94

Phe Gln Xaa Xaa Gly Tyr Pro Phe Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Gln Tyr Ser Gly Tyr Pro Phe Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96
```

Phe Gln Gly Asn Gly Tyr Pro Phe Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Phe Gln Tyr Asn Gly Tyr Pro Phe Thr
1               5

<210> SEQ ID NO 98
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
                20                  25                  30

Ser Arg Thr Pro Glu Val Thr Cys Val Val Val Asp Val Ser His Glu
            35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 99
<211> LENGTH: 4
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 99

Arg Lys Lys Arg
1
```